United States Patent
Gombert et al.

(10) Patent No.: US 10,273,267 B2
(45) Date of Patent: *Apr. 30, 2019

(54) BETA-HAIRPIN PEPTIDOMIMETICS AS SELECTIVE ELASTASE INHIBITORS

(71) Applicant: POLYPHOR AG, Allschwil (CH)

(72) Inventors: Frank Otto Gombert, Basel (CH); Daniel Obrecht, Bättwil (CH); Odile Sellier-Kessler, Baldersheim (FR); Alexander Lederer, Basel (CH); Christian Ludin, Oberwil (CH); Manuella Schmitt-Billet, Hagental-le-Bas (FR); Steffen Weinbrenner, Constance (DE)

(73) Assignee: POLYPHOR AG, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/107,575

(22) PCT Filed: Dec. 27, 2013

(86) PCT No.: PCT/EP2013/078073
§ 371 (c)(1),
(2) Date: Jun. 23, 2016

(87) PCT Pub. No.: WO2015/096873
PCT Pub. Date: Jul. 2, 2015

(65) Prior Publication Data
US 2016/0333053 A1    Nov. 17, 2016

(51) Int. Cl.
*C07K 7/64* (2006.01)
*C07K 14/81* (2006.01)
*A61K 38/00* (2006.01)

(52) U.S. Cl.
CPC .............. *C07K 7/64* (2013.01); *C07K 14/811* (2013.01); *A61K 38/00* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1

FOREIGN PATENT DOCUMENTS

WO   WO 2006/087001 A1   8/2006

OTHER PUBLICATIONS

Sporn et at, "Chemoprevention of Cancer," Carcinogenesis, vol. 21 (2000), 525-530.*
International Search Report (Form PCT/ISA/210), dated Feb. 6, 2014, for International Application No. PCT/EP2013/078073.
McBride et al., "Peptide Mimics of the Bowman-Birk Inhibitor Reactive Site Loop," Biopolymers, vol. 66, No. 2, Jan. 2002, pp. 79-92, XP55099422.

* cited by examiner

*Primary Examiner* — Thomas S Heard
(74) *Attorney, Agent, or Firm* — Birch, Stewart, Kolasch & Birch, LLP

(57) ABSTRACT

β-Hairpin peptidomimetics of the general formula cyclo(-Xaa$^1$-Xaa$^2$-Thr$^3$-Xaa$^4$-Ser$^5$-Xaa$^6$-Xaa$^7$-Xaa$^8$-Xaa$^9$-Xaa$^{10}$-Xaa$^{11}$-Xaa$^{12}$-Xaa$^{13}$-) and pharmaceutically acceptable salts thereof, with Xaa$^1$, Xaa$^2$, Xaa$^4$, Xaa$^6$, Xaa$^7$, Xaa$^8$, Xaa$^9$, Xaa$^{10}$, Xaa$^{11}$, Xaa$^{12}$ and Xaa$^{13}$ being amino acid residues of certain types which are defined in the description and the claims, have elastase inhibitory properties, especially against human neutrophil elastase, and can be used for preventing infections or diseases related to such infections in healthy individuals or for slowing infections in infected patients. The compounds of the invention can further be used where cancer, or immunological diseases, or pulmonary diseases, or cardiovascular diseases, or neurodegenerative diseases, or inflammation, or diseases related to inflammation, are mediated or resulting from elastase activity. These peptidomimetics can be manufactured by a process which is based on a mixed solid- and solution phase synthetic strategy.

12 Claims, No Drawings

BETA-HAIRPIN PEPTIDOMIMETICS AS SELECTIVE ELASTASE INHIBITORS

The β-hairpin peptidomimetics of the invention are compounds of general formula cyclo(Xaa$^1$-Xaa$^2$-Thr$^3$-Xaa$^4$-Ser$^5$-Xaa$^6$-Xaa$^7$-Xaa$^8$-Xaa$^9$-Xaa$^{10}$-Xaa$^{11}$-Xaa$^{12}$-Xaa$^{13}$-), and pharmaceutically acceptable salts thereof, with Xaa$^1$, Xaa$^2$, Xaa$^4$, Xaa$^6$, Xaa$^7$, Xaa$^8$, Xaa$^9$, Xaa$^{10}$, Xaa$^{11}$, Xaa$^{12}$ and Xaa$^{13}$ being amino acid residues of certain types which are defined in the description and the claims.

These β-hairpin peptidomimetics are useful as inhibitors of protease enzymes and are especially valuable as inhibitors of certain serine proteases such as elastase.

In addition the present invention provides an efficient process by which these compounds can, if desired, be made in library-format.

The β-hairpin peptidomimetics of the invention show high inhibitory activity against human neutrophil elastase while having low inhibitory activity against proteinase 3 and an unexpected low inhibitory activity against porcine pancreatic elastase (PPE). These favourable activity/selectivity profiles depend on the proper choice of certain types of α-, β- or γ-amino acid residues and their positions in the monocyclic peptidomimetic.

Inhibitors of proteases are emerging with promising therapeutic uses in the treatment of diseases such as cancers (R. P. Beckett, A. Davidson, A. H. Drummond, M. Whittaker, *Drug Disc. Today* 1996, 1, 16-26; L. L. Johnson, R. Dyer, D. J. Hupe, *Curr. Opin. Chem. Biol.* 1998, 2, 466-71; D. Leung, G. Abbenante, and D. P. Fairlie, *J. Med. Chem.* 2000, 43, 305-341, T. Rockway, *Expert Opin. Ther. Patents* 2003, 13, 773-786), parasitic, fungal, and viral infections [e.g. schistosomiasis (M. M. Becker, S. A. Harrop, J. P. Dalton, B. H. Kalinna, D. P. McManus, D. P. Brindley, *J. Biol. Chem.* 1995, 270, 24496-501); *C. albicans* (C. Abad-Zapetero, R. Goldman, S. W. Muchmore, C. Hutchins, K. Stewart, J. Navaza, C. D. Payne, T. L. Ray, *Protein Sci.* 1996, 5, 640-52), HIV (A. Wlodawer, J. W. Erickson, *Annu. Rev. Biochem.* 1993, 62, 543-85; P. L. Darke, J. R. Huff, *Adv. Pharmacol.* 1994, 5, 399-454), hepatitis (J. L. Kim, K. A. Morgenstern, C. Lin, T. Fox, M. D. Dwyer, J. A. Landro, S. P. Chambers, W. Markland, C. A. Lepre, E. T. O'Malley, S. L. Harbeson, C. M. Rice, M. A. Murcko, P. R. Caron, J. A. Thomson, *Cell,* 1996, 87, 343-55; R. A. Love, H. E. Parge, J. A. Wickersham, Z. Hostomsky, N. Habuka, E. W. Moomaw, T. Adachi, Z. Hostomska, *Cell,* 1996, 87, 331-342), herpes (W. Gibson, M. R. Hall, *Drug. Des. Discov.* 1997, 15, 39-47)], and inflammatory, immunological, respiratory (P. R. Bernstein, P. D. Edwards, J. C. Williams, *Prog. Med. Chem.* 1994, 31, 59-120; T. E. Hugli, *Trends Biotechnol.* 1996, 14, 409-12), cardiovascular (M. T. Stubbs, W. A. Bode, *Thromb. Res.* 1993, 69, 1-58; H. Fukami et al, *Current Pharmaceutical Design* 1998, 4, 439-453), and neurodegenerative defects including Alzheimer's disease (R. Vassar, B. D. Bennett, S. Babu-Kahn, S. Kahn, E. A. Mendiaz, *Science,* 1999, 286, 735-41), angiogenesis (M. Kaatinen et al, *Atherosklerosis* 1996, 123 1-2, 123-131), and multiple sclerosis (M. Z. Ibrahim et al, *J. Neuroimmunol* 1996, 70, 131-138.

As most proteases bind their substrates in extended or β-strand conformations, good inhibitors must thus be able to mimic such a conformation. β-hairpin mimetics are thus ideally suited to lock peptide sequences in an extended conformation.

Among proteases, serine proteases constitute important therapeutic targets. Serine proteases are classified by their substrate specificity, particularly by the type of residue found at P1, as either trypsin-like (positively charged residues Lys/Arg preferred at P1), elastase-like (small hydrophobic residues Ala/Val at P1), or chymotrypsin-like (large hydrophobic residues Phe/Tyr/Leu at P1). Serine proteases for which protease-inhibitor X-ray crystal data are available in the PDB data base (PDB: www.rcsb.org/pdb) include trypsin, α-chymotrypsin, γ-chymotrypsin, human neutrophil elastase, porcine pancreatic elastase, thrombin, subtilisin, human cytomegalovirus protease A, *achromobacter* protease 1, human cathepsin G, glutamic acid-specific protease, carbopeptidase D, blood coagulation factor VIIa, porcine factor IXA, mesentericopeptidase, HCV protease, and thermitase. Other serine proteases which are of therapeutic interest include tryptase, complement convertase, hepatitis C-NS3 protease. Inhibitors of thrombin (e.g. J. L. Metha, L. Y. Chen, W. W. Nichols, C. Mattsson, D. Gustaffson, T. G. P. Saldeen, *J. Cardiovasc. Pharmacol.* 1998, 31, 345-51; C. Lila, P. Gloanec, L. Cadet, Y. Herve, J. Fournier, F. Leborgne, T. J. Verbeuren, G. DeNanteuil, *Synth. Comm.* 1998, 28, 4419-29) and factor Xa (e.g. J. P. Vacca, *Annu. Rep. Med. Chem.* 1998, 33, 81-90) are in clinical evaluation as antithrombotics, inhibitors of elastase (J. R. Williams, R. C. Falcone, C. Knee, R. L. Stein, A. M. Strimpler, B. Reaves, R. E. Giles, R. D. Krell, *Am. Rev. Respir. Dis.* 1991, 144, 875-83) were in clinical trials for emphysema and other pulmonary diseases, whereas tryptase inhibitors were in phase II clinical trials for asthma (C. Seife, *Science* 1997, 277, 1602-3), urokinase inhibitors for breast cancer, and chymase inhibitors for heart related diseases. Finally, cathepsin G, elastase and proteinase 3 are intimately involved in the modulation of activities of cytokines and their receptors. Particularly at sites of inflammation, high concentration of these three neutrophil serine proteases (NSPs) are released from infiltrating polymorphonuclear cells in close temporal correlation to elevated levels of inflammatory cytokines, strongly indicating that these proteases are involved in the control of cytokine bioactivity and availability (U. Bank, S. Ansorge, *J. Leukoc. Biol.* 2001, 69, 177-90). Thus highly selective inhibitors of elastase constitute valuable targets for novel drug candidates for infectious inflammatory diseases, including lung diseases like chronic obstructive pulmonary disease, acute respiratory distress syndrome, cystic fibrosis and ischemic-reperfusion injury, and in non-infectious processes like glomerulonephritis, arthritis and bullous pemphigoid (H. Ohbayashi, *Epert Opin. Investig. Drugs* 2002, 11, 965-980; B. Korkmaz, T. Moreau, F. Gauthier, *Biochimie* 2008, 90, 227).

Of the many occurring proteinaceous serine protease inhibitors, one is a 14 amino acid cyclic peptide from sunflower seeds, termed sunflower trypsin inhibitor (SFTI-1) (S. Luckett, R. Santiago Garcia, J. J. Barker, A. V. Konarev, P. R. Shewry, A. R. Clarke, R. L. Brady, *J. Mol. Biol.* 1999, 290, 525-533; Y.-Q. Long, S.-L. Lee, C.-Y. Lin, I. J. Enyedy, S. Wang, P. Li, R. B. Dickson, P. P. Roller, *Biorg. & Med. Chem. Lett.* 2001, 11, 2515-2519), which shows both sequence and conformational similarity with the trypsin-reactive loop of the Bowman-Birk family of serine protease inhibitors. The inhibitor adopts a β-hairpin conformation when bound to the active site of bovine β-trypsin. SFTI-1 inhibited β-trypsin ($K_i$<0.1 nM), cathepsin G ($K_i$~0.15 nM), elastase ($K_i$~105 µM), chymotrypsin ($K_i$~7.4 µM) and thrombin ($K_i$~136 mM).

The β-hairpin conformation of the compounds cyclo (-Xaa$^1$-Xaa$^2$-Thr$^3$-Xaa$^4$-Ser$^5$-Xaa$^6$-Xaa$^7$-Xaa$^8$-Xaa$^9$-Xaa$^{10}$-Xaa$^{11}$-Xaa$^{12}$-Xaa$^{13}$-) is based on the β-hairpin loop from the naturally occurring peptide combined with an D-amino acid residue at position 12 and fostered by the conserved amino acid residues Thr and Ser at positions 3 and 5, respectively.

In addition, incorporation of structural elements derived from β- and γ-amino acids has been realized, a new approach which has not previously been evaluated for the development of β-hairpin peptidomimetics of that ring size being useful as inhibitors of protease enzymes. Surprisingly we have found that despite the additional degrees of conformational freedom following insertion of one or two additional methylene groups according to β- or γ-amino acids into the backbone of the β-hairpin peptidomimetics of the invention the favoured activity/selectivity profile mentioned above could be maintained.

As human peptidases generally do not recognize peptides containing β- or γ-amino acids these peptides should be more resistant to proteolytic degradation (M.-I. Aguilar, A. W. Purcell, R. Devi, R. Lew, J. Rossjohn, A. I. Smith, P. Perlmutter, *Org. Biomol. Chem.* 2007, 5, 2884; D. F. Hook, P. Bindschaedler, Y. R. Mahayan, R. Sebesta, P. Kast, D. Seebach, *Chem. Biodivers.* 2005, 2, 591; P. Zubrzak, H. Williams, G. M. Coast, R. E. Isaac, G. Reyes-Rangel, E. Juaristi, J. Zabrocki, R. J. Nachman, *Biopolymers* 2007, 88, 76; S. Sagan, Th. Milcent, R. Ponsinet, O. Convert, O. Tasseau, G. Chassaing, S. Lavielle, O. Lequin, *Eur. J. Biochem.* 2003, 270, 939).

Template-bound hairpin mimetic peptides have been described in the literature (D. Obrecht, M. Altorfer, J. A. Robinson, *Adv. Med. Chem.* 1999, 4, 1-68; J. A. Robinson, *Syn. Lett.* 2000, 4, 429-441), and serine protease-inhibiting template-fixed peptidomimetics and methods for their synthesis have been described in International Patent Applications WO2003/054000 A1, WO2006/087001 A1 and in A. Descours, K. Moehle, A. Renard, J. A. Robinson, *ChemBioChem* 2002, 3, 318-323 but the previously disclosed molecules do neither exhibit such favourable activity/selectivity profiles nor do they have incorporated structural elements derived from β- or γ-amino acid residues.

The ability to generate β-hairpin peptidomimetics using combinatorial and parallel synthesis methods has been established (L. Jiang, K. Moehle, B. Dhanapal, D. Obrecht, J. A. Robinson, *Helv. Chim. Acta.* 2000, 83, 3097-3112). The additional incorporation of structural elements derived from β- and γ-amino acids into β-hairpin mimetics by applying and altering these methods has previously been evaluated for development of CXCR4 antagonizing peptides (WO2010/127704 A1). However, these backbone-cyclized peptides have a larger ring-size and are additionally stabilized by a disulfide-bridge. The methods described herein allow the synthesis and screening of large hairpin mimetic libraries. This considerably facilitates structure-activity studies, and hence the discovery of new molecules with highly potent and selective serine protease inhibitory activity, particularly with such favourable activity/selectivity profiles as described herein, having compound properties suitable for novel drugs.

The β-hairpin peptidomimetics of the present invention are compounds of the general formula

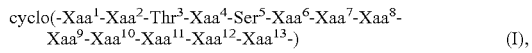

(I), and pharmaceutically acceptable salts thereof,
wherein
Xaa$^1$ is OctGly; Arg; hArg; Cha; a dipeptidic amino acid residue of type O; or of type P; or an amino acid residue with delimited side chain-length of type Q; or of type R;

Xaa$^2$ is Glu; Val; Leu; Nle; Phe; hPhe; DiHPhe; Tyr; hTyr; Trp; or a dipeptidic amino acid residue of type O; or of type P;

Xaa$^4$ is Ala; AllylGly; Abu; or Val;

Xaa$^6$ is Ile; or OctGly;

Xaa$^7$ is Pro; or a N-substituted glycine of type I;

Xaa$^8$ is —B—CO—; or a N-substituted glycine of type I;

Xaa$^9$ is Gln; Tyr; or a β-amino acid residue of type N;

Xaa$^{10}$ is Lys; Asn; Gly; a β-amino acid residue of type N; or a γ-amino acid residue of type M;

Xaa$^1$ is hLeu; Ser; hSer; hSer(Me); Thr; alloThr; Asn; Gln; hGln; Dap; Tyr; His; or a γ-amino acid residue of type M;

Xaa$^{12}$ is Gly; —A—CO—; a N-substituted glycine of type I; or the D-isomer of an amino acid residue of type C; or of type D; or of type E; or of type F; and Xaa$^{13}$ is —B—CO—; a N-substituted glycine of type I; a β-amino acid residue of type N; a γ-amino acid residue of type M; —A—CO—; or the D-isomer of an amino acid residue of type C; or of type D; or of type E; or of type F;

with the proviso that
Xaa$^7$ is a dipeptidic amino acid residue of type O; or of type P;
and/or
Xaa$^2$ is a dipeptidic amino acid residue of type O; or of type P;
and/or
Xaa$^7$ is a N-substituted glycine of type I;
and/or
Xaa$^8$ is Oic; 2Ind; Pip; Azt; or a N-substituted glycine of type I;
and/or
Xaa$^9$ is a β-amino acid residue of type N;
and/or
Xaa$^{10}$ is a β-amino acid residue of type N; or a γ-amino acid residue of type M;
and/or
Xaa$^{11}$ is a γ-amino acid residue of type M;
and/or
Xaa$^{12}$ is a N-substituted glycine of type I; or the D-isomer of an amino acid residue of type C; or of type D; or of type E; or of type F;
and/or
Xaa$^{13}$ is a N-substituted glycine of type I; a β-amino acid residue of type N; a γ-amino acid residue of type M; —A—CO—; or the D-isomer of an amino acid residue of type C; or of type D; or of type E; or of type F;
and with the further proviso that
if Xaa$^{11}$ is Tyr; or His, then
Xaa$^1$ is Arg; hArg; or a dipeptidic amino acid residue of type O;
or of type P;
and/or
Xaa$^2$ is a dipeptidic amino acid residue of type O;
or of type P;

—B—CO— is a residue of an L-α-amino acid with B being a residue of formulae —NR$^{20}$CH(R$^{71}$)—; —NR$^{20}$CH(R$^{72}$)—; —NR$^{20}$CH(R$^{73}$)—; —NR$^{20}$CH(R$^{74}$)—; —NR$^{20}$CH(R$^{84}$)—; or the enantiomer of one of the groups A1 to A37 and A105 as defined hereinafter;

—A—CO— is a residue of an amino acid with A being a group of one of the formulae

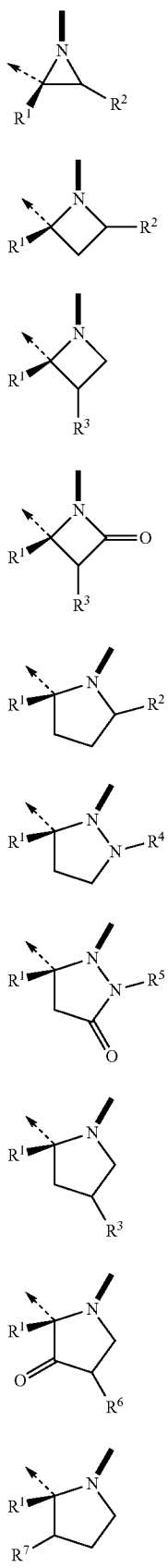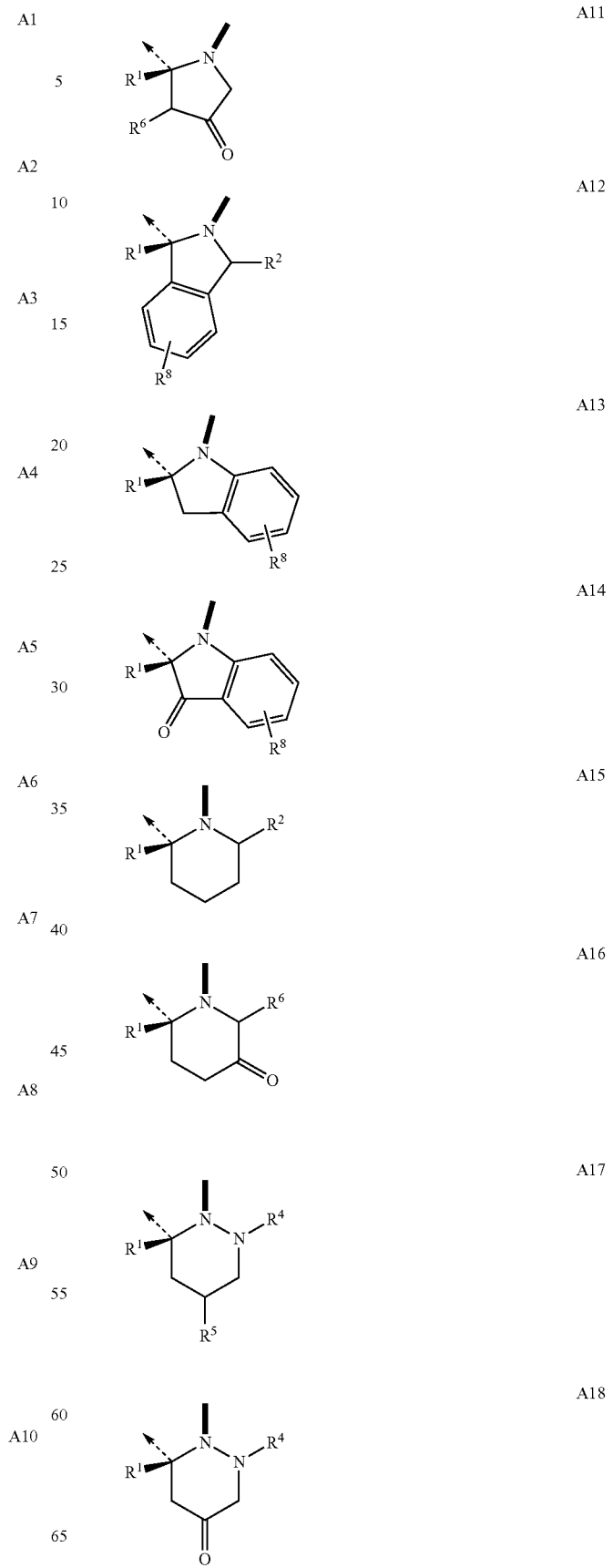

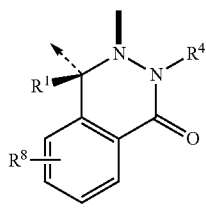 A18
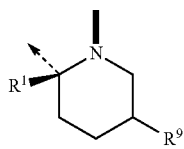 A19
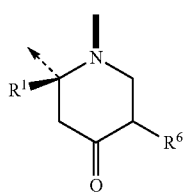 A20
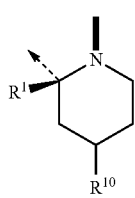 A21
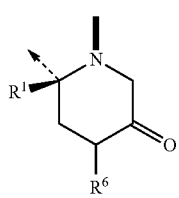 A22
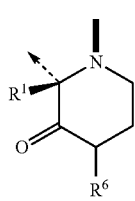 A23
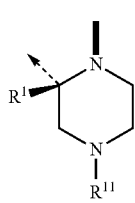 A24
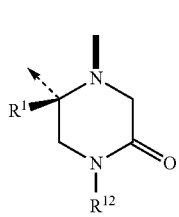 A25
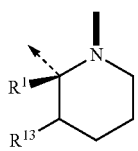 A26
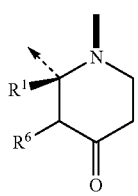 A27
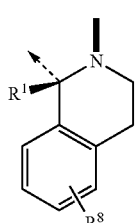 A28
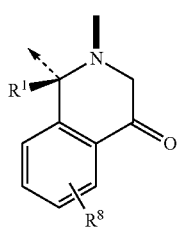 A29
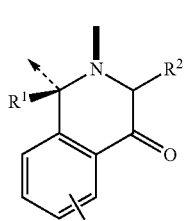 A30
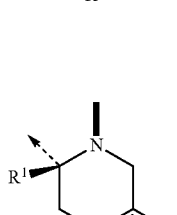 A31
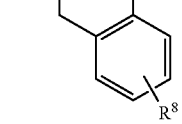 A32
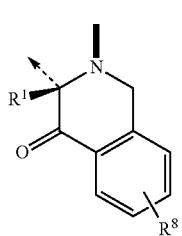 A33

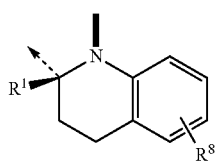
A34
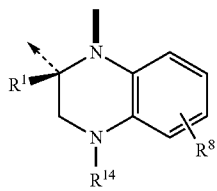
A35
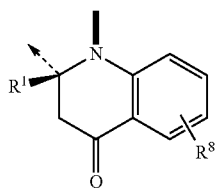
A36
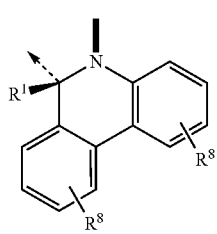
A37
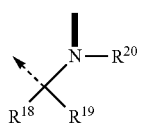
A70
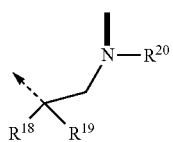
A71
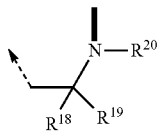
A72
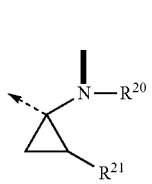
A73
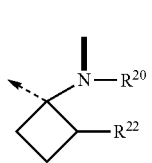
A74
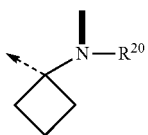
A75
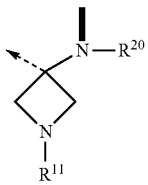
A76
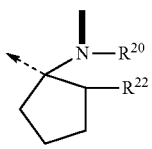
A77
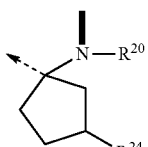
A78
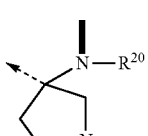
A79
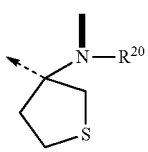
A80
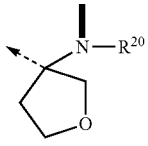
A81
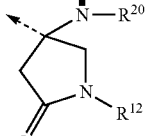
A82
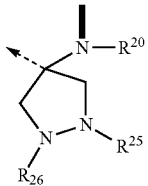
A83

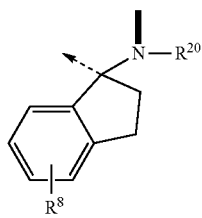
A84
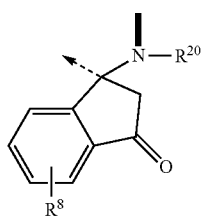
A85
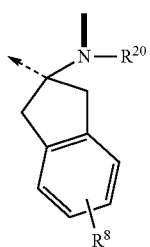
A86
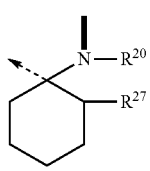
A87
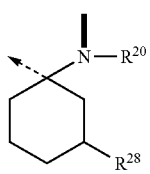
A88
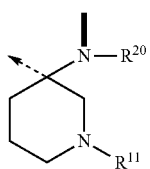
A89
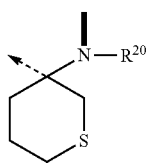
A90
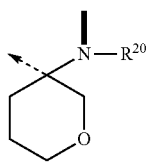
A91
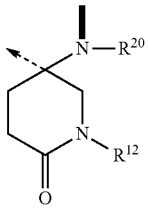
A92
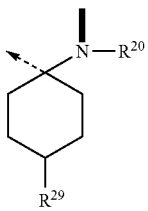
A93
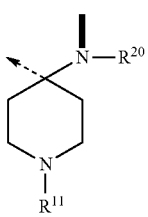
A94
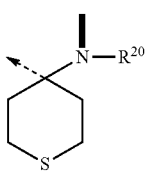
A95
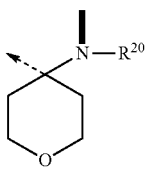
A96
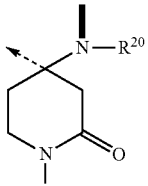
A97
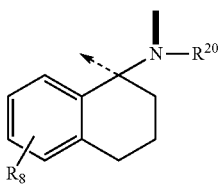
A98
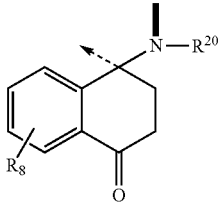
A99

-continued

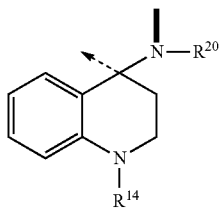
A100

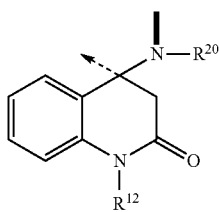
A101

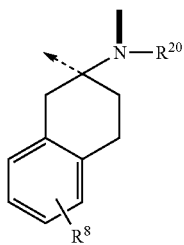
A102

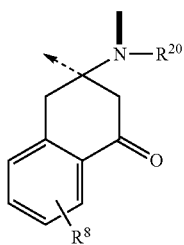
A103

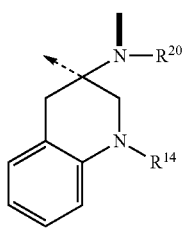
A104

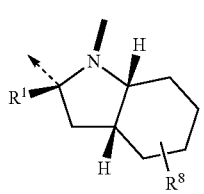
A105

$R^1$ is H; lower alkyl; or aryl-lower alkyl;
$R^2$ is H; alkyl; alkenyl; —$(CH_2)_p(CHR^{61})_sOR^{55}$; —$(CH_2)_p(CHR^{61})_sSR^{56}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_p NR^{20}(CHR^{61})_s COR^{64}$; —$(CH_2)_o(CHR^{61})_sCOOR^{57}$, —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;
$R^3$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_p(CHR^{61})_sOCONR^{33}R^{75}$; —$(CH_2)_o(CHR^{61})_sNR^{20}CONR^{33}R^{82}$; —$(CH_2)_oNR^{20}(CHR^{61})_sCOR^{64}$; —$(CH_2)_o(CHR^{61})_sCOOR^{57}$; —$(CH_2)_o(CHR^{61})_sCONR^{58}R^{51}$; —$(CH_2)_o(CHR^{61})_sPO(OR^{60})_2$; —$(CH_2)_p(CHR^{61})_sSO_2R^{62}$; or —$(CH_2)_q(CR^{61})C_6H_4R^8$;
$R^4$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_mNR^{20}(CHR^{61})_sCOR^{64}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R_8$;
$R^5$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCONR^{33}R^{75}$; —$(CH_2)_o(CHR^{61})_sNR^{20}CONR^{33}R^{82}$; —$(CH_2)_oNR^{20}(CHR^{61})_sCOR^{64}$; —$(CH_2)_o(CHR^{61})_sCOOR^{57}$, —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;
$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_oNR^{20}(CHR^{61})_sCOR^{64}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;
$R^7$ is alkyl; alkenyl; —$(CH_2)_q(CHR^{61})_sOR^{55}$; —$(CH_2)_q(CHR^{61})_sNR^{33}R^{34}$; —$(CH_2)_q(CHR^{61})_sOCONR^{33}R^{75}$; —$(CH_2)_q(CHR^{61})_sNR^{20}CONR^{33}R^{82}$; —$(CH_2)_qNR^{20}(CHR^{61})_sCOR^{64}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_q(CHR^{61})_sC_6H_4R^8$;
$R^8$ is H; Cl; F; $CF_3$; $NO_2$; lower alkyl; lower alkenyl; aryl; aryl-lower alkyl; —$(CH_2)_o(CHR^{61})_sR^{77}$; —$(CH_2)_o(CHR^{61})_sOR^{55}$; —$(CH_2)_o(CHR^{61})_sSR^{56}$; —$(CH_2)_o(CHR^{61})NR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_oNR^{20}(CHR^{61})_sCOR^{64}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sCOR^{64}$;
$R^9$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_oNR^{20}(CHR^{61})_sCOR^{64}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CR^{61})_sSO_2R^{62}$; or —$(CH_2)_o(CHR^{61})_sC_6H_4R^8$;
$R^{10}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_oNR^{20}(CHR^{61})_sCOR^{64}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;
$R^{11}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_mNR^{20}(CHR^{61})_sCOR^{64}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CR^{61})SO_2R^{62}$; or —$(CH_2)_o(CHR^{61})_sC_6H_4R^8$;
$R^{12}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_mNR^{20}(CHR^{61})_sCOR^{64}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_o(CHR^{61})_sSO_2R^{62}$; or —$(CH_2)_r(CHR^{61})C_6H_4R^8$;

$R^{13}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$NR$^{20}$(CHR$^{61}$)$_s$NR$^{20}$CONR$^{33}$R$^{82}$; —(CH$_2$)$_q$NR$^{20}$(CHR$^{61}$)$_s$COR$^{64}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

$R^{14}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_m$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SOR$^{62}$; or —(CH$_2$)$_o$(CHR$^{61}$)$_s$C$_6$H$_4$R$^8$;

$R^{18}$ is lower alkyl; lower alkenyl; —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CHR$^{62}$)$_p$NR$^{20}$(CHR$^{61}$)$_s$COR$^{64}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

$R^{19}$ is alkyl; alkenyl —(CH$_2$)$_p$(CHR$^{61}$)$_s$OR$^{55}$; —(CH$_2$)$_p$(CHR$^{61}$)$_s$SR$^{56}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CHR$^{62}$)$_p$NR$^{20}$(CHR$^{61}$)$_s$COR$^{64}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$; or $R^{18}$ and $R^{19}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—

$R^{20}$ is H; alkyl; alkenyl; or aryl-lower alkyl;

$R^{21}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$CONR$^{33}$R$^{75}$; —(CH$_2$)$_o$(CHR$^{61}$)$_s$NR$^{20}$CONR$^{33}$R$^{82}$; —(CH$_2$)$_o$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{22}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$NR$^2$(CHR$^{61}$)$_s$CR$^4$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{23}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$CONR$^{33}$R$^{75}$; —(CH$_2$)$_o$(CHR$^{61}$)$_s$NR$^{20}$CONR$^{33}$R$^{82}$; —(CH$_2$)$_o$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{25}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_m$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{26}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_m$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$; or $R^{25}$ and $R^{26}$ taken together can form: —(CH$_2$)$_{2-6}$—; —(CH$_2$)$_r$O(CH$_2$)$_r$—; —(CH$_2$)$_r$S(CH$_2$)$_r$—; or —(CH$_2$)$_r$NR$^{57}$(CH$_2$)$_r$—;

$R^{27}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_p$(CHR$^{61}$)$_s$C$_6$H$_4$R$^8$;

$R^{28}$ is alkyl; alkenyl; —(CH$_2$)$_o$(CHR$^{61}$)$_s$—OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$NR$^{20}$(CHR$^{61}$)$_s$COR$^{64}$; —(CH$_2$)$_o$(CHR$^{61}$)$_s$; —COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{29}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$NR$^{20}$(CHR$^{61}$)$_s$COR$^{64}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{33}$ is H; alkyl, alkenyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_m$NR$^{20}$(CHR$^{61}$)$_s$COR$^{64}$; —(CH$_2$)$_o$(CHR$^{61}$)$_s$COR$^{64}$; —(CH$_2$)$_o$(CHR$^{61}$)$_s$—CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{34}$ is H; lower alkyl; aryl, or aryl-lower alkyl; or $R^{33}$ and $R^{34}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

$R^{50}$ is H; lower alkyl; or aryl-lower alkyl;

$R^{55}$ is H; lower alkyl; lower alkenyl; aryl-lower alkyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; —(CH$_2$)$_o$(CHR$^{61}$)$_s$COOR$^{57}$; or —(CH$_2$)$_o$(CHR$^{61}$)$_s$CONR$^{58}$R$^{59}$;

$R^{56}$ is H; lower alkyl; lower alkenyl; aryl-lower alkyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; or —(CH$_2$)$_o$(CHR$^{61}$)$_s$CONR$^{58}$R$^{59}$;

$R^{57}$ is H; lower alkyl; lower alkenyl; aryl lower alkyl; or heteroaryl-lower alkyl;

$R^{58}$ is H; lower alkyl; lower alkenyl; aryl; heteroaryl; aryl-lower alkyl; or heteroaryl-lower alkyl;

$R^{59}$ is H; lower alkyl; lower alkenyl; aryl; heteroaryl; aryl-lower alkyl; or heteroaryl-lower alkyl; or $R^{58}$ and $R^{59}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{60}$ is H; lower alkyl; lower alkenyl; aryl; or aryl-lower alkyl;

$R^{61}$ is alkyl; alkenyl; aryl; heteroaryl; aryl-lower alkyl; heteroaryl-lower alkyl; —$(CH_2)_pOR^{57}$; —$(CH_2)_pNR^{75}R^{82}$; —$(CH_2)_pOCONR^{75}R^{82}$; —$(CH_2)_pNR^{20}CONR^{78}R^{82}$; —$(CH_2)_pNR^{20}(CHR^{61})_sCOR^{64}$; —$(CH_2)_oCOOR^{57}$; —$(CH_2)_oCONR^{58}R^{59}$; or —$(CH_2)_oPO(OR^{60})_2$;

$R^{62}$ is lower alkyl; lower alkenyl; aryl, heteroaryl; or aryl-lower alkyl;

$R^{63}$ is H; lower alkyl; lower alkenyl; aryl; heteroaryl; aryl-lower alkyl; heteroaryl-lower alkyl; —$COR^{64}$; —$COOR^{57}$; —$CONR^{58}R^{59}$; —$SO_2R^{62}$; or —$PO(OR^{60})_2$; or $R^{34}$ and $R^{63}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{64}$ is H; lower alkyl; lower alkenyl; aryl; heteroaryl; aryl-lower alkyl; heteroaryl-lower alkyl; —$(CH_2)_p(CHR^{61})_sOR^{65}$; —$(CH_2)_p(CHR^{61})_sSR^{66}$; —$(CH_2)_p(CHR^{61})_sNR^{34}R^{63}$; —$(CH_2)_p(CHR^{61})_sOCONR^{75}SR^{82}$; or —$(CH_2)_p(CHR^{61})_sNR^{20}CONR^{78}R^{82}$;

$R^{65}$ is H; lower alkyl; lower alkenyl; aryl; aryl-lower alkyl; heteroaryl-lower alkyl; —$COR^{57}$; —$COOR^{57}$; or —$CONR^{58}R^{59}$;

$R^{66}$ is H; lower alkyl; lower alkenyl; aryl; aryl-lower alkyl; heteroaryl-lower alkyl; or —$CONR^{58}R^{59}$;

$R^{67}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{68}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{69}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{70}$ is H; Cl; Br; F; $NO_2$; —$NR^{34}COR^{57}$; —$CF_3$; CN; —$OCF_3$; —$OCHF_2$; —$OR^{57}$; —$SR^{62}$; lower alkyl; or lower alkenyl;

$R^{71}$ is lower alkyl; lower alkenyl; —$(CH_2)_p(CHR^{61})_sOR^{75}$; —$(CH_2)_p(CHR^{61})_sSR^{75}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{75}$; —$(CH_2)_pCONR^{58}R^{59}$; —$(CH_2)_pPO(OR^{62})_2$; —$(CH_2)_pSO_2R^{62}$; or —$(CH_2)_o—C_6R^{67}R^{68}R^{69}R^{75}R^{76}$;

$R^{72}$ is alkyl; alkenyl; lower cycloalkyl; lower cycloalkyl-lower alkyl; —$(CH_2)_p(CHR^{61})_sOR^{85}$; or —$(CH_2)_p(CHR^{61})_sSR^{85}$;

$R^{73}$ is —$(CH_2)_oR^{77}$; —$(CH_2)_rO(CH_2)_oR^{77}$; —$(CH_2)_rS(CH_2)_oR^{77}$; or —$(CH_2)_rNR^{20}(CH_2)_oR^{77}$;

$R^{74}$ is —$(CH_2)_pNR^{78}R^{79}$; —$(CH_2)_pNR^{77}R^{80}$; —$(CH_2)_pC(=NR^{80})NR^{78}R^{79}$; —$(CH_2)_pC(=NOR^{50})NR^{78}R^{79}$; —$(CH_2)_pC(=NNR^{78}R^{79})NR^{78}R^{79}$; —$(CH_2)_pNR^{80}C(=NR^{80})NR^{78}R^{79}$; —$(CH_2)_pN=C(NR^{78}R^{80})NR^{79}R^{80}$; —$(CH_2)_pC_6H_4NR^{78}R^{79}$; —$(CH_2)_pC_6H_4NR^{77}R^{80}$; —$(CH_2)_pC_6H_4C(=NR^{80})NR^{78}R^{79}$; —$(CH_2)_pC_6H_4C(=NOR^{50})NR^{78}R^{79}$; —$(CH_2)_pC_6H_4C(=NNR^{78}R^{79})NR^{78}R^{79}$; —$(CH_2)_pC_6H_4NR^{80}C(=NR^{80})NR^{78}R^{79}$; —$(CH_2)_pC_6H_4N=C(NR^{78}R^{80})NR^{79}R^{80}$; —$(CH_2)_rO(CH_2)_mNR^{78}R^{79}$; —$(CH_2)_rO(CH_2)_mNR^{77}R^{80}$; —$(CH_2)_rO(CH_2)_pNR^{78}R^{79}$; —$(CH_2)_rO(CH_2)_pC(=NOR^{80})NR^{78}R^{79}$; —$(CH_2)_rO(CH_2)_pC(=NNR^{78}R^{79})NR^{78}R^{79}$; —$(CH_2)_rO(CH_2)_mN=C(NR^{78}R^{80})NR^{79}R^{80}$; —$(CH_2)_rO(CH_2)_pC_6H_4C(=NR^{80})NR^{78}R^{79}$; —$(CH_2)_rO(CH_2)_pC_6H_4C(=NR^{80})NR^{78}R^{79}$; —$(CH_2)_rO(CH_2)_pC_6H_4C(=NOR^{50})NR^{78}R^{79}$; —$(CH_2)_rO(CH_2)_pC_6H_4C(=NNR^{78}R^{79})NR^{78}R^{79}$; —$(CH_2)_rO(CH_2)_pC_6H_4NR^{80}C(=NR^{80})NR^{78}R^{79}$; —$(CH_2)_rS(CH_2)_mNR^{78}R^{79}$; —$(CH_2)_rS(CH_2)_mNR^{77}R^{80}$; —$(CH_2)_rS(CH_2)_pC(=NR^{80})NR^{78}R^{79}$; —$(CH_2)_rS(CH_2)_pC(=NOR^{50})NR^{78}R^{79}$; —$(CH_2)_rS(CH_2)_pC(=NNR^{78}R^{79})NR^{78}R^{79}$; —$(CH_2)_rS(CH_2)_mNR^{80}C(=NR^{80})NR^{78}R^{79}$; —$(CH_2)S(CH_2)_mN=C(NR^{78}R^{80})NR^{79}R^{80}$; —$(CH_2)_rS(CH_2)_pC_6H_4NR^{78}R^{79}$; —$(CH_2)_rS(CH_2)_pC_6H_4C(=NR^{80})NR^{78}R^{79}$; —$(CH_2)_rS(CH_2)_pC_6H_4C(=NOR^{50})NR^{78}R^{79}$; —$(CH_2)_rS(CH_2)_pC_6H_4C(=NNR^{78}R^{79})NR^{78}R^{79}$; —$(CH_2)_rS(CH_2)_pC_6H_4NR^{80}C(=NR^{80})NR^{78}R^{79}$; —$(CH_2)_pNR^{80}COR^{64}$; —$(CH_2)_pNR^{80}COR^{77}$; —$(CH_2)_pNR^{80}CONR^{78}R^{79}$; or —$(CH_2)_pC_6H_4NR^{80}CONR^{78}R^{79}$;

$R^{75}$ is lower alkyl; lower alkenyl; lower cycloalkyl; lower cycloalkyl-lower alkyl; or aryl-lower alkyl; or $R^{33}$ and $R^{75}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; or $R^{75}$ and $R^{82}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{76}$ is H; lower alkyl; lower alkenyl; aryl-lower alkyl; —$(CH_2)_oOR^{72}$; —$(CH_2)_oSR^{72}$; —$(CH_2)_oNR^{33}R^{34}$; —$(CH_2)_oOCONR^{33}R^{75}$; —$(CH_2)_oNR^{20}CONR^{33}R^{81}$; —$(CH_2)_oCOOR^{75}$; —$(CH_2)_oCONR^{58}R^{59}$; —$(CH_2)_pPO(OR^{60})_2$; —$(CH_2)_pSO_2R^{62}$; or —$(CH_2)_oCOR^{64}$;

$R^{77}$ is —$C_6R^{67}R^{68}R^{69}R^{70}R^{76}$ with the proviso that at least two of $R^{67}$, $R^{68}$, $R^{69}$ and $R^{70}$ are H; or a heteroaryl group of one of the formulae

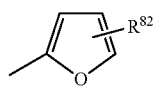

H1

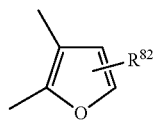

H2

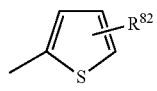

H3

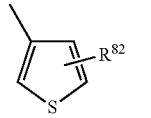

H4

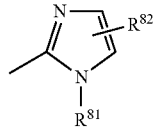

H5

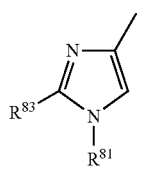

H6

-continued
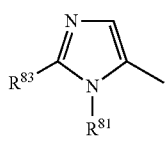 H7
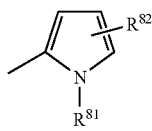 H8
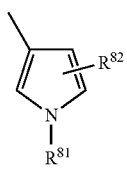 H9
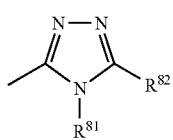 H10
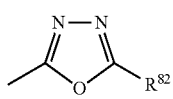 H11
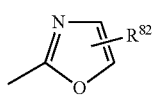 H12
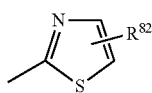 H13
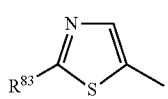 H14
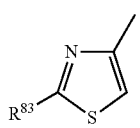 H15
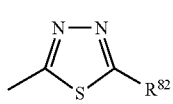 H16
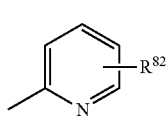 H17
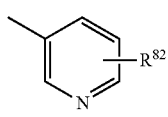 H18
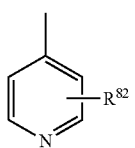 H19
-continued
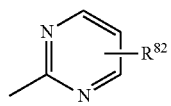 H20
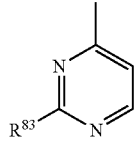 H21
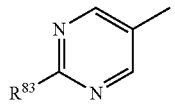 H22
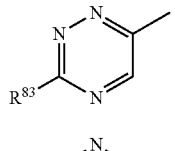 H23
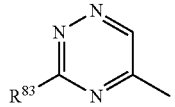 H24
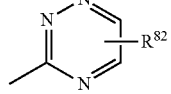 H25
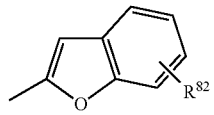 H26
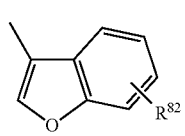 H27
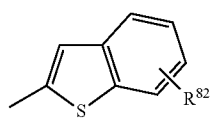 H28
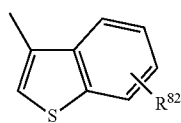 H29
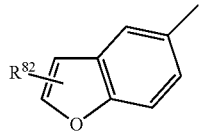 H30
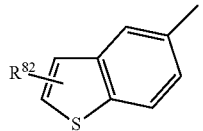 H31

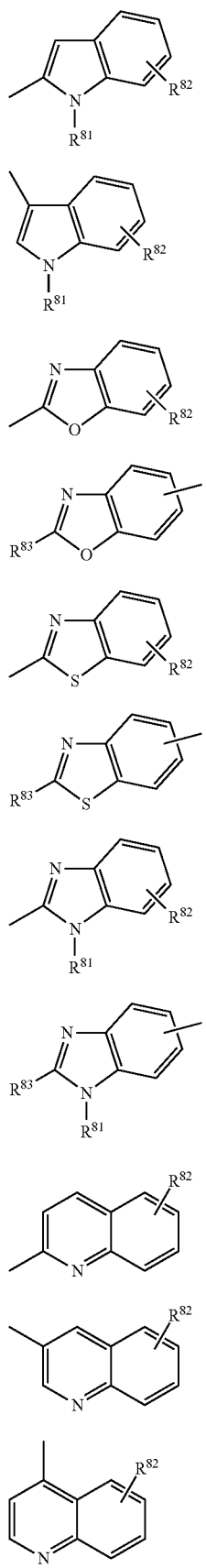
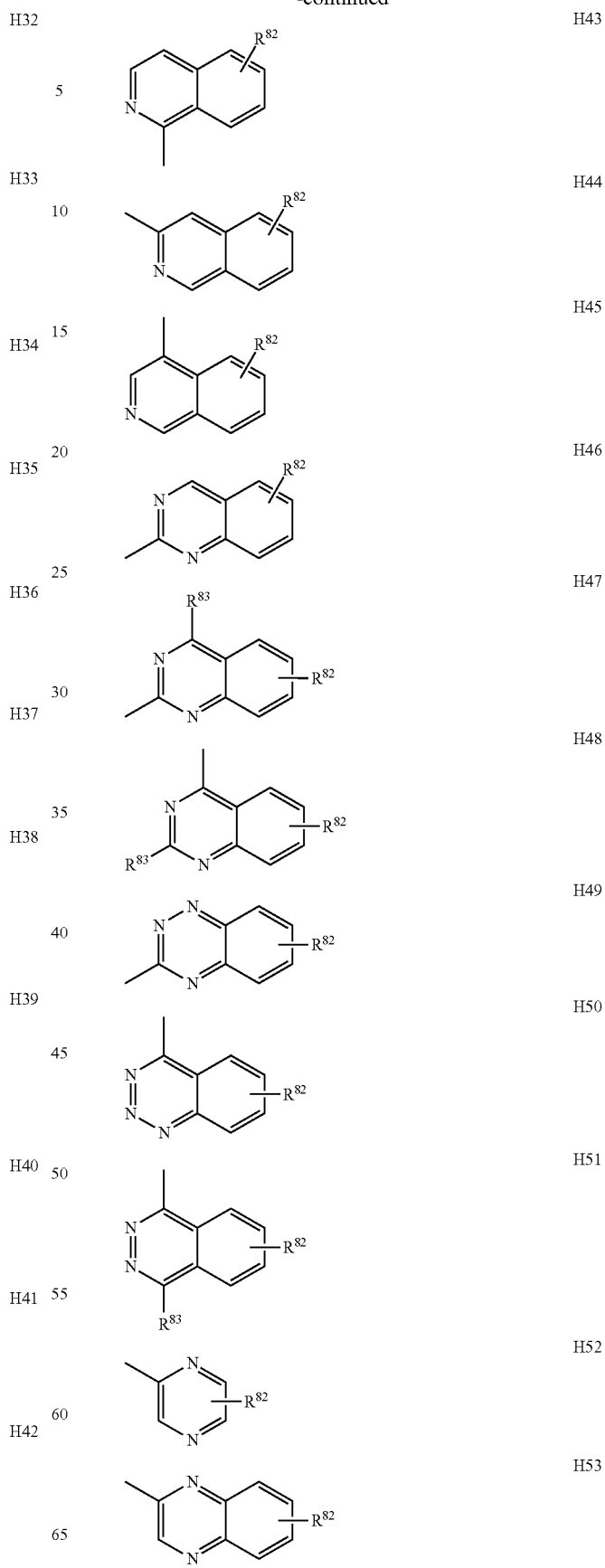

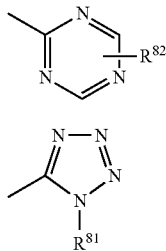

H54

H55

$R^{78}$ is H; lower alkyl; aryl; or aryl-lower alkyl; or
$R^{78}$ and $R^{82}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{79}$ is H; lower alkyl; aryl; or aryl-lower alkyl; or
$R^{78}$ and $R^{79}$, taken together, can be $-(CH_2)_{2-7}-$; $-(CH_2)_2O(CH_2)_2-$; or $-(CH_2)_2NR^{57}(CH_2)_2-$;
$R^{80}$ is H; or lower alkyl;
$R^{81}$ is H; lower alkyl; or aryl-lower alkyl; or
$R^{33}$ and $R^{81}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;
$R^{82}$ is H; $-CF_3$; lower alkyl; aryl; heteroaryl; or aryl-lower alkyl;
$R^{83}$ is H; lower alkyl; aryl; or $-NR^{78}R^{79}$;
$R^{84}$ is $-(CH_2)_p(CHR^{61})_sOH$; $-(CR^{86}R^{87})_pOR^{80}$; $-(CR^{86}R^{87})_pCOOR^{80}$; $-(CH_2)_p(CHR^{61})_sSH$; $-(CR^{86}R^{87})_pSR^{80}$; $-(CH_2)_pCONR^{78}R^{79}$; $-(CH_2)_pNR^{80}CONR^{78}R^{79}$; $-(CH_2)_pC_6H_4CONR^{78}R^{79}$; or $-(CH_2)_pC_6H_4NR^{80}CONR^{78}R^{79}$; $-(CR^{86}R^{87})_pPO(OR^{60})_2$; $-(CR^{86}R^{87})SO_2R^{60}$; $-(CR^{86}R^{87})_sOR^{60}$; $-(CH_2)_p(CHR^{61})_sOPO(OR^{60})_2$; or $-(CH_2)_p(CHR^{61})_sOSO_2R^{60}$;
$R^{85}$ is lower alkyl; or lower alkenyl;
$R^{86}$ is H; lower alkyl, where H is maybe substituted by halogen; or halogen;
$R^{87}$ is H; lower alkyl, where H is maybe substituted by halogen; or halogen;
$R^{88}$ is $R^{74}$ or $R^{84}$;
$R^{89}$ is $-(CH_2)_pNR^{20}CO(CHNHR^{20})R^{72}$; $-(CH_2)_pNR^{20}CO(CHNHR^{20})R^{73}$; $-(CH_2)_pNR^{20}CO(CHNHR^{20})R^{74}$; or $-(CH_2)_pNR^{20}CO(CHNHR^{20})R^{84}$;
$R^{90}$ is $-(CH_2)_pCONR^{20}(CHCOOR^{80})R^{72}$; $-(CH_2)_pCONR^{20}(CHCOOR^{80})R^{73}$; $-(CH_2)_pCONR^{20}(CHCOOR^{80})R^{74}$; or $-(CH_2)_pCONR^{20}(CHCOOR^{80})R^{84}$;
$R^{91}$ is $-(CH_2)_pNR^{20}COR^{75}$;
$R^{92}$ is $-(CH_2)_pCONR^{20}R^{75}$;
m is 2-4; o is 0-4; p is 1-4; q is 0-2; r is 1 or 2; s is 0 or 1;
the amino acid residue of type C is a residue of formula $-NR^{20}CH(R^{72})CO-$;
the amino acid residue of type D is a residue of formula $-NR^{20}CH(R^{73})CO-$;
the amino acid residue of type E is a residue of the formula $-NR^{20}CH(R^{74})CO-$;
the amino acid residue of type F is a residue of the formula $-NR^{20}CH(R^{84})CO-$;
the N-substituted glycine residue of type I is a residue of formula $-NR^{88}CH_2CO-$;
the amino acid residue of type M is a residue of one of the formulae $-NR^{20}CH(R^{73})(CH_2)_2CO-$; $-NR^{20}CH(R^{74})(CH_2)_2CO-$; or $-NR^{20}CH(R^{84})(CH_2)_2CO-$;
the amino acid residue of type N is a residue of one of the formulae $-NR^{20}CH(R^{72})(CH_2)CO-$; $-NR^{20}CH(R^{73})(CH_2)CO-$; $-NR^{20}CH(R^{74})(CH_2)CO-$, or $-NR^{20}CH(R^{84})(CH_2)CO-$;
the amino acid residue of type O is a residue of formula $-NR^{20}CH(R^{89})CO-$;
the amino acid residue of type P is a residue of formula $-NR^{20}CH(R^{90})CO-$;
the amino acid residue of type Q is a residue of formula $-NR^{20}CH(R^{91})CO-$; and
the amino acid residue of type R is a residue of formula $-NR^{20}CH(R^{92})CO-$.

In accordance with the present invention these β-hairpin peptidomimetics can be prepared by a process which comprises (a) coupling an appropriately functionalized solid support with an appropriately N-protected derivative of that amino acid which in the desired end-product corresponds to Xaa$^n$, wherein n is 13, 8, 7, 6, 5 or 4, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product corresponds to Xaa$^{n-1}$, any functional group which may be present in said N-protected amino acid derivative being likewise appropriately protected;

(d) removing the N-protecting group from the product obtained in step (c);

(e) effecting steps substantially corresponding to steps (c) and (d) using appropriately N-protected derivatives of amino acids which in the desired end-product are in positions n–2 to 1, any functional group(s) which may be present in said N-protected amino acid derivatives being likewise appropriately protected;

(f) if n is not 13, further effecting steps substantially corresponding to steps (c) and (d) using appropriately N-protected derivatives of amino acids which in the desired end-product are in positions 13 to n+1, any functional group(s) which may be present in said N-protected amino acid derivatives being likewise appropriately protected;

(g) if desired, before removing the N-protecting group from the product obtained in steps (e) or (f) selectively deprotecting one or several protected functional group(s) present in the molecule and appropriately substituting the reactive group(s) thus liberated by attaching one or several moieties derived from acids, amino acids or amines and removing the N-protecting group from the product obtained;

(h) detaching the product thus obtained from the solid support;

(i) cyclizing the product cleaved from the solid support;

(j) removing any protecting groups present on functional groups of any members of the chain of amino acid residues; and (k) if desired, converting the product thus obtained into a pharmaceutically acceptable salt or converting a pharmaceutically acceptable, or unacceptable, salt thus obtained into the corresponding free compound or into a different, pharmaceutically acceptable, salt.

As used in this description, the term "alkyl", taken alone or in combinations, designates saturated, straight-chain, branched or hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals having up to 8 carbon atoms. Thus, for example, the term "lower alkyl" designates saturated, straight-chain or branched hydrocarbon radicals having up to 8 carbon atoms, such as methyl, ethyl, n-propyl, isopropyl, n-butyl, sec.-butyl, isobutyl, tert.-butyl, and the like. Similarly, the term "lower cycloalkyl" designates saturated cyclic hydrocarbon radicals having up to 8 carbon atoms, such as cyclobutyl, cyclopentyl, cyclohexyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

Building blocks A1-A37 and A105 of the structural element —A—CO— belong to a class of amino acids wherein the N-terminus is a secondary amine forming part of a ring. Among the genetically encoded amino acids only proline falls into this class. The configuration of building block A1 through A37 and A105 is (D), and they can be combined with a building block —B—CO— of (L)-configuration. Preferred combinations are —$^D$A1—CO—$^L$B—CO— to —$^D$A37—CO—$^L$B—CO— and —$^D$A105—CO—$^L$B—CO—. Thus, for example, $^D$Pro-$^L$Pro constitutes the prototype of such a combination.

It will be appreciated that building blocks —A1—CO— to —A37—CO— and A105—CO— in which A has (D)-configuration, are carrying a group $R^1$ at the β-position to the N-terminus. The preferred values for $R^1$ are H and lower alkyl with the most preferred values for $R^1$ being H and methyl. It will be recognized by those skilled in the art, that A1-A37 and A105 are shown in (D)-configuration which, for $R^1$ being H and methyl, corresponds to the (R)-configuration. Depending on the priority of other values for $R^1$ according to the Cahn, Ingold and Prelog rules, this configuration may also have to be expressed as (S).

In addition to $R^1$ building blocks —A1—CO— to —A37—CO— and —A105—CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $(CH_2)_pOR^{55}$ (where $R^{55}$: H; lower alkyl; or lower alkenyl); $(CH_2)_pSR^{56}$ (where $R^{56}$: lower alkyl; or lower alkenyl); $(CH_2)_pNR^{33}R^{34}$ (where $R^{33}$: H; lower alkyl; or lower alkenyl; $R^{34}$: H; or lower alkyl; $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^3$: H; lower alkyl; lower alkenyl; —$(CH_2)_oOR^{55}$ (where $R^{55}$: H; lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); $(CH_2)_oPO(OR^{60})_2$ (where $R^{60}$: lower alkyl; or lower alkenyl); —$(CH_2)_sSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; —$(CH_2)_mOR^{55}$ (where $R^{55}$: H; lower alkyl; or lower alkenyl); —$(CH_2)_mSR^{56}$ (where $R^{56}$: lower alkyl; or lower alkenyl); —$(CH_2)_m NR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form:

—$(CH_2)_{2-6}$—; —$(CH_2)_2O(CH_2)_2$—; —$(CH_2)_2$ $S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_sSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^5$: lower alkyl; lower alkenyl; —$(CH_2)_oOR^{55}$ (where $R^{55}$: H; lower alkyl; or lower alkenyl); —$(CH_2)_pSR^{56}$ (where $R^{56}$: lower alkyl; or lower alkenyl); —$(CH_2)_oNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2$ $S(CH_2)_2$—; or —$(CH_2)_2NR^{57}(CH_2)_2$—; $R^{57}$: where H; or lower alkyl); $(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$—; where $R^{57}$: H; or lower alkyl); $(CH_2)_oN$ $(R^{20})COR^{64}$ (where: $R^{20}$: H; or lower alkyl; $R^{64}$: alkyl; alkenyl; aryl; and aryl-lower alkyl; heteroaryl-lower alkyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2$ $S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_pSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; —$(CH_2)_oOR^{55}$ (where $R^{55}$: H; lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2$ $S(CH_2)_2$—; or —$(CH_2)_2NR^{57}(CH_2)_2$— (where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$—; where $R^{57}$: H; or lower alkyl); —$(CH_2)_oN$ $(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2$ $S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^7$: lower alkyl; lower alkenyl; —$(CH_2)_qOR^{55}$ (where $R^{55}$: H; lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2$ $S(CH_2)_2$—; or —$(CH_2)_2NR^{57}(CH_2)_2$— (where $R^{57}$: H; or lower alkyl); $(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$— (where $R^{57}$: H; or lower alkyl); —$(CH_2)_qN$ $(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2$ $S(CH_2)_2$—; or —$(CH_2)_2NR^{57}(CH_2)_2$— (where $R^{57}$: H; or lower alkyl); —$(CH_2)_rPO(OR^{60})_2$ (where $R^{60}$: lower alkyl; or lower alkenyl); $(CH_2)_rSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; —$(CH_2)_oOR^{55}$ (where $R^{55}$: H; lower alkyl; or lower alkenyl); $(CH_2)_oSR^{56}$ (where $R^{56}$: lower alkyl; or lower alkenyl); —$(CH_2)_oNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$— (where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S$ $(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^9$: lower alkyl; lower alkenyl; —$(CH_2)_oOR^{55}$ (where $R^{55}$: H; lower alkyl; or lower alkenyl); —$(CH_2)_oSR^{56}$ (where $R^{56}$: lower alkyl; or lower alkenyl);

—$(CH_2)_oNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; —$(CH_2)_oOR^{55}$ (where $R^{55}$: H; lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; —$(CH_2)_mOR^{55}$ (where $R^{55}$: H; lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; —$(CH_2)_mOR^{55}$ (where $R^{55}$: H; lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_rPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{13}$: lower alkyl; lower alkenyl; —$(CH_2)_qOR^{55}$ (where $R^{55}$: H; lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COO$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{14}$: H; lower alkyl; lower alkenyl; —(CH$_2$)$_m$OR$^{55}$ (where R$^{55}$: H; lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: H; lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_m$N(R$^{20}$)COR$^{64}$ (where: R$^{20}$: H; lower alkyl; R$^{64}$: lower alkyl; or lower alkenyl); —(CH$_2$)$_q$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_q$PO(OR$^{60}$)$_2$ (where R$^{60}$: lower alkyl; or lower alkenyl); —(CH$_2$)$_q$SO$_2$R$^{62}$ (where R$^{62}$: lower alkyl; or lower alkenyl); —(CH$_2$)$_q$C$_6$H$_4$R$^8$ (where R$^8$: H; F; Cl; CF$_3$; lower alkyl; lower alkenyl; or lower alkoxy).

Among the building blocks A1 to A37 and A105 the following are preferred: A2 with R$^2$ being H; A5 with R$^2$ being H; A8; A13; A15; A22; A25; A32; and A105. Most preferred are building blocks of type A8':

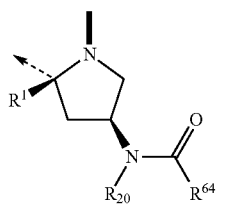

A8' wherein R$^{20}$ is H; or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl)benzyl (A8'-3); diphenylmethyl (A8'-4); 3-aminopropyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers* 1968, 6, 1425-1434; W. Kabsch, C. Sander, *Biopolymers* 1983, 22, 2577). Such building blocks are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α.α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— being an α-amino acid with L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, Helv. *Chim. Acta* 1995, 78, 563-580; D. Obrecht, H. Karajiannis, C. Lehmann, P. Schönholzer, C. Spiegler, *Helv. Chim. Acta* 1995, 78, 703-714).

Preferred values for R$^{20}$ in A70 to A104 are H; or lower alkyl; with methyl being most preferred. Preferred values for R$^{18}$, R$^{19}$ and R$^{21}$-R$^{29}$ in building blocks A70 to A104 are the following:

R$^{18}$: lower alkyl.

R$^{19}$: lower alkyl; lower alkenyl; —(CH$_2$)$_p$OR$^{55}$ (where R$^{55}$: H; lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: H; lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$PO(OR$^{60}$)$_2$ (where R$^{60}$: lower alkyl; or lower alkenyl); —(CH$_2$)$_p$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{21}$: H; lower alkyl; lower alkenyl; —(CH$_2$)$_o$OR$^{55}$ (where R$^{55}$: H; lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: H; lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$PO(OR$^{60}$)$_2$ (where R$^{60}$: lower alkyl; or lower alkenyl); (CH$_2$)$_o$SO$_2$R$^{62}$ (where R$^{62}$: lower alkyl; or lower alkenyl); or (CH$_2$)$_q$C$_6$H$_4$R$^8$ (where R$^8$: H; F; Cl; CF$_3$; lower alkyl; lower alkenyl; or lower alkoxy).

R$^{22}$: lower alkyl; lower alkenyl; —(CH$_2$)$_o$OR$^{55}$ (where R$^{55}$: H; lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: H; lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$(where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{23}$: H; lower alkyl; lower alkenyl; —(CH$_2$)$_o$OR$^{55}$ (where R$^{55}$: H; lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: H; lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are —(CH$_2$)$_o$NR$^{20}$COlower alkyl (R$^{20}$=H; or lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy);

R$^{24}$: lower alkyl; lower alkenyl; —(CH$_2$)$_o$OR$^{55}$ (where R$^{55}$: H; lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: H; lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are —(CH$_2$)$_o$NR$^{20}$COlower alkyl (R$^{20}$=H; or lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$— (where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where $R^8$: H; F; Cl; $CF_3$; lower alkyl; lower alkenyl; or lower alkoxy);

$R^{25}$: H; lower alkyl; lower alkenyl; —$(CH_2)_m OR^{55}$ (where $R^{55}$: H; lower alkyl; or lower alkenyl); —$(CH_2)_m NR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_m N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o PO(OR^{60})_2$ (where $R^{60}$: lower alkyl; or lower alkenyl); —$(CH_2)_o SO_2 R^{62}$ (where $R^{62}$: lower alkyl; or lower alkenyl); or —$(CH_2)_q C_6 H_4 R^8$ (where $R^8$: H; F; Cl; $CF_3$; lower alkyl; lower alkenyl; or lower alkoxy).

$R^{26}$: H; lower alkyl; lower alkenyl; —$(CH_2)_m OR^{55}$ (where $R^{55}$: H; lower alkyl; or lower alkenyl); —$(CH_2)_m NR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_m N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o PO(OR^{60})_2$ (where $R^{60}$: lower alkyl; or lower alkenyl); —$(CH_2)_o SO_2 R^{62}$ (where $R^{62}$: lower alkyl; or lower alkenyl); or —$(CH_2)_q C_6 H_4 R^8$ (where $R^8$: H; F; Cl; $CF_3$; lower alkyl; lower alkenyl; or lower alkoxy).

Alternatively, $R^{25}$ and $R^{26}$ taken together can be —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl).

$R^{27}$: H; lower alkyl; lower alkenyl; —$(CH_2)_o OR^{55}$ (where $R^{55}$: H; lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o PO(OR^{60})_2$ (where $R^{60}$: lower alkyl; or lower alkenyl); —$(CH_2)_o SO_2 R^{62}$ (where $R^{62}$: lower alkyl; or lower alkenyl); or —$(CH_2)_q C_6 H_4 R^8$ (where $R^8$: H; F; Cl; $CF_3$; lower alkyl; lower alkenyl; or lower alkoxy).

$R^{28}$: lower alkyl; lower alkenyl; —$(CH_2)_o OR^{55}$ (where $R^{55}$: H; lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$— (where $R^{57}$: H; or lower alkyl); —$(CH_2)_o PO(OR^{60})_2$ (where $R^{60}$: lower alkyl; or lower alkenyl); —$(CH_2)_o SO_2 R^{62}$ (where $R^{62}$: lower alkyl; or lower alkenyl); or —$(CH_2)_q C_6 H_4 R^8$ (where $R^8$: H; F; Cl; $CF_3$; lower alkyl; lower alkenyl; or lower alkoxy).

$R^{29}$: lower alkyl; lower alkenyl; —$(CH_2)_o OR^{55}$ (where $R^{55}$: H; lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: H; lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—

(where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are —$(CH_2)_oNR^{20}CO$lower-alkyl ($R^{20}$=H; or lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$— (where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

Among the building blocks A70 to A104 the following are preferred: A74 with $R^{22}$ being H; A75; A76; A77 with $R^{22}$ being H; A78; and A79.

The building block —B—CO— designates an L-amino acid residue. Preferred values for B are: —$NR^{20}CH(R^{71})$—; —$NR^{20}CH(R^{72})$; —$NR^{20}CH(R^{73})$—; —$NR^{20}CH(R^{74})$—; —$NR^{20}CH(R^{84})$—; or enantiomers of groups A2 with $R^2$ being H; A5 with $R^2$ being H; A8; A13; A15; A22; A25; A32; and A105. Most preferred building blocks —B—CO— are Ala L-Alanine
Arg L-Arginine
Asn L-Asparagine
Asp L-Aspartic acid
Gln L-Glutamine
Glu L-Glutamic acid
Gly Glycine
His L-Histidine
Ile L-Isoleucine
Leu L-Leucine
Lys L-Lysine
Met L-Methionine
Phe L-Phenylalanine
Pro L-Proline
Ser L-Serine
Thr L-Threonine
Trp L-Tryptophan
Tyr L-Tyrosine
Val L-Valine
Cit L-Citrulline
Orn L-Ornithine
tBuA L-t-Butylalanine
Sar Sarcosine
t-BuG L-tert.-Butylglycine
4AmPhe L-para-Aminophenylalanine
3AmPhe L-meta-Aminophenylalanine
2AmPhe L-ortho-Aminophenylalanine
Phe(mC(NH$_2$)=NH) L-meta-Amidinophenylalanine
Phe(pC(NH$_2$)=NH) L-para-Amidinophenylalanine
Phe(mNHC(NH$_2$)=NH) L-meta-Guanidinophenylalanine
Phe(pNHC(NH$_2$)=NH) L-para-Guanidinophenylalanine
Phg L-Phenylglycine
Cha L-Cyclohexylalanine
$C_4$al L-3-Cyclobutylalanine
$C_5$al L-3-Cyclopentylalanine
Nle L-Norleucine
2-Nal L-2-Naphthylalanine
1-Nal L-1-Naphthylalanine
4Cl-Phe L-4-Chlorophenylalanine
3Cl-Phe L-3-Chlorophenylalanine
2Cl-Phe L-2-Chlorophenylalanine
3,4Cl$_2$-Phe L-3,4-Dichlorophenylalanine
4F-Phe L-4-Fluorophenylalanine
3F-Phe L-3-Fluorophenylalanine
2F-Phe L-2-Fluorophenylalanine
Tic L-1,2,3,4-Tetrahydroisoquinoline-3-carboxylic acid
Thi L-β-2-Thienylalanine
Tza L-2-Thiazolylalanine
Mso L-Methionine sulfoxide
AcLys L-N-Acetyllysine
Dpr L-2,3-Diaminopropionic acid
A$_2$Bu L-2,4-Diaminobutyric acid
Dbu (2S, 3S)-2,3-Diaminobutyric acid
Abu L-α-Aminobutyric acid
Aha ε-Aminohexanoic acid
Aib α-Aminoisobutyric acid
Tyr(Bzl) L-O-Benzyltyrosine
Bip L-Biphenylalanine
Ser(Bzl) L-O-Benzylserine
Thr(Bzl) L-O-Benzylthreonine
hCha L-Homo-cyclohexylala nine
hSer L-Homo-serine
hSer(Me) L-Homo-O-methylserine
hArg L-Homo-arginine
hPhe L-Homo-phenylalanine
Bpa L-4-Benzoylphenylalanine
Azt L-Azetidine-2-carboxylic acid
Pip L-Pipecolic acid
OctG L-Octylglycine
MePhe L-N-Methylphenylalanine
MeNle L-N-Methylnorleucine
MeAla L-N-Methylalanine
MeIle L-N-Methylisoleucine
MeVal L-N-Methvaline
MeLeu L-N-Methylleucine
4Hyp1 (4S)-L-Hydroxyproline
4Hyp2 (4R)-L-Hydroxyproline
4Mp1 (4S)-L-Mercaptoproline
4Mp2 (4R)-L-Mercaptoproline
Oic (3aS, 7aS)-L-1-Octahydro-1H-indole-2-carboxylic acid
2Ind L-1H-indole-2-carboxylic acid In addition, the most preferred values for B also include groups of type A8" of (L)-configuration:

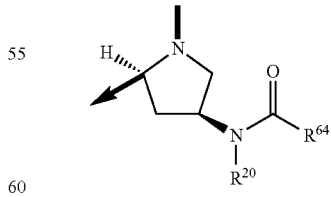

A8"

wherein $R^{20}$ is H; or lower alkyl; and $R^{64}$ is alkyl; alkenyl; —$[(CH_2)_u—X]_t—CH_3$ (where X is —O—; —$NR^{20}$—, or —S—; u=1-3, and t=1-6), aryl; aryl-lower alkyl; or heteroaryl-lower alkyl; especially those wherein $R^{64}$ is n-hexyl (A8"-21); n-heptyl (A8"-22); 4-(phenyl)benzyl (A8"-23); diphenylmethyl (A8"-24); 3-amino-propyl (A8"-25);

5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexyl-methyl (A8"-33); n-butyl (A8"-34); phenyl (A8"-35); benzyl (A8"-36); (3-indolyl) methyl (A8"-37); 2-(3-indolyl)ethyl (A8"-38); (4-phenyl)-phenyl (A8"-39); n-nonyl (A8"-40); $CH_3$—$OCH_2CH_2$—$OCH_2$-(A8"-41) and $CH_3$—$(OCH_2CH_2)_2$—$OCH_2$-(A8"-42).

Besides the structural element —B—CO— the β-hairpin peptidomimetics of the present invention can comprise the structural element —A—CO— and amino acid residues belonging to one of the following groups:

| Group C: | —$NR^{20}CH(R^{72})CO$—; | "hydrophobic: small to medium-sized" |
|---|---|---|
| Group D: | —$NR^{20}CH(R^{73})CO$—; | "hydrophobic: large aromatic or heteroaromatic" |
| Group E: | —$NR^{20}CH(R^{74})CO$—; | "polar-cationic" and "urea-derived" |
| Group F: | —$NR^{20}CH(R^{84})CO$—; | "polar-non-charged or anionic" |
| Group I: | —$NR^{88}CH_2CO$—; | "N-substituted glycine residue" |
| Group M: | —$NR^{20}CH(R^{73})(CH_2)_2CO$—; —$NR^{20}CH(R^{74})(CH_2)_2CO$—; or —$NR^{20}CH(R^{84})(CH_2)_2CO$—; | "$\gamma^4$-amino acids" |
| -Group N: | —$NR^{20}CH(R^{72})(CH_2)CO$—; —$NR^{20}CH(R^{73})(CH_2)CO$—; —$NR^{20}CH(R^{74})(CH_2)CO$—; or —$NR^{20}CH(R^{84})(CH_2)CO$—; | "$\beta^3$-amino acids" |
| Group O: | —$NR^{20}CH(R^{89})CO$—; | "dipeptidic amino acid residue based on a polar cationic side chain of group E" |
| Group P: | —$NR^{20}CH(R^{90})CO$—; | "dipeptidic amino acid residue based on an anionic side chain of group F" |
| Group Q: | —$NR^{20}CH(R^{91})CO$—; | "amino acid residue based on a polar cationic side chain of group E prolonged by an additional side chain with delimited length" |
| Group R: | —$NR^{20}CH(R^{92})CO$—; | "amino acid residue based on an anionic side chain of group F prolonged by an additional side chain with delimited length" |

Group C comprises amino acid residues with small to medium-sized aliphatic, hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates- and phosphates or tertiary amines. Genetically encoded small-to-medium-sized hydrophobic amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates and -phosphates or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tertiary amides, carboxylic acids and carboxylates, alkyl- or aryl phosphonates -and phosphates or tertiary amines. Genetically encoded polar-non-charged amino acids include asparagine, cysteine, glutamine, serine and threonine, but also aspartic acid and glutamic acid.

Group I comprises glycine having the amino group substituted by chains containing polar-cationic, polar-non-charged or anionic residues according to the general definition for substituent $R^{88}$. Polar-cationic refers to a basic side chain which is protonated at physiological pH. A polar-non-charged or anionic residue refers to a hydrophilic side chain that is uncharged and, respectively anionic at physiological pH (carboxylic acids being included), but that is not repelled by aqueous solutions.

Group M comprises $\gamma^4$-amino acid residues having both the amino group and the side chain attached to the γ-carbon atom; $\gamma^4$-amino acid residues with aromatic and heteroaromatic side chain groups according to the general definition for substituent $R^{73}$; $\gamma^4$-amino acid residues with polar-cationic, acylamino- and urea-derived side chain groups according to the general definition for substituent $R^{74}$; and $\gamma^4$-amino acid residues with polar-non-charged or anionic groups according to the general definition for substituent $R^{84}$. An aromatic side chain group is hydrophobic and contains at least one ring having a conjugated $\pi$-electron system (aromatic group). A heteroaromatic side chain group is hydrophobic and contains at least one ring having a conjugated $\pi$-system incorporating at least one heteroatom such as (but not limited to) O, S and N according to the general definition for substituent $R^{77}$. A polar-cationic side chain group refers to a basic side chain which is protonated at physiological pH. A polar-non-charged or anionic side chain group is uncharged and, respectively anionic at physiological pH (carboxylic acids being included), but is not repelled by aqueous solutions.

Group N comprises $\beta^3$-amino acid residues having both the amino group and the side chain attached to the $\beta$-carbon atom with side chain groups according to the general definition for substituent $R^{71}$; $\beta^3$-amino acid residues with small to medium-sized hydrophobic side chain groups according to the general definition for substituent $R^{72}$; $\beta^3$-amino acid residues with aromatic and heteroaromatic side chain groups according to the general definition for substituent $R^{73}$; $\beta^3$-amino acid residues with polar-cationic, acylamino- and urea-derived side chain groups according to the general definition for substituent $R^{74}$; and $\beta^3$-amino acid residues with polar-non-charged or anionic groups according to the general definition for substituent $R^{84}$. Hydrophobic side chain groups are uncharged at physiological pH and repelled by aqueous solution. An aromatic side chain group is hydrophobic and contains at least one ring having a conjugated $\pi$-electron system (aromatic group). A heteroaromatic side chain group is hydrophobic and contains at least one ring having a conjugated $\pi$-system incorporating at least one heteroatom such as (but not limited to) O, S and N according to the general definition for substituent $R^{77}$. A polar-cationic side chain group refers to a basic side chain which is protonated at physiological pH. A polar-non-charged or anionic side chain group is uncharged and, respectively anionic at physiological pH (carboxylic acids being included), but is not repelled by aqueous solutions.

Group O comprises amino acids containing side chains according to the general definition of $R^{89}$. These side chains are based on polar-cationic residues having terminal amino groups which are derivatized by formation of an amide bond with the $\alpha$-carboxylic group of a further amino acid of group C, D, E or F to finally generate a dipeptidic amino acid residue. The formation of such dipeptidic amino acid building blocks as well as their appropriate protection to be suitable for Fmoc-based SPPS is well known in the art.

Group P comprises amino acids containing side chains according to the general definition of $R^{90}$. These side chains are based on anionic residues having terminal carboxylic groups which are derivatized by formation of an amide bond with the $\alpha$-amino group of a further amino acid of group C, D, E or F to finally generate a dipeptidic amino acid residue. The formation of such dipeptidic amino acid building blocks as well as their appropriate protection to be suitable for Fmoc-based SPPS is well known in the art.

Group Q comprises amino acids containing side chains according to the general definition of $R^{91}$. These side chains are based on polar-cationic residues having terminal amino groups which are derivatized by formation of an amide bond with the carboxylic group of an organic carboxylic acid having a delimited length according to $R^{75}$. The formation of such amino acid building blocks as well as their appropriate protection to be suitable for Fmoc-based SPPS is well known in the art.

Group R comprises amino acids containing side chains according to the general definition of $R^{92}$. These side chains are based on anionic residues having terminal carboxylic groups which are derivatized by formation of an amide bond with the amino group of an organic amine having a delimited length according to $R^{75}$. The formation of such amino acid building blocks as well as their appropriate protection to be suitable for Fmoc-based SPPS is well known in the art.

Most preferred amino acid residues in cyclo(-Xaa$^1$-Xaa$^2$-Thr$^3$-Xaa$^4$-Ser$^5$-Xaa$^6$-Xaa$^7$-Xaa$^8$-Xaa$^9$-Xaa$^{10}$-Xaa$^{11}$-Xaa$^{12}$-Xaa$^{13}$-), are those derived from natural $\alpha$-, $\beta$- and $\gamma$-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| $^D$Ala | D-Alanine | $^D$A |
| Arg | L-Arginine | R |
| $^D$Arg | D-Arginine | $^D$R |
| Asn | L-Asparagine | N |
| $^D$Asn | D-Asparagine | $^D$N |
| Asp | L-Aspartic acid | D |
| $^D$Asp | D-Aspartic acid | $^D$D |
| Glu | L-Glutamic acid | E |
| $^D$Glu | D-Glutamic acid | $^D$E |
| Gln | L-Glutamine | Q |
| $^D$Gln | D-Glutamine | $^D$Q |
| Gly | Glycine | G |
| His | L-Histidine | H |
| $^D$His | D-Histidine | $^D$H |
| Ile | L-Isoleucine | I |
| $^D$Ile | D-Isoleucine | $^D$I |
| Leu | L-Leucine | L |
| $^D$Leu | D-Leucine | $^D$L |
| Lys | L-Lysine | K |
| $^D$Lys | D-Lysine | $^D$K |
| Met | L-Methionine | M |
| $^D$Met | D-Methionine | $^D$M |
| Phe | L-Phenylalanine | F |
| $^D$Phe | D-Phenylalanine | $^D$F |
| Pro | L-Proline | P |
| $^D$Pro | D-Proline | $^D$P |
| Ser | L-Serine | S |
| $^D$Ser | D-Serine | $^D$S |
| Thr | L-Threonine | T |
| $^D$Thr | D-Threonine | $^D$T |
| Trp | L-Tryptophan | W |
| $^D$Trp | D-Tryptophan | $^D$W |
| Tyr | L-Tyrosine | Y |
| $^D$Tyr | D-Tyrosine | $^D$Y |
| Val | L-Valine | V |
| $^D$Val | D-Valine | $^D$V |

H-$\beta^3$-HAla-OH (3S)-3-Amino-butyric acid
H-$\beta^3$-HVal-OH (3R)-3-Amino-4-methyl-valeric acid
H-$\beta^3$-HIle-OH (3R, 4S)-3-Amino-4-methyl-hexanoic acid
H-$\beta^3$-HLeu-OH (3S)-3-Amino-5-methyl-hexanoic acid
H-$\beta^3$-HMet-OH (3S)-3-Amino-5-methylthio-pentanoic acid
H-$\beta^3$-HTyr-OH (3S)-3-Amino-4-(4'-hydroxyphenyl)-butyric acid
H-$\beta^3$-HHis-OH (3S)-3-Amino-4-(imidazole-4'-yl)-butyric acid
H-$\beta^3$-HPhe-OH (3S)-3-Amino-4-phenyl-butyric acid
H-$\beta^3$-HTrp-OH (3S)-3-Amino-4-(indol-3'-yl)-butyric acid
H-$\beta^3$-HSer-OH (3R)-3-Amino-4-hydroxy-butyric acid
H-$\beta^3$-HAsp-OH 3-Amino-pentanedioic acid
H-$\beta^3$-HGlu-OH (3S)-3-Amino-hexanedioic acid
H-$\beta^3$-HLys-OH (3S)-3,7-Diamino-heptanoic acid
H-$\beta^3$-HArg-OH (3S)-3-Amino-6-guanidino-hexanoic-acid
H-$\beta^3$-HCys-OH (3R)-3-Amino-4-mercapto-butyric acid H-β³-HAsn-OH (3S)-3-Amino-4-carbamoyl-butyric acid
H-β³-HGln-OH (3S)-3-Amino-5-carbamoyl-pentanoic acid
H-β³-HThr-OH (3R, 4R)-3-Amino-4-hydroxy-pentanoic acid
H-γ⁴-DiHTyr-OH (4R)-4-Amino-5-(4'-hydroxyphenyl)-pentanoic acid
H-γ⁴-DiHHis-OH (4R)-4-Amino-5-(imidazole-4'-yl)-pentanoic acid
H-γ⁴-DiHPhe-OH (4R)-4-Amino-5-phenyl-pentanoic acid
H-γ⁴-DiHTrp-OH (4R)-4-Amino-5-(indol-3'-yl)-pentanoic acid
H-γ⁴-DiHSer-OH (4R)-4-Amino-5-hydroxy-pentanoic acid
H-γ⁴-DiHAsp-OH (4R)-4-Amino-hexanedioic acid
H-γ⁴-DiHGlu-OH 4-Amino-heptanedioic acid
H-γ⁴-DiHLys-OH (4S)-4,8-Diamino-octanoic acid
H-γ⁴-DiHArg-OH (4S)-4-Amino-7-guanidino-heptanoic-acid
H-γ⁴-DiHCys-OH (4R)-4-Amino-5-mercapto-pentanoic acid
H-γ⁴-DiHAsn-OH (4R)-4-Amino-5-carbamoyl-pentanoic acid
H-γ⁴-DiHGln-OH (4S)-4-Amino-6-carbamoyl-hexanoic acid
H-γ⁴-DiHThr-OH (4R, 5R)-4-Amino-5-hydroxy-hexanoic acid Other α-, β- and γ-amino acids which, or the residues of which, are suitable for the purposes of the present invention include:

AllylGly L-Allylglycine
OctGly L-Octylglycine
Ala(CF₃) L-Trifluoroalanine
Cit L-Citrulline
$^D$Cit D-Citrulline
Orn L-Ornithine
$^D$Orn D-Ornithine
tBuA L-t-Butylalanine
$^D$tBuA D-t-Butylalanine
Sar Sarcosine
Pen L-Penicillamine
$^D$Pen D-Penicillamine
tBuG L-tert.-Butylglycine
$^D$tBuG D-tert.-Butylglycine
4AmPhe L-para-Aminophenylalanine
$^D$4AmPhe D-para-Aminophenylalanine
3AmPhe L-meta-Aminophenylalanine
$^D$3AmPhe D-meta-Aminophenylalanine
2AmPhe L-ortho-Aminophenylalanine
$^D$2AmPhe D-ortho-Aminophenylalanine
Phe(mC(NH₂)=NH) L-meta-Amidinophenylalanine
$^D$Phe(mC(NH₂)=NH) D-meta-Amidinophenylalanine
Phe(pC(NH₂)=NH) L-para-Amidinophenylalanine
$^D$Phe(pC(NH₂)=NH) D-para-Amidinophenylalanine
Phe(mNHC(NH₂)=NH) L-meta-Guanidinophenylalanine
$^D$Phe(mNHC(NH₂)=NH) D-meta-Guanidinophenylalanine
Phe(pNHC(NH₂)=NH) L-para-Guanidinophenylalanine
$^D$Phe(pNHC(NH₂)=NH) D-para-Guanidinophenylalanine
2Pal (2S)-2-Amino-3-(pyridine-2'-yl)-propionic acid
$^D$2Pal (2R)-2-Amino-3-(pyridine-2'-yl)-propionic acid
4Pal (2S)-2-Amino-3-(pyridine-4'-yl)-propionic acid
$^D$4Pal (2R)-2-Amino-3-(pyridine-4'-yl)-propionic acid
Phg L-Phenylglycine
$^D$Phg D-Phenylglycine
Cha L-Cyclohexylalanine
$^D$Cha D-Cyclohexylalanine
C₄al L-3-Cyclobutylalanine
$^D$C₄al D-3-Cyclobutylalanine
C₅al L-3-Cyclopentylalanine
$^D$C₅al D-3-Cyclopentylalanine
Nle L-Norleucine
$^D$Nle D-Norleucine
2-Nal L-2-Naphthylalanine
$^D$2Nal D-2-Naphthylalanine
1-Nal L-1-Naphthylalanine
$^D$1Nal D-1-Naphthylalanine
4ClPhe L-4-Chlorophenylalanine
$^D$4ClPhe D-4-Chlorophenylalanine
3ClPhe L-3-Chlorophenylalanine
$^D$3ClPhe D-3-Chlorophenylalanine
2ClPhe L-2-Chlorophenylalanine
$^D$2ClPhe D-2-Chlorophenylalanine
3,4Cl₂Phe L-3,4-Dichlorophenylalanine
$^D$3,4Cl₂Phe D-3,4-Dichlorophenylalanine
4FPhe L-4-Fluorophenylalanine
$^D$4FPhe D-4-Fluorophenylalanine
3FPhe L-3-Fluorophenylalanine
$^D$3FPhe D-3-Fluorophenylalanine
2FPhe L-2-Fluorophenylalanine
$^D$2FPhe D-2-Fluorophenylalanine
Thi L-β-2-Thienylalanine
$^D$Thi D-β-2-Thienylalanine
Tza L-2-Thiazolylalanine
$^D$Tza D-2-Thiazolylalanine
Mso L-Methionine sulfoxide
$^D$Mso D-Methionine sulfoxide
AcLys N-Acetyllysine
$^D$AcLys N-Acetyl-D-lysine
Dap L-2,3-Diaminopropionic acid
$^D$Dap D-2,3-Diaminopropionic acid
Dpr 2,3-Diaminopropionic acid
$^D$Dpr D-2,3-Diaminopropionic acid
Dab L-2,4-Diaminobutyric acid
$^D$Dab D-2,4-Diaminobutyric acid
Dbu (2S)-2,3-Diamino-butyric acid
$^D$Dbu (2R)-2,3-Diamino-butyric acid
Abu L-α-Aminobutyric acid
Aha ε-Aminohexanoic acid
Aib α-Aminoisobutyric acid
Cyp 1-Amino cyclopentane carboxylic acid
Tyr(Bzl) L-O-Benzyltyrosine
$^D$Tyr(Bzl) D-O-Benzyltyrosine
His(Bzl) (3S)-2-Amino-3-(1'-benzylimidazole-4'-yl)-propionic acid
$^D$His(Bzl) (3R)-2-Amino-3-(1'-benzylimidazole-4'-yl)-propionic acid
Bip L-(4-phenyl)phenylalanine
DBip D-(4-phenyl)phenylalanine
Ser(Bzl) L-O-Benzylserine
$^D$Ser(Bzl) D-O-Benzylserine
Thr(Bzl) L-O-Benzylthreonine
$^D$Thr(Bzl) D-O-Benzylthreonine
alloThr (2S, 3S)-2-Amino-3-hydroxy-butyric acid
$^D$alloThr (2R, 3S)-2-Amino-3-hydroxy-butyric acid
Leu3OH (2S, 3R)-2-Amino-3-hydroxy-4-methyl-pentanoic acid
$^D$Leu3OH (2R, 3R)-2-Amino-3-hydroxy-4-methyl-pentanoic acid
hAla L-Homo-alanine
$^D$hAla D-Homo-alanine
hArg L-Homo-arginine
$^D$hArg D-Homo-arginine
hCys L-Homo-cysteine
$^D$hcys D-Homo-cysteine
hGlu L-Homo-glutamic acid
$^D$hGlu D-glutamic acid hGln L-Homo-glutamine
$^D$hGln D-Homo-glutamine
hHis L-Homo-histidine
$^D$hHis D-Homo-histidine
hIle L-Homo-isoleucine
$^D$hIle D-Homo-isoleucine
hLeu L-Homo-leucine
$^D$hLeu D-Homo-leucine
hNle L-Homo-norleucine
$^D$hNle D-Homo-norleucine
hLys L-Homo-lysine
$^D$hLYS D-Homo-lysine
hMet L-Homo-Methionine
$^D$hMet D-Homo-Methionine
hPhe L-Homo-phenylalanine
DiHPhe L-Dihomo-phenylalanine, (2S)-2-amino-5-phenyl-pentanoic acid
$^D$hPhe D-Homo-phenylalanine
hSer L-Homo-serine
$^D$hSer D-Homo-serine
hSer(Me) L-Homo-O-methylserine
$^D$hSer(Me) D-Homo-O-methylserine
hThr L-Homo-threonine
$^D$hThr D-Homo-threonine
hTrp L-Homo-tryptophan
$^D$hTrp D-Homo-tryptophan
hTyr L-Homo-tyrosine
$^D$hTyr D-Homo-tyrosine
hVal L-Homo-valine
$^D$hVal D-Homo-valine
hCha L-Homo-cyclohexylalanine
$^D$hCha D-Homo-cyclohexylalanine
Bpa L-4-Benzoylphenylalanine
$^D$Bpa D-4-Benzoylphenylalanine
OctG L-Octylglycine
$^D$OctG D-Octylglycine
Tic (3S)-1,2,3,4-Tetrahydroisoquinoline-3-carboxylic acid
$^D$Tic (3R)-1,2,3,4-Tetrahydroisoquinoline-3-carboxylic acid
Tiq (1S)-1,2,3,4-Tetrahydroisoquinoline-1-carboxylic acid
$^D$Tiq (1R)-1,2,3,4-Tetrahydroisoquinoline-1-carboxylic acid
Oic (2S, 3aS, 7aS)-1-Octahydro-1H-indole-2-carboxylic acid
$^D$Oic (2R, 3aS, 7aS)-1-Octahydro-1H-indole-2-carboxylic acid
2Ind L-2,3-dihydro-1H-indole-2-carboxylic acid
$^D$2Ind D-2,3-dihydro-1H-indole-2-carboxylic acid
4AmPyrr1 (2S, 4S)-4-Amino-pyrrolidine-2-carboxylic acid
$^D$4AmPyrr1 (2R, 4S)-4-Amino-pyrrolidine-2-carboxylic acid
4AmPyrr2 (2S, 4R)-4-Amino-pyrrolidine-2-carboxylic acid
$^D$4AmPyrr2 (2R, 4R)-4-Amino-pyrrolidine-2-carboxylic acid
4PhePyrr1 (2S, 4R)-4-Phenyl-pyrrolidine-2-carboxylic acid
$^D$4PhePyrr1 (2R, 4R)-4-Phenyl-pyrrolidine-2-carboxylic acid
4PhePyrr2 (2S, 4S)-4-Phenyl-pyrrolidine-2-carboxylic acid
$^D$4PhePyrr2 (2R, 4S)-4-Phenyl-pyrrolidine-2-carboxylic acid
5PhePyrr1 (2S, 5R)-5-Phenyl-pyrrolidine-2-carboxylic acid
$^D$5PhePyrr1 (2R, 5R)-5-Phenyl-pyrrolidine-2-carboxylic acid
5PhePyrr2 (2S, 5S)-5-Phenyl-pyrrolidine-2-carboxylic acid
$^D$5PhePyrr2 (2R, 5S)-5-Phenyl-pyrrolidine-2-carboxylic acid
4Hyp1 (4S)-L-Hydroxyproline
$^D$4Hyp1 (4S)-D-Hydroxyproline
4Hyp2 (4R)-L-Hydroxyproline
$^D$4Hyp2 (4R)-D-Hydroxyproline
4Mp1(4S)-L-Mercaptoproline
$^D$4Mp1 (4S)-D-Mercaptoproline
4Mp2 (4R)-L-Mercaptoproline
$^D$4Mp2 (4R)-D-Mercaptoproline
Azt L-Azetidine-2-carboxylic acid
$^D$Azt D-Azetidine-2-carboxylic acid
Pip L-Pipecolic acid
$^D$Pip D-Pipecolic acid
H-$\beta^3$-HCit-OH (3S)-3-Amino-6-carbamidyl-hexanoic acid
H-$\beta^3$-HOrn-OH (3S)-3,6-Diamino-hexanoic acid
H-$\beta^3$-HtBuA-OH (3S)-3-Amino-5,5-dimethyl-hexanoic acid
H-$\beta^3$-HSar-OH N-Methyl-3-amino-propionic acid
H-$\beta^3$-HPen-OH (3R)-3-Amino-4-methyl-4-mercapto-pentanoic acid
H-$\beta^3$-HtBuG-OH (3R)-3-Amino-4,4-dimethyl-pentanoic acid
H-3-H4AmPhe-OH (3S)-3-Amino-4-(4'-aminophenyl)-butyric acid
H-3-H3AmPhe-OH (3S)-3-Amino-4-(3'-aminophenyl)-butyric acid
H-3-H2AmPhe-OH (3S)-3-Amino-4-(2'-aminophenyl)-butyric acid
H-$\beta^3$-HPhe(mC(NH$_2$)=NH)—OH (3S)-3-Amino-4-(3'-amidinophenyl)-butyric acid
H-$\beta^3$-HPhe(pC(NH$_2$)=NH)—OH (3S)-3-Amino-4-(4'-amidinophenyl)-butyric acid
H-3-HPhe(mNHC(NH$_2$)=NH)—OH (3S)-3-Amino-4-(3'-guanidinophenyl)-butyric acid
H-3-HPhe(pNHC(NH$_2$)=NH)—OH (3S)-3-Amino-4-(4'-guanidinophenyl)-butyric acid
H-$\beta^3$-H2Pal-OH (3S)-3-Amino-4-(pyridine-2'-yl)-butyric acid
H-$\beta^3$-H4Pal-OH (3S)-3-Amino-4-(pyridine-4'-yl)-butyric acid
H-$\beta^3$-HPhg-OH (3R)-3-Amino-3-phenyl-propionic acid
H-$\beta^3$-HCha-OH (3S)-3-Amino-4-cyclohexyl-butyric acid
H-$\beta^3$-HC$_4$al-OH (3S)-3-Amino-4-cyclobutyl-butyric acid
H-$\beta^3$-HC$_5$al-OH (3S)-3-Amino-4-cyclopentyl-butyric acid
H-$\beta^3$-HNle-OH (3S)-3-Amino-heptanoic acid
H-$\beta^3$-H2Nal-OH (3S)-3-Amino-4-(2'-naphthyl)-butyric acid
H-$\beta^3$-H1Nal-OH (3S)-3-Amino-4-(1'-naphthyl)-butyric acid
H-$\beta^3$-H4ClPhe-OH (3S)-3-Amino-4-(4'-chlorophenyl)-butyric acid
H-$\beta^3$-H3ClPhe-OH (3S)-3-Amino-4-(3'-chlorophenyl)-butyric acid
H-$\beta^3$-H2ClPhe-OH (3S)-3-Amino-4-(2'-chlorophenyl)-butyric acid
H-$\beta^3$-H3,4Cl$_2$Phe-OH (3S)-3-Amino-4-(3',4'-dichlorophenyl)-butyric acid
H-$\beta^3$-H4FPhe-OH (3S)-3-Amino-4-(4'-fluorophenyl)-butyric acid
H-$\beta^3$-H3FPhe-OH (3S)-3-Amino-4-(3'-fluorophenyl)-butyric acid
H-$\beta^3$-H2FPhe-OH (3S)-3-Amino-4-(2'-fluorophenyl)-butyric acid
H-$\beta^3$-HThi-OH (3R)-3-Amino-4-(2'-thienyl)-butyric acid
H-$\beta^3$-HTza-OH (3R)-3-Amino-4-(2'-thiazolyl)-butyric acid
H-$\beta^3$-HMso-OH (3R)-3-Amino-4-methylsulfoxyl-butyric acid
H-$\beta^3$-HAcLys-OH (3S)-7-Acetylamino-3-amino-heptanoic acid
H-$\beta^3$-HDpr-OH (3R)-3,4-diamino-butyric acid
H-$\beta^3$-HA$_2$Bu-OH (3S)-3,5-Diamino-pentanoic acid H-β³-HDbu-OH (3R)-3,4-Diamino-pentanoic acid
H-β³-HAib-OH Amino-dimethyl-acetic acid
H-β³-HCyp-OH 1-Amino-cyclopentane-1-yl-acetic acid
H-β³-HY(Bzl)-OH (3S)-3-Amino-4-(4'-benzyloxyphenyl)-butyric acid
H-β³-HH(Bzl)-OH (3S)-3-Amino-4-(1'-benzylimidazole-4'-yl)-butyric acid
H-β³-HBip-OH (3S)-3-Amino-4-biphenylyl-butyric acid
H-β³-HS(Bzl)-OH (3S)-3-Amino-4-(benzyloxy)-butyric acid
H-β³-HT(Bzl)-OH (3R, 4R)-3-Amino-4-benzyloxy-pentanoic acid
H-β³-HalloT-OH (3R, 4S)-3-Amino-4-hydroxy-pentanoic acid
H-β³-HLeu3OH—OH (3R, 4R)-3-Amino-4-hydroxy-5-methyl-hexanoic acid
H-β³-HhAla-OH (3S)-3-Amino-pentanoic acid
H-β³-HhArg-OH (3S)-3-Amino-7-guanidino-heptanoic acid
H-β³-HhCys-OH (3R)-Amino-5-mercapto-pentanoic acid
H-β³-HhGlu-OH (3S)-3-Amino-heptanedioic acid
H-β³-HhGln-OH (3S)-3-Amino-6-carbamoyl-hexanoic acid
H-β³-HhHis-OH (3S)-3-Amino-5-(imidazole-4'-yl)-pentanoic acid
H-β³-HhIle-OH (3S, 5S)-3-Amino-5-methyl-heptanoic acid
H-β³-HhLeu-OH (3S)-3-Amino-6-methyl-heptanoic acid
H-β³-HhNle-OH (3S)-3-Amino-octanoic acid
H-β³-DiAoc-OH (3S)-3,8-Diamino-octanoic acid
H-β³-HhMet-OH (3S)-3-Amino-6-methylthio-hexanoic acid
H-β³-HhPe-OH (3S)-3-Amino-5-phenyl-pentanoic acid
H-β³-HhSer-OH (3S)-3-Amino-5-hydroxy-pentanoic acid
H-β³-HhThr-OH (3S, 5R)-3-Amino-5-hydroxy-hexanoic acid
H-β³-HhTrp-OH (3S)-3-Amino-5-(indol-3'-yl)-pentanoic acid
H-β³-HhThr-OH (3S)-3-Amino-5-(4'-hydroxyphenyl)-pentanoic acid
H-β³-HhCha-OH (3S)-3-Amino-5-cyclohexyl-pentanoic acid
H-β³-HBpa-OH (3S)-3-Amino-4-(4'-benzoylphenyl)-butyric acid
H-β³-HOctG-OH (3S)-3-Amino-undecanoic acid
H-β³-HNle-OH (3S)-3-Amino-heptanoic acid
H-β³-HTic-OH (3S)-1,2,3,4-Tetrahydroisoquinoline-3-yl-acetic acid
H-β³-HTiq-OH (1S)-1,2,3,4-Tetrahydroisoquinoline-1-acetic acid
H-β³-HOic-OH (2S, 3aS, 7aS)-1-Octahydro-1H-indole-2-yl-acetic acid
H-β³-H4AmPyrr1-OH (2S, 4S)-4-Amino-pyrrolidine-2-acetic acid
H-β³-H4AmPyrr2-OH (2S, 4R)-4-Amino-pyrrolidine-2-acetic acid
H-β³-H4PhePyrr1-OH (2S, 4R)-4-Phenyl-pyrrolidine-2-acetic acid
H-β³-H4PhePyrr2-OH (2S, 4S)-4-Phenyl-pyrrolidine-2-acetic acid
H-β³-H5PhePyrr1-OH (2S, 5R)-5-Phenyl-pyrrolidine-2-acetic acid
H-β³-H5PhePyrr2-OH (2S, 5S)-5-Phenyl-pyrrolidine-2-acetic acid
H-β³-H4Hyp1-OH (2S, 4S)-4-Hydroxy-pyrrolidine-2-acetic acid
H-β³-H4Hyp2-OH (2S, 4R)-4-Hydroxy-pyrrolidine-2-acetic acid
H-β³-H4Mp1-OH (2R, 4S)-4-Mercapto-pyrrolidine-2-acetic acid
H-β³-H4Mp2-OH (2R, 4R)-4-Mercapto-pyrrolidine-2-acetic acid
H-β³-HPip-OH (2S)-piperidine-2-acetic acid
H-β³-HPro-OH (2S)-pyrrolidine-2-acetic acid
H-β³-H$^D$Pro-OH (2R)-pyrrolidine-2-acetic acid
H-γ⁴-DiHCit-OH (4S)-4-Amino-7-carbamidyl-heptanoic acid
H-γ⁴-DiHOrn-OH (4S)-4,7-Diamino-heptanoic acid
H-γ⁴-DiH4AmPhe-OH (4R)-4-Amino-5-(4'-aminophenyl)-pentanoic acid
H-γ⁴-DiH3AmPhe-OH (4R)-4-Amino-5-(3'-aminophenyl)-pentanoic acid
H-γ⁴-DiH2AmPhe-OH (4R)-4-Amino-5-(2'-aminophenyl)-pentanoic acid
H-γ⁴-DiHPhe(mC(NH₂)=NH)—OH (4R)-4-Amino-5-(3'-amidinophenyl)-pentanoic acid
H-γ⁴-DiHPhe(pC(NH₂)=NH)—OH (4R)-4-Amino-5-(4'-amidinophenyl)-pentanoic acid
H-γ⁴-DiHPhe(mNHC(NH₂)=NH)—OH (4R)-4-Amino-5-(3'-guanidino-phenyl)-pentanoic acid
H-γ⁴-DiHPhe(pNHC(NH₂)=NH)—OH (4R)-4-Amino-5-(4'-guanidino-phenyl)-pentanoic acid
H-γ⁴-DiH2Pal-OH (4R)-4-Amino-5-(pyridine-4'-yl)-pentanoic acid
H-γ⁴-DiH4Pal-OH (4R)-4-Amino-5-(pyridine-4'-yl)-pentanoic acid
H-γ⁴-DiHPhg-OH (4R)-4-Amino-4-phenyl-butyric acid
H-γ⁴-DiH2Nal-OH (4S)-4-Amino-5-(2'-naphthyl)-pentanoic acid
H-γ⁴-DiH1Nal-OH (4S)-4-Amino-5-(1'-naphthyl)-pentanoic acid
H-γ⁴-DiH4ClPhe-OH (4R)-4-Amino-5-(4'-chlorophenyl)-pentanoic acid
H-γ⁴-DiH3ClPhe-OH (4R)-4-Amino-5-(3'-chlorophenyl)-pentanoic acid
H-γ⁴-DiH2ClPhe-OH (4R)-4-Amino-5-(2'-chlorophenyl)-pentanoic acid
H-γ⁴-DiH3,4Cl₂Phe-OH (4R)-4-Amino-5-(3',4'-dichlorophenyl)-pentanoic acid
H-γ⁴-DiH4FPhe-OH (4R)-4-Amino-5-(4'-fluorophenyl)-pentanoic acid
H-γ⁴-DiH3FPhe-OH (4R)-4-Amino-5-(3'-fluorophenyl)-pentanoic acid
H-γ⁴-DiH2FPhe-OH (4R)-4-Amino-5-(2'-fluorophenyl)-pentanoic acid
H-γ⁴-DiHThi-OH (4R)-4-Amino-5-(2'-thienyl)-pentanoic acid
H-γ⁴-DiHTza-OH (4R)-4-Amino-5-(2'-thiazolyl)-pentanoic acid
H-γ⁴-DiHMso-OH (4R)-4-Amino-5-methylsulfoxyl-pentanoic acid
H-γ⁴-DiHAcLys-OH (4S)-8-Acetylamino-4-amino-ocatanoic acid
H-γ⁴-DiHDpr-OH (4R)-4,5-diamino-pentanoic acid
H-γ⁴-DiHA₂Bu-OH (4R)-4,5-Diamino-hexanoic acid
H-γ⁴-DiHDbu-OH (4R)-4,5-Diamino-hexanoic acid
H-γ⁴-DiHAib-OH 3-Amino-3,3-dimethyl-propionic acid
H-γ⁴-DiHY(Bzl)-OH (4R)-4-Amino-5-(4'-benzyloxyphenyl)-pentanoic acid
H-γ⁴-DiHH(Bzl)-OH (4R)-4-Amino-5-(1'-benzylimidazole-4'-yl)-pentanoic acid
H-γ⁴-DiHBip-OH (4R)-4-Amino-5-biphenylyl-pentanoic acid
H-γ⁴-DiHS(Bzl)-OH (4S)-4-Amino-5-(benzyloxy)-pentanoic acid
H-γ⁴-DiHT(Bzl)-OH (4R, 5R)-4-Amino-5-benzyloxy-hexanoic acid H-γ⁴-DiHalloT-OH (4R, 5S)-4-Amino-5-hydroxy-hexanoic acid
H-γ⁴-DiHLeu3OH—OH (4R, 5R)-4-Amino-5-hydroxy-6-methyl-heptanoic acid
H-γ⁴-DiHhArg-OH (4S)-4-Amino-8-guanidino-octanoic acid
H-γ⁴-DiHhGlu-OH (4S)-4-Amino-octanedioic acid
H-γ⁴-DiHhGln-OH (4S)-4-Amino-7-carbamoyl-heptanoic acid
H-γ⁴-DiHhHis-OH (4S)-4-Amino-6-(imidazole-4'-yl)-hexanoic acid
H-γ⁴-DiHhLys-OH (4S)-4,9-Diamino-nonanoic acid
H-γ⁴-DiHhPhe-OH (4S)-4-Amino-6-phenyl-hexanoic acid
H-γ⁴-DiHhSer-OH (4R)-4-Amino-6-hydroxy-hexanoic acid
H-γ⁴-DiHhThr-OH (4R, 6R)-4-Amino-6-hydroxy-heptanoic acid
H-γ⁴-DiHhTrp-OH (4S)-4-Amino-6-(indol-3'-yl)-hexanoic acid
H-γ⁴-DiHhTyr-OH (4S)-4-Amino-6-(4'-hydroxyphenyl)-hexanoic acid
H-γ⁴-DihBpa-OH (4R)-4-Amino-5-(4'-benzoylphenyl)-pentanoic acid
H-γ⁴-DiHTic-OH (3R)-1',2',3',4'-Tetrahydroisoquinoline-3'-yl-3-propionic acid
H-γ⁴-DiHTiq-OH (1'R)-1',2',3',4'-Tetrahydroisoquinoline-1'-yl-3-propionic acid
H-γ⁴-DiHOic-OH (2'S, 3'aS, 7'aS)-1'-Octahydro-1H-indole-2'-yl-3-propionic acid
H-γ⁴-DiH4AmPyrr1-OH (2'R, 4'S)-4'-Amino-pyrrolidine-2'-yl-3-propionic acid
H-γ⁴-DiH4AmPyrr2-OH (2'R, 4'R)-4'-Amino-pyrrolidine-2'-yl-3-propionic acid
H-γ⁴-DiH4PhePyrr1-OH (2'R, 4'R)-4'-Phenyl-pyrrolidine-2'-yl-3-propionic acid
H-γ⁴-DiH4PhePyrr2-OH (2'R, 4'S)-4'-Phenyl-pyrrolidine-2'-yl-3-propionic acid
H-γ⁴-DiH5PhePyrr1-OH (2'S, 5'R)-5'-Phenyl-pyrrolidine-2'-yl-3-propionic acid
H-γ⁴-DiH5PhePyrr2-OH (2'S, 5'S)-5'-Phenyl-pyrrolidine-2'-yl-3-propionic acid
H-γ⁴-DiH4Hyp1-OH (2'R, 4'S)-4'-Hydroxy-pyrrolidine-2'-yl-2-propionic acid
H-γ⁴-DiH4Hyp2-OH (2'R, 4'R)-4'-Hydroxy-pyrrolidine-2'-yl-3-propionic acid
H-γ⁴-DiH4Mp1-OH (2'R, 4'S)-4'-Mercapto-pyrrolidine-2'-yl-3-propionic acid
H-γ⁴-DiH4Mp2-OH (2'R, 4'R)-4'-Mercapto-pyrrolidine-2'-yl-3-propionic acid
H-γ⁴-DiHPip-OH (2'S)-Piperidine-2'-yl-3-propionic acid
H-γ⁴-DiHPro-OH (2'S)-Pyrrolidine-2'-yl-3-propionic acid
H-γ⁴-DiH$^D$Pro-OH (2'R)-Pyrrolidine-2'-yl-3-propionic acid
(AEt)G N-(2-Aminoethyl)glycine
(APr)G N-(3-Amino-n-propyl)glycine
(ABu)G, Nglu N-(4-Amino-n-butyl)glycine
(APe)G N-(5-Amino-n-pentyl)glycine
(GuEt)G N-(2-Guanidinoethyl)glycine
(GuPr)G N-(3-Guanidino-n-propyl)glycine
(GuBu)G N-(4-Guanidino-n-butyl)glycine
(GuPe)G N-(5-Guanidino-n-pentyl)glycine
(CboMe)G N-(Carboxymethyl)glycine
(CboEt)G, Nglu N-(2-Carboxyethyl)glycine
(CboPr)G N-(3-Carboxypropyl)glycine
(CbaMe)G N-(Carbamoylmethyl)glycine
(CbaEt)G N-(2-Carbamoylethyl)glycine
(CbaPr)G N-(3-Carbamoylpropyl)glycine
(HyEt)G N-(2-Hydroxyethyl)glycine
(HyPr)G (2R)—N-(2-Hydroxypropyl)glycine
(Mcet)G N-(2-Mercaptoethyl)glycine
NMeAla L-N-Methylalanine
NMe$^D$Ala D-N-Methylalanine
NMeVal L-N-Methylvaline
NMe$^D$Val D-N-Methylvaline
NMeIle L-N-Methylisoleucine
NMe$^D$Ile D-N-Methylisoleucine
NMeLeu L-N-Methylleucine
NMe$^D$Leu D-N-Methylleucine
NMeNle L-N-Methylnorleucine
NMe$^D$Nle D-N-Methylnorleucine
NMeMet L-N-Methylmethionine
NMe$^D$Met D-N-Methylmethionine
NMeTyr L-N-Methyltyrosine
NMe$^D$Tyr D-N-Methyltyrosine
NMeHis L-N-Methylhistidine
NMe$^D$His D-N-Methylhistidine
NMePhe L-N-Methylphenylalanine
NMe$^D$Phe D-N-Methylphenylalanine
NMeTrp L-N-Methyltryptophane
NMe$^D$Trp D-N-Methyltryptophane
NMeSer L-N-Methylserine
NMe$^D$Ser D-N-Methylserine
NMeAsp L-N-Methylaspartic acid
NMe$^D$Asp D-N-Methylaspartic acid
NMeGlu L-N-Methylglutamic acid
NMe$^D$Glu D-N-Methylglutamic acid
NMeLys L-N-Methyllysine
NMe$^D$Lys D-N-Methyllysine
NMeArg L-N-Methylarginine
NMe$^D$Arg D-N-Methylarginine
NMe$^D$ab L-N-Methyl-2,4-diamino butyric acid
NMe$^D$Dab D-N-Methyl-2,4-diamino butyric acid
NMeCys L-N-Methylcysteine
NMe$^D$Cys D-N-Methylcysteine
NMeAsn L-N-Methylasparagine
NMe$^D$Asn D-N-Methylasparagine
NMeGln L-N-Methylglutamine
NMe$^D$Gln D-N-Methylglutamine
NMeThr L-N-Methylthreonine
NMe$^D$Thr D-N-Methylthreonine
Dap(Phe) (2S)-2-Amino-3-((2S)-2-amino-3-phenyl)-propanamido)-propanoic acid
Dap(Tyr) (2S)-2-Amino-3-((2S)-2-amino-(4-hydroxyphenyl)-propanamido)-propanoic acid
Dap(His) (2S)-2-Amino-3-((2S)-2-amino-(1H-imidazol-5-yl)-propanamido)-propanoic acid
Dap(Trp) (2S)-2-Amino-3-((2S)-2-amino-(1H-indol-3-yl)-propanamido)-propanoic acid
Dab(Phe) (2S)-2-Amino-4-((2S)-2-amino-3-phenyl)-propanamido)-butanoic acid
Dab(Tyr) (2S)-2-Amino-4-((2S)-2-amino-(4-hydroxyphenyl)-propanamido)-butanoic acid
Dab(His) (2S)-2-Amino-4-((2S)-2-amino-(1H-imidazol-5-yl)-propanamido)-butanoic acid
Dab(Trp) (2S)-2-Amino-4-((2S)-2-amino-(1H-indol-3-yl)-propanamido)-butanoic acid
Orn(Phe) (2S)-2-Amino-5-((2S)-2-amino-3-phenyl)-propanamido)-pentanoic acid
Lys(Phe) (2S)-2-Amino-6-((2S)-2-amino-3-phenyl)-propanamido)-hexanoic acid
Asp(Phe) (2S)-2-Amino-4-((1S)-1-carboxy-2-phenylethylamino)-4-oxobutanoic acid
Asp(Tyr) (2S)-2-Amino-4-((1S)-1-carboxy-2-(4-hydroxyphenyl) ethylamino)-4-oxobutanoic acid
Asp(His) (2S)-2-Amino-4-((1S)-1-carboxy-2-(1H-imidazol-5-yl) ethylamino)-4-oxobutanoic acid Asp(Trp) (2S)-2-Amino-4-((1S)-1-carboxy-2-(1H-indol-3-yl) ethylamino)-4-oxobutanoic acid
Glu(Phe) (2S)-2-Amino-5-((1S)-1-carboxy-2-phenylethylamino)-5-oxopentanoic acid
Glu(Tyr) (2S)-2-Amino-5-((1S)-1-carboxy-2-(4-hydroxyphenyl) ethylamino)-5-oxopentanoic acid
Glu(His) (2S)-2-Amino-5-((1S)-1-carboxy-2-(1H-imidazol-5-yl) ethylamino)-5-oxopentanoic acid
Glu(Trp) (2S)-2-Amino-5-((1S)-1-carboxy-2-(1H-indol-3-yl) ethylamino)-5-oxopentanoic acid
Dap(Pentanoyl) (2S)-2-Amino-3-pentanamido-propanoic acid
Dap(Hexanoyl) (2S)-2-Amino-3-hexanamido-propanoic acid
Dap(Heptanoyl) (2S)-2-Amino-3-heptanamido-propanoic acid
Dap(Octanoyl) (2S)-2-Amino-3-octanamido-propanoic acid
Dab(Propanoyl) (2S)-2-Amino-4-propanamido-butanoic acid
Dab(Butanoyl) (2S)-2-Amino-4-butanamido-butanoic acid
Dab(Pentanoyl) (2S)-2-Amino-4-pentanamido-butanoic acid
Dab(Hexanoyl) (2S)-2-Amino-4-hexanamido-butanoic acid
Dab(Heptanoyl) (2S)-2-Amino-4-heptanamido-butanoic acid
Dab(Octanoyl) (2S)-2-Amino-4-octanamido-butanoic acid
Orn(Propanoyl) (2S)-2-Amino-5-propanamido-pentanoic acid
Orn(Butanoyl) (2S)-2-Amino-5-butanamido-pentanoic acid
Orn(Pentanoyl) (2S)-2-Amino-5-pentanamido-pentanoic acid
Orn(Hexanoyl) (2S)-2-Amino-5-hexanamido-pentanoic acid
Orn(Heptanoyl) (2S)-2-Amino-5-heptanamido-pentanoic acid
Orn(Octanoyl) (2S)-2-Amino-5-octanamido-pentanoic acid
Glu(Phenethyl) (2S)-2-Amino-5-phenethylamino-5-oxopentanoic acid
Glu(Phenpropyl) (2S)-2-Amino-5-(phenylpropyl)amino-5-oxopentanoic acid
Glu(Phenbutyl) (2S)-2-Amino-5-(phenylbutyl)amino-5-oxopentanoic acid
Glu(Phenpentyl) (2S)-2-Amino-5-(phenylpentyl)amino-5-oxopentanoic acid
Asp(Phenethyl) (2S)-2-Amino-4-phenethylamino-4-oxobutanoic acid
Asp(Phenpropyl) (2S)-2-Amino-4-(phenylpropyl)amino-4-oxobutanoic acid
Asp(Phenbutyl) (2S)-2-Amino-4-(phenylbutyl)amino-4-oxobutanoic acid
Asp(Phenpentyl) (2S)-2-Amino-4-(phenylpentyl)amino-4-oxobutanoic acid
 Particularly preferred residues for group C are:
AllylGly L-Allylglycine
Ala(CF$_3$) L-Trifluoroalanine
Abu L-α-Aminobutyric acid
Ala L-Alanine
$^D$Ala D-Alanine
Ile L-Isoleucine
$^D$Ile D-Isoleucine
Leu L-Leucine
$^D$Leu D-Leucine
Met L-Methionine
$^D$Met D-Methionine
Val L-Valine
$^D$Val D-Valine
tBuA L-t-Butylalanine
$^D$tBuA D-t-Butylalanine
tBuG L-tert.-Butylglycine
$^D$tBuG D-tert.-Butylglycine
Cha L-Cyclohexylalanine
$^D$Cha D-Cyclohexylalanine
C$_4$al L-3-Cyclobutylalanine
$^D$C$_4$al D-3-Cyclobutylalanine
C$_5$al L-3-Cyclopentylalanine
$^D$C$_5$al D-3-Cyclopentylalanine
Nle L-Norleucine
$^D$Nle D-Norleucine
hAla L-Homo-alanine
$^D$hAla D-Homo-alanine
hIle L-Homo-isoleucine
$^D$hIle D-Homo-isoleucine
hLeu L-Homo-leucine
$^D$hLeu D-Homo-leucine
hNle L-Homo-norleucine
$^D$hNle D-Homo-norleucine
hMet L-Homo-Methionine
$^D$hMet D-Homo-Methionine
hSer(Me) L-Homo-O-methylserine
$^D$hSer(Me) D-Homo-O-methylserine
hVal L-Homo-valine
$^D$hVal D-Homo-va line
hCha L-Homo-cyclohexylalanine
$^D$hCha D-Homo-cyclohexylalanine
OctGly L-Octylglycine
$^D$OctGly D-Octylglycine
NMeAla L-N-Methylalanine
NMe$^D$Ala D-N-Methylalanine
NMeVal L-N-Methylvaline
NMe$^D$Val D-N-Methylvaline
NMeIle L-N-Methylisoleucine
NMe$^D$Ile D-N-Methylisoleucine
NMeLeu L-N-Methylleucine
NMe$^D$Leu D-N-Methylleucine
NMeNle L-N-Methylnorleucine
NMe$^D$Nle D-N-Methylnorleucine
NMeNle L-N-Methylnorleucine
NMe$^D$Nle D-N-Methylnorleucine
NMeMet L-N-Methylmethionine
NMe$^D$Met D-N-Methylmethionine
 Particularly preferred residues for group D are:
His L-Histidine
$^D$His D-Histidine
Phe L-Phenylalanine
$^D$Phe D-Phenylalanine
Trp L-Tryptophan
$^D$Trp D-Tryptophan
Tyr L-Tyrosine
$^D$Tyr D-Tyrosine
2Pal (2S)-2-Amino-3-(pyridine-2'-yl)-propionic acid
$^D$2Pal (2R)-2-Amino-3-(pyridine-2'-yl)-propionic acid
4Pal (2S)-2-Amino-3-(pyridine-4'-yl)-propionic acid
$^D$4Pal (2R)-2-Amino-3-(pyridine-4'-yl)-propionic acid
Phg L-Phenylglycine
$^D$Phg D-Phenylglycine
2Nal L-2-Naphthylalanine
$^D$2Nal D-2-Naphthylalanine
1-Nal L-1-Naphthylalanine
$^D$1Nal D-1-Naphthylalanine
4ClPhe L-4-Chlorophenylalanine
$^D$4ClPhe D-4-Chlorophenylalanine
3ClPhe L-3-Chlorophenylalanine
$^D$3ClPhe D-3-Chlorophenylalanine
2ClPhe L-2-Chlorophenylalanine <sup>D</sup>2ClPhe D-2-Chlorophenylalanine
3,4Cl<sub>2</sub>Phe L-3,4-Dichlorophenylalanine
<sup>D</sup>3,4Cl<sub>2</sub>Phe D-3,4-Dichlorophenylalanine
4FPhe L-4-Fluorophenylalanine
<sup>D</sup>4Fphe D-4-Fluorophenylalanine
3FPhe L-3-Fluorophenylalanine
<sup>D</sup>3FPhe D-3-Fluorophenylalanine
2FPhe L-2-Fluorophenylalanine
<sup>D</sup>2FPhe D-2-Fluorophenylalanine
Thi L-β-2-Thienylalanine
<sup>D</sup>Thi D-β-2-Thienylalanine
Tza L-2-Thiazolylalanine
<sup>D</sup>Tza D-2-Thiazolylalanine
Tyr(Bzl) L-O-Benzyltyrosine
<sup>D</sup>Tyr(Bzl) D-O-Benzyltyrosine
His(Bzl) (3S)-2-Amino-3-(1'-benzylimidazole-4'-yl)-propionic acid
<sup>D</sup>His(Bzl) (3R)-2-Amino-3-(1'-benzylimidazole-4'-yl)-propionic acid
Bip L-(4-phenyl)phenylalanine
<sup>D</sup>Bip D-(4-phenyl)phenylalanine
Ser(Bzl) L-O-Benzylserine
<sup>D</sup>Ser(Bzl) D-O-Benzylserine
Thr(Bzl) L-O-Benzylthreonine
<sup>D</sup>Thr(Bzl) D-O-Benzylthreonine
hPhe L-Homo-phenylalanine
<sup>D</sup>hPhe D-Homo-phenylalanine
DiHPhe L-Dihomo-phenylalanine, (2S)-2-amino-5-phenyl-pentanoic acid
hTrp L-Homo-tryptophan
<sup>D</sup>hTrp D-Homo-tryptophan
hTyr L-Homo-tyrosine
<sup>D</sup>hTyr D-Homo-tyrosine
hHis L-Homo-histidine
<sup>D</sup>hHis D-Homo-histidine
Bpa L-4-Benzoylphenylalanine
<sup>D</sup>Bpa D-4-Benzoylphenylalanine
NMePhe L-N-Methylphenylalanine
NMe<sup>D</sup>Phe D-N-Methylphenylalanine
NMeTyr L-N-Methyltyrosine
NMe<sup>D</sup>Tyr D-N-Methyltyrosine
NMeHis L-N-Methylhistidine
NMe<sup>D</sup>His D-N-Methylhistidine
NMeTrp L-N-Methyltryptophane
NMe<sup>D</sup>Trp D-N-Methyltryptophane
    Particularly preferred residues for group E are
Arg L-Arginine
<sup>D</sup>Arg D-Arginine
Lys L-Lysine
<sup>D</sup>Lys D-Lysine
Orn L-Ornithine
<sup>D</sup>Orn D-Ornithine
Dap L-2,3-Diaminopropionic acid
<sup>D</sup>Dap D-2,3-Diaminopropionic acid
Dpr L-2,3-Diaminopropionic acid
<sup>D</sup>Dpr D-2,3-Diaminopropionic acid
Dab L-2,4-Diaminobutyric acid
<sup>D</sup>Dab D-2,4-Diaminobutyric acid
Dbu (2S, 3S)-2,3-Diaminobutyric acid
<sup>D</sup>Dbu (2R)-2,3-Diamino-butyric acid
Cit L-Citrulline
<sup>D</sup>Cit D-Citrulline
4AmPhe L-para-Aminophenylalanine
<sup>D</sup>4AmPhe D-para-Aminophenylalanine
3AmPhe L-meta-Aminophenylalanine
<sup>D</sup>3AmPne D-meta-Aminophenylalanine
2AmPhe L-ortho-Aminophenylalanine
<sup>D</sup>2AmPhe D-ortho-Aminophenylalanine
Phe(mC(NH<sub>2</sub>)=NH) L-meta-Amidinophenylalanine
<sup>D</sup>Phe(mC(NH<sub>2</sub>)=NH) D-meta-Amidinophenylalanine
Phe(pC(NH<sub>2</sub>)=NH) L-para-Amidinophenylalanine
<sup>D</sup>Phe(pC(NH<sub>2</sub>)=NH) D-para-Amidinophenylalanine
Phe(mNHC(NH<sub>2</sub>)=NH) L-meta-Guanidinophenylalanine
<sup>D</sup>Phe(mNHC(NH<sub>2</sub>)=NH) D-meta-Guanidinophenylalanine
Phe(pNHC(NH<sub>2</sub>)=NH) L-para-Guanidinophenylalanine
<sup>D</sup>Phe(pNHC(NH<sub>2</sub>)=NH) D-para-Guanidinophenylalanine
hArg L-Homo-arginine
<sup>D</sup>hArg D-Homo-arginine
hLys L-Homo-lysine
<sup>D</sup>hLYS D-Homo-lysine
AcLys L-N-Acetyllysine
<sup>D</sup>AcLys N-Acetyl-D-lysine
NMeLys L-N-Methyllysine
NMe<sup>D</sup>Lys D-N-Methyllysine
NMeArg L-N-Methylarginine
NMe<sup>D</sup>Arg D-N-Methylarginine
NMe<sup>D</sup>ab L-N-Methyl-2,4-diamino butyric acid
NMe<sup>D</sup>Dab D-N-Methyl-2,4-diamino butyric acid
    Particularly preferred residues for group F are
Asn L-Asparagine
<sup>D</sup>Asn D-Asparagine
Asp L-Aspartic acid
<sup>D</sup>Asp D-Aspartic acid
Cys L-Cysteine
<sup>D</sup>Cys D-Cysteine
Gln L-Glutamine
<sup>D</sup>Gln D-Glutamine
Glu L-Glutamic acid
<sup>D</sup>Glu D-Glutamic acid
Ser L-Serine
<sup>D</sup>Ser D-Serine
Thr L-Threonine
<sup>D</sup>Thr D-Threonine
Pen L-Penicillamine
<sup>D</sup>Pen D-Penicillamine
alloThr (2S, 3S)-2-Amino-3-hydroxy-butyric acid
<sup>D</sup>alloThr (2R, 3S)-2-Amino-3-hydroxy-butyric acid
Leu3OH (2S, 3R)-2-Amino-3-hydroxy-4-methyl-pentanoic acid
<sup>D</sup>Leu3OH (2R, 3R)-2-Amino-3-hydroxy-4-methyl-pentanoic acid
hCys L-Homo-cysteine
<sup>D</sup>hCys D-Homo-cysteine
hSer L-Homo-serine
<sup>D</sup>hSer D-Homo-serine
hGlu L-Homo-glutamic acid
<sup>D</sup>hGlu D-glutamic acid
hGln L-Homo-glutamine
<sup>D</sup>hGln D-Homo-glutamine
hThr L-Homo-threonine
<sup>D</sup>hThr D-Homo-threonine
NMeSer L-N-Methylserine
NMe<sup>D</sup>Ser D-N-Methylserine
NMeAsp L-N-Methylaspartic acid
NMe<sup>D</sup>Asp D-N-Methylaspartic acid
NMeGlu L-N-Methylglutamic acid
NMe<sup>D</sup>Glu D-N-Methylglutamic acid
NMeCys L-N-Methylcysteine
NMe<sup>D</sup>Cys D-N-Methylcysteine
NMeAsn L-N-Methylasparagine
NMe<sup>D</sup>Asn D-N-Methylasparagine
NMeGln L-N-Methylglutamine
NMe<sup>D</sup>Gln D-N-Methylglutamine
NMeThr L-N-Methylthreonine NMe<sup>D</sup>Thr D-N-Methylthreonine
Particularly preferred residues for group I are
(AEt)G N-(2-Aminoethyl)glycine
(APr)G N-(3-Amino-n-propyl)glycine
(ABu)G, Nlys N-(4-Amino-n-butyl)glycine
(APe)G N-(5-Amino-n-pentyl)glycine
(GuEt)G N-(2-Guanidinoethyl)glycine
(GuPr)G N-(3-Guanidino-n-propyl)glycine
(GuBu)G N-(4-Guanidino-n-butyl)glycine
(GuPe)G N-(5-Guanidino-n-pentyl)glycine
(CboMe)G N-(Carboxymethyl)glycine
(CboEt)G, Nglu N-(2-Carboxyethyl)glycine
(CboPr)G N-(3-Carboxypropyl)glycine
(CbaMe)G N-(Carbamoylmethyl)glycine
(CbaEt)G N-(2-Carbamoylethyl)glycine
(CbaPr)G N-(3-Carbamoylpropyl)glycine
(HyEt)G N-(2-Hydroxyethyl)glycine
(HyPr)G (2R)—N-(2-Hydroxypropyl)glycine
Particularly preferred residues for group M are
H-$\gamma^4$-DihTyr-OH (4R)-4-Amino-5-(4'-hydroxyphenyl)-pentanoic acid
H-$\gamma^4$-DihHis-OH (4R)-4-Amino-5-(imidazole-4'-yl)-pentanoic acid
H-$\gamma^4$-DihPhe-OH (4R)-4-Amino-5-phenyl-pentanoic acid
H-$\gamma^4$-DiTrp-OH (4R)-4-Amino-5-(indol-3'-yl)-pentanoic acid
H-$\gamma^4$-DihSer-OH (4R)-4-Amino-5-hydroxy-pentanoic acid
H-$\gamma^4$-DihAsp-OH (4R)-4-Amino-hexanedioic acid
H-$\gamma^4$-DihGlu-OH 4-Amino-heptanedioic acid
H-$\gamma^4$-DihLys-OH (4S)-4,8-Diamino-octanoic acid
H-$\gamma^4$-DihArg-OH (4S)-4-Amino-7-guanidino-heptanoic acid
H-$\gamma^4$-DihAsn-OH (4R)-4-Amino-5-carbamoyl-pentanoic acid
H-$\gamma^4$-DihGln-OH (4S)-4-Amino-6-carbamoyl-hexanoic acid
H-$\gamma^4$-DihThr-OH (4R, 5R)-4-Amino-5-hydroxy-hexanoic acid
H-$\gamma^4$-DiHCit-OH (4S)-4-Amino-7-carbamidyl-heptanoic acid
H-$\gamma^4$-DiHOrn-OH (4S)-4,7-Diamino-heptanoic acid
HH-$\gamma^4$-DiH4AmPhe-OH (4R)-4-Amino-5-(4'-aminophenyl)-pentanoic acid
H-$\gamma^4$-DiH3AmPhe-OH (4R)-4-Amino-5-(3'-aminophenyl)-pentanoic acid
H-$\gamma^4$-DiH2AmPhe-OH (4R)-4-Amino-5-(2'-aminophenyl)-pentanoic acid
H-$\gamma^4$-DiHPhe(mC(NH$_2$)=NH)—OH (4R)-4-Amino-5-(3'-amidinophenyl)-pentanoic acid
H-$\gamma^4$-DiHPhe(pC(NH$_2$)=NH)—OH (4R)-4-Amino-5-(4'-amidinophenyl)-pentanoic acid
H-$\gamma^4$-DiHPhe(mNHC(NH$_2$)=NH)—OH (4R)-4-Amino-5-(3'-guanidino-phenyl)-pentanoic acid
H-$\gamma^4$-DiHPhe(pNHC(NH$_2$)=NH)—OH (4R)-4-Amino-5-(4'-guanidino-phenyl)-pentanoic acid
H-$\gamma^4$-DiH2Pal-OH (4R)-4-Amino-5-(pyridine-4'-yl)-pentanoic acid
H-$\gamma^4$-DiH4Pal-OH (4R)-4-Amino-5-(pyridine-4'-yl)-pentanoic acid
H-$\gamma^4$-DiHPhg-OH (4R)-4-Amino-4-phenyl-butyric acid
H-$\gamma^4$-DiH2Nal-OH (4S)-4-Amino-5-(2'-naphthyl)-pentanoic acid
H-$\gamma^4$-DiH1Nal-OH (4S)-4-Amino-5-(1'-naphthyl)-pentanoic acid
H-$\gamma^4$-DiH4ClPhe-OH (4R)-4-Amino-5-(4'-chlorophenyl)-pentanoic acid
H-$\gamma^4$-DiH3ClPhe-OH (4R)-4-Amino-5-(3'-chlorophenyl)-pentanoic acid
H-$\gamma^4$-DiH2ClPhe-OH (4R)-4-Amino-5-(2'-chlorophenyl)-pentanoic acid
H-$\gamma^4$-DiH3,4Cl$_2$Phe-OH (4R)-4-Amino-5-(3',4'-dichlorophenyl)-pentanoic acid
H-$\gamma^4$-DiH4FPhe-OH (4R)-4-Amino-5-(4'-fluorophenyl)-pentanoic acid
H-$\gamma^4$-DiH3FPhe-OH (4R)-4-Amino-5-(3'-fluorophenyl)-pentanoic acid
H-$\gamma^4$-DiH2FPhe-OH (4R)-4-Amino-5-(2'-fluorophenyl)-pentanoic acid
H-$\gamma^4$-DiHThi-OH (4R)-4-Amino-5-(2'-thienyl)-pentanoic acid
H-$\gamma^4$-DiHTza-OH (4R)-4-Amino-5-(2'-thiazolyl)-pentanoic acid
H-$\gamma^4$-DiHMso-OH (4R)-4-Amino-5-methylsulfoxyl-pentanoic acid
H-$\gamma^4$-DiHAcLys-OH (4S)-8-Acetylamino-4-amino-ocatanoic acid
H-$\gamma^4$-DiHDpr-OH (4R)-4,5-Diamino-pentanoic acid
H-$\gamma^4$-DiHA$_2$Bu-OH (4R)-4,5-Diamino-hexanoic acid
H-$\gamma^4$-DiHDbu-OH (4R)-4,5-Diamino-hexanoic acid
H-$\gamma^4$-DiHY(Bzl)-OH (4R)-4-Amino-5-(4'-benzyloxyphenyl)-pentanoic acid
H-$\gamma^4$-DiHH(Bzl)-OH (4R)-4-Amino-5-(1'-benzylimidazole-4'-yl)-pentanoic acid
H-$\gamma^4$-DiHBip-OH (4R)-4-Amino-5-biphenylyl-pentanoic acid
H-$\gamma^4$-DiHS(Bzl)-OH (4S)-4-Amino-5-(benzyloxy)-pentanoic acid
H-$\gamma^4$-DiHT(Bzl)-OH (4R, 5R)-4-Amino-5-benzyloxy-hexanoic acid
H-$\gamma^4$-DiHalloT-OH (4R, 5S)-4-Amino-5-hydroxy-hexanoic acid
H-$\gamma^4$-DiHLeu3OH—OH (4R, 5R)-4-Amino-5-hydroxy-6-methyl-heptanoic acid
H-$\gamma^4$-DiHhArg-OH (4S)-4-Amino-8-guanidino-octanoic acid
H-$\gamma^4$-DiHhGlu-OH (4S)-4-Amino-ocatanedioic acid
H-$\gamma^4$-DiHhGln-OH (4S)-4-Amino-7-carbamoyl-heptanoic acid
H-$\gamma^4$-DiHhHis-OH (4S)-4-Amino-6-(imidazole-4'-yl)-hexanoic acid
H-$\gamma^4$-DiHhLys-OH (4S)-4,9-Diamino-nonanoic acid
H-$\gamma^4$-DiHhPhe-OH (4S)-4-Amino-6-phenyl-hexanoic acid
H-$\gamma^4$-DiHhSer-OH (4R)-4-Amino-6-hydroxy-hexanoic acid
H-$\gamma^4$-DiHhThr-OH (4R, 6R)-4-Amino-6-hydroxy-heptanoic acid
H-$\gamma^4$-DiHhTrp-OH (4S)-4-Amino-6-(indol-3'-yl)-hexanoic acid
H-$\gamma^4$-DiHhTyr-OH (4S)-4-Amino-6-(4'-hydroxyphenyl)-hexanoic acid
H-$\gamma^4$-DihBpa-OH (4R)-4-Amino-5-(4'-benzoylphenyl)-pentanoic acid
Particularly preferred residues for group N are:
H-$\beta^3$-HAla-OH (3S)-3-Amino-butyric acid
H-$\beta^3$-HVal-OH (3R)-3-Amino-4-methyl-valeric acid
H-$\beta^3$-HIle-OH (3R, 4S)-3-Amino-4-methyl-hexanoic acid
H-$\beta^3$-HLeu-OH (3S)-3-Amino-5-methyl-hexanoic acid
H-$\beta^3$-HMet-OH (3S)-3-Amino-5-methylthio pentanoic acid
H-$\beta^3$-HTyr-OH (3S)-3-Amino-4-(4'-hydroxyphenyl)-butyric acid
H-$\beta^3$-HHis-OH (3S)-3-Amino-4-(imidazole-4'-yl)-butyric acid
H-$\beta^3$-HPhe-OH (3S)-3-Amino-4-phenyl-butyric acid
H-$\beta^3$-HTrp-OH (3S)-3-Amino-4-(indol-3'-yl)-butyric acid H-β³-HSer-OH (3R)-3-Amino-4-hydroxy-butyric acid
H-β³-HAsp-OH 3-Amino-pentanedioic acid
H-β³-HGlu-OH (3S)-3-Amino-hexanedioic acid
H-β³-HLys-OH (3S)-3,7-Diamino-heptanoic acid
H-β³-HArg-OH (3S)-3-Amino-6-guanidino-hexanoic-acid
H-β³-HAsn-OH (3S)-3-Amino-4-carbamoyl-butyric acid
H-β³-HGln-OH (3S)-3-Amino-5-carbamoyl-pentanoic acid
H-β³-HThr-OH (3R, 4R)-3-Amino-4-hydroxy-pentanoic acid
H-β³-HCit-OH (3S)-3-Amino-6-carbamidyl-hexanoic acid
H-β³-HOrn-OH (3S)-3,6-Diamino-hexanoic acid
H-β³-HtBuA-OH (3S)-3-Amino-5,5-dimethyl-hexanoic acid
H-β³-HSar-OH N-Methyl-3-amino-propionic acid
H-β³-HPen-OH (3R)-3-Amino-4-methyl-4-mercapto-pentanoic acid
H-β³-HtBuG-OH (3R)-3-Amino-4,4-dimethyl-pentanoic acid
H-β³-H4AmPhe-OH (3S)-3-Amino-4-(4'-aminophenyl)-butyric acid
H-β³-H3AmPhe-OH (3S)-3-Amino-4-(3'-aminophenyl)-butyric acid
H-β³-H2AmPhe-OH (3S)-3-Amino-4-(2'-aminophenyl)-butyric acid
H-β³-HPhe(mC(NH₂)=NH)—OH (3S)-3-Amino-4-(3'-amidinophenyl)-butyric acid
H-β³-HPhe(pC(NH₂)=NH)—OH (3S)-3-Amino-4-(4'-amidinophenyl)-butyric acid
H-β³-HPhe(mNHC(NH₂)=NH)—OH (3S)-3-Amino-4-(3'-guanidinophenyl)-butyric acid
H-β³-HPhe(pNHC(NH₂)=NH)—OH (3S)-3-Amino-4-(4'-guanidino-phenyl)-butyric acid
H-β³-H2Pal-OH (3S)-3-Amino-4-(pyridine-2'-yl)-butyric acid
H-β³-H4Pal-OH (3S)-3-Amino-4-(pyridine-4'-yl)-butyric acid
H-β³-HPhg-OH (3R)-3-Amino-3-phenyl-propionic acid
H-β³-HCha-OH (3S)-3-Amino-4-cyclohexyl-butyric acid
H-β³-HC₄al-OH (3S)-3-Amino-4-cyclobutyl-butyric acid
H-β³-HC₅al-OH (3S)-3-Amino-4-cyclopentyl-butyric acid
H-β³-HNle-OH (3S)-3-Amino-heptanoic acid
H-β³-H2Nal-OH (3S)-3-Amino-4-(2'-naphthyl)-butyric acid
H-β³-H1Nal-OH (3S)-3-Amino-4-(1'-naphthyl)-butyric acid
H-β³-H4ClPhe-OH (3S)-3-Amino-4-(4'-chlorophenyl)-butyric acid
H-β³-H3ClPhe-OH (3S)-3-Amino-4-(3'-chlorophenyl)-butyric acid
H-β³-H2ClPhe-OH (3S)-3-Amino-4-(2'-chlorophenyl)-butyric acid
H-β³-H3,4Cl₂Phe-OH (3S)-3-Amino-4-(3',4'-dichlorophenyl)-butyric acid
H-β³-H4FPhe-OH (3S)-3-Amino-4-(4'-fluorophenyl)-butyric acid
H-β³-H3FPhe-OH (3S)-3-Amino-4-(3'-fluorophenyl)-butyric acid
H-β³-H2FPhe-OH (3S)-3-Amino-4-(2'-fluorophenyl)-butyric acid
H-β³-HThi-OH (3R)-3-Amino-4-(2'-thienyl)-butyric acid
H-β³-HTza-OH (3R)-3-Amino-4-(2'-thiazolyl)-butyric acid
H-β³-HMso-OH (3R)-3-Amino-4-methylsulfoxyl-butyric acid
H-β³-HAcLys-OH (3S)-7-Acetylamino-3-amino-heptanoic acid
H-β³-HDpr-OH (3R)-3,4-diamino-butyric acid
H-β³-HA₂Bu-OH (3S)-3,5-Diamino-pentanoic acid
H-β³-HDbu-OH (3R)-3,4-Diamino-pentanoic acid
H-β³-HY(Bzl)-OH (3S)-3-Amino-4-(4'-benzyloxyphenyl)-butyric acid
H-β³-HH(Bzl)-OH (3S)-3-Amino-4-(1'-benzylimidazole-4'-yl)-butyric acid
H-β³-HBip-OH (3S)-3-Amino-4-biphenylyl-butyric acid
H-β³-HS(Bzl)-OH (3S)-3-Amino-4-(benzyloxy)-butyric acid
H-β³-HT(Bzl)-OH (3R, 4R)-3-Amino-4-benzyloxy-pentanoic acid
H-β³-HalloT-OH (3R, 4S)-3-Amino-4-hydroxy-pentanoic acid
H-β³-HLeu3OH—OH (3R, 4R)-3-Amino-4-hydroxy-5-methyl-hexanoic acid
H-β³-HhAla-OH (3S)-3-Amino-pentanoic acid
H-β³-HhArg-OH (3S)-3-Amino-7-guanidino-heptanoic acid
H-β³-HhGlu-OH (3S)-3-Amino-heptanedioic acid
H-β³-HhGln-OH (3S)-3-Amino-6-carbamoyl-hexanoic acid
H-β³-HhHis-OH (3S)-3-Amino-5-(imidazole-4'-yl)-pentanoic acid
H-β³-HhIle-OH (3S, 5S)-3-Amino-5-methyl-heptanoic acid
H-β³-HhLeu-OH (3S)-3-Amino-6-methyl-heptanoic acid
H-β³-HhNle-OH (3S)-3-Amino-octanoic acid
H-β³-DiAoc-OH (3S)-3,8-Diamino-octanoic acid
H-3-HhMet-OH (3S)-3-Amino-6-methylthio-hexanoic acid
H-β³-HhPe-OH (3S)-3-Amino-5-phenyl-pentanoic acid
H-β³-HhSer-OH (3S)-3-Amino-5-hydroxy-pentanoic acid
H-β³-HhThr-OH (3S, 5R)-3-Amino-5-hydroxy-hexanoic acid
H-β³-HhTrp-OH (3S)-3-Amino-5-(indol-3'-yl)-pentanoic acid
H-β³-HhThr-OH (3S)-3-Amino-5-(4'-hydroxyphenyl)-pentanoic acid
H-β³-HhCha-OH (3S)-3-Amino-5-cyclohexyl-pentanoic acid
H-β³-HBpa-OH (3S)-3-Amino-4-(4'-benzoylphenyl)-butyric acid
H-β³-HOctG-OH (3S)-3-Amino-undecanoic acid
H-β³-HNle-OH (3S)-3-Amino-heptanoic acid
Particularly preferred residues for group O are:
Dap(Phe) (2S)-2-Amino-3-((2S)-2-amino-3-phenyl)-propanamido)-propanoic acid
Dap(Tyr) (2S)-2-Amino-3-((2S)-2-amino-(4-hydroxyphenyl)-propanamido)-propanoic acid
Dap(His) (2S)-2-Amino-3-((2S)-2-amino-(1H-imidazol-5-yl)-propanamido)-propanoic acid
Dap(Trp) (2S)-2-Amino-3-((2S)-2-amino-(1H-indol-3-yl)-propanamido)-propanoic acid
Dab(Phe) (2S)-2-Amino-4-((2S)-2-amino-3-phenyl)-propanamido)-butanoic acid
Dab(Tyr) (2S)-2-Amino-4-((2S)-2-amino-(4-hydroxyphenyl)-propanamido)-butanoic acid
Dab(His) (2S)-2-Amino-4-((2S)-2-amino-(1H-imidazol-5-yl)-propanamido)-butanoic acid
Dab(Trp) (2S)-2-Amino-4-((2S)-2-amino-(1H-indol-3-yl)-propanamido)-butanoic acid
Orn(Phe) (2S)-2-Amino-5-((2S)-2-amino-3-phenyl)-propanamido)-pentanoic acid
Lys(Phe) (2S)-2-Amino-6-((2S)-2-amino-3-phenyl)-propanamido)-hexanoic acid
Particularly preferred residues for group P are:
Asp(Phe) (2S)-2-Amino-4-((1S)-1-carboxy-2-phenylethylamino)-4-oxobutanoic acid
Asp(Tyr) (2S)-2-Amino-4-((1S)-1-carboxy-2-(4-hydroxyphenyl) ethylamino)-4-oxobutanoic acid
Asp(His) (2S)-2-Amino-4-((1S)-1-carboxy-2-(1H-imidazol-5-yl) ethylamino)-4-oxobutanoic acid Asp(Trp) (2S)-2-Amino-4-((1S)-1-carboxy-2-(1H-indol-3-yl) ethylamino)-4-oxobutanoic acid
Glu(Phe) (2S)-2-Amino-5-((1S)-1-carboxy-2-phenylethylamino)-5-oxopentanoic acid
Glu(Tyr) (2S)-2-Amino-5-((1S)-1-carboxy-2-(4-hydroxyphenyl) ethylamino)-5-oxopentanoic acid
Glu(His) (2S)-2-Amino-5-((1S)-1-carboxy-2-(1H-imidazol-5-yl) ethylamino)-5-oxopentanoic acid
Glu(Trp) (2S)-2-Amino-5-((1S)-1-carboxy-2-(1H-indol-3-yl) ethylamino)-5-oxopentanoic acid
Particularly preferred residues for group Q are:
Dap(Pentanoyl) (2S)-2-Amino-3-pentanamido-propanoic acid
Dap(Hexanoyl) (2S)-2-Amino-3-hexanamido-propanoic acid
Dap(Heptanoyl) (2S)-2-Amino-3-heptanamido-propanoic acid
Dap(Octanoyl) (2S)-2-Amino-3-octanamido-propanoic acid
Dab(Propanoyl) (2S)-2-Amino-4-propanamido-butanoic acid
Dab(Butanoyl) (2S)-2-Amino-4-butanamido-butanoic acid
Dab(Pentanoyl) (2S)-2-Amino-4-pentanamido-butanoic acid
Dab(Hexanoyl) (2S)-2-Amino-4-hexanamido-butanoic acid
Dab(Heptanoyl) (2S)-2-Amino-4-heptanamido-butanoic acid
Dab(Octanoyl) (2S)-2-Amino-4-octanamido-butanoic acid
Orn(Propanoyl) (2S)-2-Amino-5-propanamido-pentanoic acid
Orn(Butanoyl) (2S)-2-Amino-5-butanamido-pentanoic acid
Orn(Pentanoyl) (2S)-2-Amino-5-pentanamido-pentanoic acid
Orn(Hexanoyl) (2S)-2-Amino-5-hexanamido-pentanoic acid
Orn(Heptanoyl) (2S)-2-Amino-5-heptanamido-pentanoic acid
Orn(Octanoyl) (2S)-2-Amino-5-octanamido-pentanoic acid
Particularly preferred residues for group R are:
Glu(Phenethyl) (2S)-2-Amino-5-phenethylamino-5-oxopentanoic acid
Glu(Phenpropyl) (2S)-2-Amino-5-(phenylpropyl)amino-5-oxopentanoic acid
Glu(Phenbutyl) (2S)-2-Amino-5-(phenylbutyl)amino-5-oxopentanoic acid
Glu(Phenpentyl) (2S)-2-Amino-5-(phenylpentyl)amino-5-oxopentanoic acid
Asp(Phenethyl) (2S)-2-Amino-4-phenethylamino-4-oxobutanoic acid
Asp(Phenpropyl) (2S)-2-Amino-4-(phenylpropyl)amino-4-oxobutanoic acid
Asp(Phenbutyl) (2S)-2-Amino-4-(phenylbutyl)amino-4-oxobutanoic acid
Asp(Phenpentyl) (2S)-2-Amino-4-(phenylpentyl)amino-4-oxobutanoic acid In a particular embodiment of the present invention the β-hairpin peptidomimetics are compounds of the general formula I,
and pharmaceutically acceptable salts thereof, wherein
$Xaa^1$ is OctGly; Arg; hArg; Cha; Dab(Octanoyl); Dab(Butanoyl); Glu(Phe); Glu(Phenethyl); Dab(Phe); or Lys(Phe);
$Xaa^2$ is Glu; Val; Leu; Nle; Phe; hPhe; DiHPhe; Tyr; hTyr; Trp; Dap(Phe); or Asp(Phe);
$Xaa^4$ is Ala; AllylGly; Abu; or Val;
$Xaa^6$ is Ile; or OctGly;
$Xaa^7$ is Pro; Nglu; or Nlys;
$Xaa^8$ is Pro; Oic; Nglu; Nlys; Pip; or Azt;
$Xaa^9$ is Gln; H-$β^3$-HGln-OH; or Tyr;
$Xaa^{10}$ is Lys; H-$β^3$-HLys-OH; H-$γ^4$-DiHLys-OH; Asn; or Gly;
$Xaa^{11}$ is hLeu; Ser; hSer; hSer(Me); Thr; alloThr; H-$γ^4$-DiHThr-OH; Asn; Gln; hGln; Dap; Tyr; H-$γ^4$-DiHTyr-OH; or His;
$Xaa^{12}$ is $^D$Pro; $^D$Ala; $^D$Val; $^D$Ser; $^D$Glu; $^D$Tyr; $^D$Lys; $^D$Arg; Gly; or Nlys; and
$Xaa^{13}$ is Pro; H-$β^3$-HPro-OH; H-$γ^4$-DiHPro-OH; $^D$Pro; Oic; Tic; Glu; Asp; Ala; Val; Thr; Lys; Tyr; Nglu; or $^D$Glu;
with the proviso that
$Xaa^1$ is Dab(Octanoyl); Glu(Phe); Dab(Phe); or Lys(Phe); and/or
$Xaa^2$ is Dap(Phe); or Asp(Phe); and/or
$Xaa^7$ is Nglu; or Nlys; and/or
$Xaa^8$ is Oic; Nglu; Nlys; Pip; or Azt; and/or
$Xaa^9$ is H-$β^3$-HGln-OH; and/or
$Xaa^{10}$ is H-$β^3$-HLys-OH; or H-$γ^4$-DiHLys-OH; and/or
$Xaa^{11}$ is H-$γ^4$-DiHThr-OH; or H-$γ^4$-DiHTyr-OH; and/or
$Xaa^{12}$ is $^D$Ala; $^D$Val; $^D$Ser; $^D$Glu; $^D$Tyr; $^D$Lys; $^D$Arg; or Nlys; and/or
$Xaa^{13}$ is H-$β^3$-HPro-OH; H-$γ^4$-DiHPro-OH; $^D$Pro; Oic; Glu; Asp; Thr; or $^D$Glu;
and with the further proviso that
if $Xaa^{11}$ is Tyr; or His, then
$Xaa^1$ is Arg; hArg; Glu(Phe); Glu(Phenethyl); Dab(Phe); or Lys(Phe); and/or
$Xaa^2$ is Dap(Phe); or Asp(Phe).

In another particular embodiment of the present invention the β-hairpin peptidomimetics are compounds of the general formula I,
and pharmaceutically acceptable salts thereof, wherein
$Xaa^1$ is OctGly; Dab(Phe); Arg; Dab(Octanoyl); or Glu(Phe);
$Xaa^2$ is Glu; Phe; Dap(Phe); Val; or hTyr;
$Xaa^4$ is Ala; or AllylGly;
$Xaa^6$ is Ile;
$Xaa^7$ is Pro; Nglu; or Nlys;
$Xaa^8$ is Pro; Nglu; Nlys; Pip; Azt; or Oic;
$Xaa^9$ is Gln; or H-$β^3$-HGln-OH;
$Xaa^{10}$ is Lys; H-$β^3$-HLys-OH; or H-$γ^4$-DiHLys-OH;
$Xaa^{11}$ is hSer; hSer(Me); Thr; alloThr; hGln; Dap; Tyr; or H-$γ^4$-DiHTyr-OH; H-$γ^4$-DiHThr-OH; Ser; or Asn;
$Xaa^{12}$ is $^D$Pro; $^D$Ala; $^D$Val; $^D$Tyr; $^D$Lys; or $^D$Ser; and
$Xaa^{13}$ is Pro; $^D$Pro; Oic; Ala; Tyr; Val; Lys; H-$β^3$-HPro-OH; $^D$Glu; or Glu;
with the proviso that
$Xaa^1$ is Dab(Phe); Dab(Octanoyl); or Glu(Phe); and/or
$Xaa^7$ is Nglu; or Nlys; and/or
$Xaa^8$ is Nglu; Nlys; Pip; Azt; or Oic; and/or
$Xaa^9$ is H-$β^3$-HGln-OH; and/or
$Xaa^{10}$ is H-$β^3$-HLys-OH; or H-$γ^4$-DiHLys-OH; and/or
$Xaa^{11}$ is H-$γ^4$-DiHTyr-OH; or H-$γ^4$-DiHThr-OH; and/or
$Xaa^{12}$ is $^D$Ala; $^D$Val; $^D$Tyr; $^D$Lys; or $^D$Ser; and/or
$Xaa^{13}$ is $^D$Pro; Oic; H-$β^3$-HPro-OH; or $^D$Glu;
and with the further proviso that
if $Xaa^{11}$ is Tyr, then
$Xaa^1$ is Dab(Phe); Arg; or Glu(Phe);
and/or
$Xaa^2$ is Dap(Phe).

In another particular embodiment of the present invention the β-hairpin peptidomimetics are compounds of the general formula I, and pharmaceutically acceptable salts thereof, wherein
$Xaa^1$ is OctGly; or Dab(Phe);
$Xaa^2$ is Glu;
$Xaa^4$ is Ala;

Xaa⁶ is Ile;
Xaa⁷ is Pro; Nglu; or Nlys;
Xaa⁸ is Pro; Nglu; Nlys; Pip; or Azt;
Xaa⁹ is Gln; or H-β³-HGln-OH;
Xaa¹⁰ is Lys; H-β³-HLys-OH; or H-γ⁴-DiHLys-OH;
Xaa¹¹ is hSer; hSer(Me); Thr; alloThr; hGln; Dap; Tyr; or H-γ⁴-DiHTyr-OH;
Xaa¹² is ᴰPro; ᴰAla; ᴰVal; ᴰTyr; or ᴰLys; and
Xaa¹³ is Pro; Oic; Ala; Tyr; or Val;
with the proviso that
  Xaa¹ is Dab(Phe); and/or
  Xaa⁷ is Nglu; or Nlys; and/or
  Xaa⁸ is Nglu; Nlys; Pip; or Azt; and/or
  Xaa⁹ is H-β³-HGln-OH; and/or
  Xaa¹⁰ is H-β³-HLys-OH; or H-γ⁴-DiHLys-OH; and/or
  Xaa¹¹ is hSer; hSer(Me); alloThr; hGln; Dap or H-γ⁴-DiHTyr-OH; and/or
  Xaa¹² is ᴰAla; ᴰVal; ᴰTyr; or ᴰLys; and/or
  Xaa¹³ is Oic;
and with the further proviso that
  if Xaa¹¹ is Tyr, then
    Xaa¹ is Dab(Phe).

In another particular embodiment of the present invention the β-hairpin peptidomimetics are compounds of the general formula I,
and pharmaceutically acceptable salts thereof, wherein
Xaa¹ is OctGly; Arg; Dab(Octanoyl); or Glu(Phe);
Xaa² is Glu; Phe; Dap(Phe); Val; or hTyr;
Xaa⁴ is Ala; or AllylGly
Xaa⁶ is Ile;
Xaa⁷ is Pro;
Xaa⁸ is Pro; or Oic;
Xaa⁹ is Gln;
Xaa¹⁰ is Lys;
Xaa¹¹ is Thr; H-γ⁴-DiHThr-OH; Tyr;
Xaa¹² is ᴰPro; ᴰVal; ᴰTyr; ᴰLys; or ᴰSer; and
Xaa¹³ is Pro; ᴰPro; Lys; Val; Tyr; H-β³-HPro-OH; ᴰGlu; or Glu;
with the proviso that
  Xaa¹ is Dab(Octanoyl); or Glu(Phe); and/or
  Xaa² is Dap(Phe); and/or
  Xaa⁸ is Oic; and/or
  Xaa¹¹ is H-γ⁴-DiHThr-OH; and/or
  Xaa¹² is ᴰVal; ᴰTyr; ᴰLys; or ᴰSer; and/or
  Xaa¹³ is ᴰPro; H-β³-HPro-OH; or ᴰGlu;
and with the further proviso that
  if Xaa¹¹ is Tyr, then
    Xaa¹ is Arg; or Glu(Phe); and/or
    Xaa² is Dap(Phe).

In still another particular embodiment of the present invention the β-hairpin peptidomimetics are compounds of the general formula I,
and pharmaceutically acceptable salts thereof, wherein
Xaa¹ is OctGly; Arg; hArg; Cha; Dab(Octanoyl); Dab(Butanoyl); Glu(Phe); Glu(Phenethyl); Dab(Phe); or Lys(Phe);
Xaa² is Glu; Val; Leu; Nle; Phe; hPhe; DiHPhe; Tyr; hTyr; Trp; Dap(Phe); or Asp(Phe);
Xaa⁴ is Ala; AllylGly; Abu; or Val;
Xaa⁶ is Ile; or OctGly;
Xaa⁷ is Pro; Nglu; or Nlys;
Xaa⁸ is Pro; Oic; Nglu; Nlys; Pip; or Azt;
Xaa⁹ is Gln; H-β³-HGln-OH; or Tyr;
Xaa¹⁰ is Lys; H-β³-HLys-OH; H-γ⁴-DiHLys-OH; Asn; or Gly;
Xaa¹¹ is hLeu; Ser; hSer; hSer(Me); Thr; alloThr; H-γ⁴-DiHThr-OH; Asn; Gln; hGln; Dap; Tyr; H-γ⁴-DiHTyr-OH; or His;
Xaa¹² is ᴰPro; ᴰAla; ᴰVal; ᴰSer; ᴰGlu; ᴰTyr; ᴰLys; ᴰArg; Gly; or Nlys; and
Xaa¹³ is Pro; H-β³-HPro-OH; H-γ⁴-DiHPro-OH; ᴰPro; Oic; Tic; Glu; Asp; Ala; Val; Thr; Lys; Tyr; or Nglu; or ᴰGlu;
with the proviso that
  Xaa¹ is Glu(Phe); Dab(Phe); or Lys(Phe); and/or
  Xaa² is Dap(Phe); or Asp(Phe).

In still another particular embodiment of the present invention the β-hairpin peptidomimetics are compounds of the general formula I,
and pharmaceutically acceptable salts thereof, wherein
Xaa¹ is OctGly; Arg; hArg; Cha; Dab(Octanoyl); Dab(Butanoyl); Glu(Phe); Glu(Phenethyl); Dab(Phe); or Lys(Phe);
Xaa² is Glu; Val; Leu; Nle; Phe; hPhe; DiHPhe; Tyr; hTyr; Trp; Dap(Phe); or Asp(Phe);
Xaa⁴ is Ala; AllylGly; Abu; or Val;
Xaa⁶ is Ile; or OctGly;
Xaa⁷ is Pro; Nglu; or Nlys;
Xaa⁸ is Pro; Oic; Nglu; Nlys; Pip; or Azt;
Xaa⁹ is Gln; H-β³-HGln-OH; or Tyr;
Xaa¹⁰ is Lys; H-β³-HLys-OH; H-γ⁴-DiHLys-OH; Asn; or Gly;
Xaa¹¹ is hLeu; Ser; hSer; hSer(Me); Thr; alloThr; H-γ⁴-DiHThr-OH; Asn; Gln; hGln; Dap; Tyr; H-γ⁴-DiHTyr-OH; or His;
Xaa¹² is ᴰPro; ᴰAla; ᴰVal; ᴰSer; ᴰGlu; ᴰTyr; ᴰLys; ᴰArg; Gly; or Nlys; and
Xaa¹³ is Pro; H-β³-HPro-OH; H-γ⁴-DiHPro-OH; ᴰPro; Oic; Tic; Glu; Asp; Ala; Val; Thr; Lys; Tyr; or Nglu; or ᴰGlu;
with the proviso that
  Xaa⁷ is Nglu; or Nlys; and/or
  Xaa⁸ is Nglu; or Nlys; and/or
  Xaa¹² is Nlys; and/or
  Xaa¹³ is Nglu;
and with the further proviso that
  if Xaa¹¹ is Tyr, then
    Xaa¹ is Arg; hArg; Glu(Phe); Glu(Phenethyl); Dab(Phe); or Lys(Phe); and/or
    Xaa² is Dap(Phe); or Asp(Phe).

In still another particular embodiment of the present invention the β-hairpin peptidomimetics are compounds of the general formula I, and pharmaceutically acceptable salts thereof, wherein
Xaa¹ is OctGly; Arg; hArg; Cha; Dab(Octanoyl); Dab(Butanoyl); Glu(Phe); Glu(Phenethyl); Dab(Phe); or Lys(Phe);
Xaa² is Glu; Val; Leu; Nle; Phe; hPhe; DiHPhe; Tyr; hTyr; Trp; Dap(Phe); or Asp(Phe);
Xaa⁴ is Ala; AllylGly; Abu; or Val;
Xaa⁶ is Ile; or OctGly;
Xaa⁷ is Pro; Nglu; or Nlys;
Xaa⁸ is Pro; Oic; Nglu; Nlys; Pip; or Azt;
Xaa⁹ is Gln; H-β³-HGln-OH; or Tyr;
Xaa¹⁰ is Lys; H-β³-HLys-OH; H-γ⁴-DiHLys-OH; Asn; or Gly;
Xaa¹¹ is hLeu; Ser; hSer; hSer(Me); Thr; alloThr; H-γ⁴-DiHThr-OH; Asn; Gln; hGln; Dap; Tyr; H-γ⁴-DiHTyr-OH; or His;
Xaa¹² is ᴰPro; ᴰAla; ᴰVal; ᴰSer; ᴰGlu; ᴰTyr; ᴰLys; ᴰArg; Gly; or Nlys; and
Xaa¹³ is Pro; H-β³-HPro-OH; H-γ⁴-DiHPro-OH; ᴰPro; Oic; Tic; Glu; Asp; Ala; Val; Thr; Lys; Tyr; or Nglu; or ᴰGlu;
with the proviso that Xaa⁹ is H-β³-HGln-OH; and/or
Xaa¹⁰ is H-β³-HLys-OH; and/or
Xaa¹³ is H-β³-HPro-OH;
and with the further proviso that
  if Xaa¹¹ is Tyr, then
    Xaa¹ is Arg; hArg; Glu(Phe); Glu(Phenethyl); Dab(Phe); or Lys(Phe); and/or
    Xaa² is Dap(Phe); or Asp(Phe).
In still another particular embodiment of the present invention the β-hairpin peptidomimetics are compounds of the general formula I,
and pharmaceutically acceptable salts thereof, wherein
Xaa¹ is OctGly; Arg; hArg; Cha; Dab(Octanoyl); Dab(Butanoyl); Glu(Phe); Glu(Phenethyl); Dab(Phe); or Lys(Phe);
Xaa² is Glu; Val; Leu; Nle; Phe; hPhe; DiHPhe; Tyr; hTyr; Trp; Dap(Phe); or Asp(Phe);
Xaa⁴ is Ala; AllylGly; Abu; or Val;
Xaa⁶ is Ile; or OctGly;
Xaa⁷ is Pro; Nglu; or Nlys;
Xaa⁸ is Pro; Oic; Nglu; Nlys; Pip; or Azt;
Xaa⁹ is Gln; H-β³-HGln-OH; or Tyr;
Xaa¹⁰ is Lys; H-β³-HLys-OH; H-γ⁴-DiHLys-OH; Asn; or Gly;
Xaa¹¹ is hLeu; Ser; hSer; hSer(Me); Thr; alloThr; H-γ⁴-DiHThr-OH; Asn; Gln; hGln; Dap; Tyr; H-γ⁴-DiHTyr-OH; or His;
Xaa¹² is ᴰPro; ᴰAla; ᴰVal; ᴰSer; ᴰGlu; ᴰTyr; ᴰLys; ᴰArg; Gly; or Nlys; and
Xaa¹³ is Pro; H-β³-HPro-OH; H-γ⁴-DiHPro-OH; ᴰPro; Oic; Tic; Glu; Asp; Ala; Val; Thr; Lys; Tyr or Nglu; or ᴰGlu;
with the proviso that
  Xaa¹⁰ is H-γ⁴-DiHLys-OH; and/or
  Xaa¹¹ is H-γ⁴-DiHThr-OH; or H-γ⁴-DiHTyr-OH; and/or
  Xaa¹³ is H-γ⁴-DiHPro-OH;
and with the further proviso that
  if Xaa¹¹ is Tyr, then
    Xaa¹ is Arg; hArg; Glu(Phe); Glu(Phenethyl); Dab(Phe); or Lys(Phe); and/or
    Xaa² is Dap(Phe); or Asp(Phe).
In still another particular embodiment of the present invention the β-hairpin peptidomimetics are compounds of the general formula I, and pharmaceutically acceptable salts thereof, wherein
Xaa¹ is OctGly; Arg; hArg; Cha; Dab(Octanoyl); Dab(Butanoyl); Glu(Phe); Glu(Phenethyl); Dab(Phe); or Lys(Phe);
Xaa² is Glu; Val; Leu; Nle; Phe; hPhe; DiHPhe; Tyr; hTyr; Trp; Dap(Phe); or Asp(Phe);
Xaa⁴ is Ala; AllylGly; Abu; or Val;
Xaa⁶ is Ile; or OctGly;
Xaa⁷ is Pro; Nglu; or Nlys;
Xaa⁸ is Pro; Oic; Nglu; Nlys; Pip; or Azt;
Xaa⁹ is Gln; H-β³-HGln-OH; or Tyr;
Xaa¹⁰ is Lys; H-β³-HLys-OH; H-γ⁴-DiHLys-OH; Asn; or Gly;
Xaa¹¹ is hLeu; Ser; hSer; hSer(Me); Thr¹⁷; alloThr; H-γ⁴-DiHThr-OH; Asn; Gln; hGln; Dap; Tyr; H-γ⁴-DiHTyr-OH; or His;
Xaa¹² is ᴰPro; ᴰAla; ᴰVal; ᴰSer; ᴰGlu; ᴰTyr; ᴰLys; ᴰArg; Gly; or Nlys; and
Xaa¹³ is Pro; H-β³-HPro-OH; H-γ⁴-DiHPro-OH; ᴰPro; Oic; Tic; Glu; Asp; Ala; Val; Thr; Lys; Tyr; or Nglu; or ᴰGlu;
with the proviso that
  Xaa⁸ and/or Xaa¹³ is Oic;

and with the further proviso that
  if Xaa¹¹ is Tyr, then
    Xaa¹ is Arg; hArg; Glu(Phe); Glu(Phenethyl); Dab(Phe); or Lys(Phe); and/or
    Xaa² is Dap(Phe); or Asp(Phe).
In still another particular embodiment of the present invention the β-hairpin peptidomimetics are compounds of the general formula I, and pharmaceutically acceptable salts thereof, wherein
Xaa¹ is OctGly; Arg; hArg; Cha; Dab(Octanoyl); Dab(Butanoyl); Glu(Phe); Glu(Phenethyl); Dab(Phe); or Lys(Phe);
Xaa² is Glu; Val; Leu; Nle; Phe; hPhe; DiHPhe; Tyr; hTyr; Trp; Dap(Phe); or Asp(Phe);
Xaa⁴ is Ala; AllylGly; Abu; or Val;
Xaa⁶ is Ile; or OctGly;
Xaa⁷ is Pro; Nglu; or Nlys;
Xaa⁸ is Pro; Oic; Nglu; Nlys; Pip; or Azt;
Xaa⁹ is Gln; H-β³-HGln-OH; or Tyr;
Xaa¹⁰ is Lys; H-β³-HLys-OH; H-γ⁴-DiHLys-OH; Asn; or Gly;
Xaa¹¹ is hLeu; Ser; hSer; hSer(Me); Thr; alloThr; H-γ⁴-DiHThr-OH; Asn; Gln; hGln; Dap; Tyr; H-γ⁴-DiHTyr-OH; or His;
Xaa¹² is ᴰPro; ᴰAla; ᴰVal; ᴰSer; ᴰGlu; ᴰTyr; ᴰLys; ᴰArg; Gly; or Nlys; and
Xaa¹³ is Pro; H-β³-HPro-OH; H-γ⁴-DiHPro-OH; ᴰPro; Oic; Tic; Glu; Asp; Ala; Val; Thr; Lys; Tyr; or Nglu; or ᴰGlu;
with the proviso that
  Xaa¹² is ᴰAla; ᴰVal; ᴰSer; ᴰGlu; ᴰTyr; ᴰLys; or ᴰArg;
and with the further proviso that
  if Xaa¹¹ is Tyr, then
    Xaa¹ is Arg; hArg; Glu(Phe); Glu(Phenethyl); Dab(Phe); or Lys(Phe); and/or
    Xaa² is Dap(Phe); or Asp(Phe).
In another particular embodiment of the present invention the β-hairpin peptidomimetic is a compound of the general formula I, and pharmaceutically acceptable salts thereof, selected from
Cyclo(-OctGly-Glu-Thr-Ala-Ser-Ile-Pro-Pro-Gln-Lys-hSer(Me)-ᴰPro-Pro-);
Cyclo(-OctGly-Glu-Thr-Ala-Ser-Ile-Pro-Pro-Gln-Lys-Dap-ᴰPro-Pro-);
Cyclo(-OctGly-Glu-Thr-Ala-Ser-Ile-Pro-Pro-Gln-Lys-alloThr-ᴰPro-Pro-);
Cyclo(-OctGly-Glu-Thr-Ala-Ser-Ile-Pro-Pro-Gln-Lys-hSer-ᴰPro-Pro-);
Cyclo(-OctGly-Glu-Thr-Ala-Ser-Ile-Pro-Pro-Gln-Lys-hGln-ᴰPro-Pro-);
Cyclo(-OctGly-Glu-Thr-Ala-Ser-Ile-Pro-Pro-Gln-Lys-Thr-ᴰPro-Oic-);
Cyclo(-OctGly-Glu-Thr-Ala-Ser-Ile-Nglu-Pro-Gln-Lys-Thr-ᴰPro-Pro-);
Cyclo(-OctGly-Glu-Thr-Ala-Ser-Ile-Pro-Pro-Gln-Lys-[H-γ⁴-DiHTyr-OH]-ᴰPro-Pro-);
Cyclo(-Dab(Phe)-Glu-Thr-Ala-Ser-Ile-Pro-Pro-Gln-Lys-Tyr-ᴰPro-Pro-);
Cyclo(-OctGly-Glu-Thr-Ala-Ser-Ile-Pro-Pro-GI n-Lys-Thr-ᴰAla-Ala-);
Cyclo(-OctGly-Glu-Thr-Ala-Ser-Ile-Pro-Pro-GI n-Lys-Thr-ᴰVal-Tyr-);
Cyclo(-OctGly-Glu-Thr-Ala-Ser-Ile-Pro-Pro-Gln-Lys-Thr-ᴰTyr-Tyr-);
Cyclo(-OctGly-Glu-Thr-Ala-Ser-Ile-Pro-Pro-GI n-Lys-Thr-ᴰLys-Val-);
Cyclo(-OctGly-Glu-Thr-Ala-Ser-Ile-Nlys-Pro-Gln-Lys-Thr-ᴰPro-Pro-);
Cyclo(-OctGly-Glu-Thr-Ala-Ser-Ile-Pro-Nglu-Gln-Lys-Thr-ᴰPro-Pro-);

Cyclo(-OctGly-Glu-Thr-Ala-Ser-Ile-Pro-Nlys-Gln-Lys-Thr-$^D$Pro-Pro-);
Cyclo(-OctGly-Glu-Thr-Ala-Ser-Ile-Pro-Pro-[H-β$^3$-HGln-OH]-Lys-Thr-$^D$Pro-Pro-);
Cyclo(-OctGly-Glu-Thr-Ala-Ser-Ile-Pro-Pro-Gln-[H-β$^3$-H Lys-OH]-Thr-$^D$Pro-Pro-);
Cyclo(-OctGly-Glu-Thr-Ala-Ser-Ile-Pro-Pro-Gln-[H-γ$^4$-DiHLys-OH]-Thr-$^D$Pro-Pro-);
Cyclo(-OctGly-Glu-Thr-Ala-Ser-Ile-Pro-Pip-Gln-Lys-Thr-$^D$Pro-Pro-);
Cyclo(-OctGly-Glu-Thr-Ala-Ser-Ile-Pro-Azt-Gln-Lys-Thr-$^D$Pro-Pro-).

In another particular embodiment of the present invention the β-hairpin peptidomimetic is a compound of the general formula I, and pharmaceutically acceptable salts thereof, selected from
Cyclo(-OctGly-Glu-Thr-Ala-Ser-Ile-Pro-Oic-Gl n-Lys-Thr-$^D$Pro-Pro-);
Cyclo(-OctGly-Glu-Thr-Ala-Ser-Ile-Pro-Pro-Gln-Lys-[H-γ$^4$-DiHThr-OH]-$^D$Pro-Pro-);
Cyclo(-OctGly-Glu-Thr-Ala-Ser-Ile-Pro-Pro-Gl n-Lys-Thr-$^D$Pro-$^D$Pro-);
Cyclo(-OctGly-Phe-Thr-Ala-Ser-Ile-Pro-Pro-Gln-Lys-Thr-$^D$Pro-Pro-);
Cyclo(-OctGly-Dap(Phe)-Thr-Ala-Ser-Ile-Pro-Pro-Gln-Lys-Tyr-$^D$Pro-Pro-);
Cyclo(-Dab(Octanoyl)-Glu-Thr-Ala-Ser-Ile-Pro-Pro-Gln-Lys-Thr-$^D$Pro-Pro-);
Cyclo(-Arg-Glu-Thr-Ala-Ser-Ile-Pro-Oic-Gln-Lys-Thr-$^D$Pro-Pro-);
Cyclo(-Glu(Phe)-Glu-Thr-AllylGly-Ser-Ile-Pro-Pro-Gln-Lys-Tyr-$^D$Pro-Pro-);
Cyclo(-Glu(Phe)-Glu-Thr-Ala-Ser-Ile-Pro-Pro-Gln-Lys-Tyr-$^D$Pro-Pro-);
Cyclo(-Glu(Phe)-Glu-Thr-AllylGly-Ser-Ile-Pro-Pro-Gln-Lys-Thr-$^D$Pro-Pro-).
Cyclo(-OctGly-Glu-Thr-Ala-Ser-Ile-Pro-Pro-Gln-Lys-Thr-$^D$Val-Lys-);
Cyclo(-OctGly-Glu-Thr-Ala-Ser-Ile-Pro-Pro-Gln-Lys-Thr-$^D$Tyr-Val-);
Cyclo(-OctGly-Glu-Thr-Ala-Ser-Ile-Pro-Pro-Gl n-Lys-Thr-$^D$Tyr-Lys-);
Cyclo(-OctGly-Glu-Thr-Ala-Ser-Ile-Pro-Pro-Gl n-Lys-Thr-$^D$Lys-Tyr-);
Cyclo(-OctGly-Glu-Thr-Ala-Ser-Ile-Pro-Pro-Gl n-Lys-Thr-$^D$Lys-Lys-);
Cyclo(-OctGly-Glu-Thr-Ala-Ser-Ile-Pro-Pro-Gln-Lys-Thr-$^D$Lys-Glu-);
Cyclo(-OctGly-Glu-Thr-Ala-Ser-Ile-Pro-Pro-Gln-Lys-Thr-$^D$Ser-Val-);
Cyclo(-OctGly-Glu-Thr-Ala-Ser-Ile-Pro-Pro-Gl n-Lys-Thr-$^D$Ser-Tyr-);
Cyclo(-OctGly-Glu-Thr-Ala-Ser-Ile-Pro-Pro-Gl n-Lys-Thr-$^D$Ser-Lys-);
Cyclo(-OctGly-Glu-Thr-Ala-Ser-Ile-Pro-Pro-Gl n-Lys-Thr-$^D$Pro-[H-Glu-HPro-OH]—);
Cyclo(-OctGly-Glu-Thr-Ala-Ser-Ile-Pro-Pro-Gln-Lys-Thr-$^D$Pro-$^D$Glu-);
Cyclo(-Arg-Val-Thr-Ala-Ser-Ile-Pro-Oic-Gln-Lys-Thr-$^D$Pro-$^D$Pro-);
Cyclo(-Arg-hTyr-Thr-Ala-Ser-Ile-Pro-Oic-Gln-Lys-Thr-$^D$Pro-$^D$Pro-);
Cyclo(-Arg-hTyr-Thr-Ala-Ser-Ile-Pro-Oic-Gln-Lys-Thr-$^D$Pro-Glu-);
Cyclo(-Arg-Val-Thr-Ala-Ser-Ile-Pro-Oic-Gln-Lys-Thr-$^D$Pro-Glu-).

In still another particular embodiment of the invention Xaa$^{12}$ is $^D$Pro; Gly; $^D$Ala; $^D$Val; $^D$Lys; $^D$Arg; $^D$Tyr; $^D$Ser; $^D$Glu; or Nlys; and Xaa$^{13}$ is Pro; $^D$Pro; Glu; Asp; Ala; Val; Thr; Lys; Tyr; Oic; Tic; H-β$^3$-HPro-OH; H-γ$^4$-DiHPro-OH; Nglu; or $^D$Glu.

The β-hairpin peptidomimetics of this invention can be produced, for example, by following a procedure comprising the synthesis of the linear peptide on resin. Dipeptidic amino acid residue(s) and/or amino acid residue(s) prolonged by an additional side chain with delimited length will be incorporated as amino acid building block(s) being commercially available or synthesized beforehand, as known in the art; or by following a procedure comprising the synthesis of the linear peptide on resin by applying an orthogonal protecting group strategy. For example, the amino group-bearing side chain of an amino acid residue is Alloc-protected or the like and thus prone to an individual deprotection and subsequent derivatisation to finally generate a dipeptidic amino acid residue or an amino acid residue prolonged by an additional side chain with delimited length on resin. Similarly, if, for example, the carboxylic group-bearing side chain of an amino acid residue is Allyl-protected or the like, an individual deprotection and subsequent derivatisation to finally generate a dipeptidic amino acid residue or an amino acid residue prolonged by an additional side chain with delimited length can be accomplished on resin as well.

The process of the invention can advantageously be carried out as parallel array synthesis to yield libraries of β-hairpin peptidomimetics of the above general formula I. Such parallel synthesis allows one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (D. Obrecht, J.-M. Villalgordo, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, Tetrahedron Lett. 1987, 28, 3783-3790). Linkers of this kind form amides of the carboxyl group of the amino acids; examples of resins functionalized by such linker structures include 4-[(((2,4-dimethoxy-phenyl)Fmoc-aminomethyl) phenoxyacetamido) aminomethyl] PS resin, 4-[(((2,4-dimethoxyphenyl) Fmoc-aminomethyl)phenoxy-acetamido) aminomethyl]-4-methyl-benzydrylamine PS resin (Rink amide MBHA PS Resin), and 4-[(((2,4-dimethoxy-phenyl) Fmoc-aminomethyl)phenoxyacetamido) aminomethyl] benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinyl-benzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the invention.

A number of reaction vessels equal to the total number of compounds to be synthesized by the parallel method are loaded with 25 to 1000 mg, preferably 60 mg, of the appropriate functionalized solid support, preferably 1 to 5% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, Peptides 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2: 7) for 30 min.

Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenymethyl or trityl;
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
allyl
Tse trimethylsilylethyl
Tce trichloroethyl;
for the guanidino group (as is present e.g. in the side-chain of arginine)
Pmc 2,2,5,7,8-pentamethylchroman-6-sulfonyl
Ts tosyl (i. e. p-toluenesulfonyl)
Cbz benzyloxycarbonyl
Pbf pentamethyldihydrobenzofuran-5-sulfonyl;
for the hydroxy group (as is present e.g. in the side-chain of threonine and serine)
tBu tert.-butyl
Bn benzyl
Trt trityl;

The 9-fluorenylmethoxycarbonyl-(Fmoc)-protected amino acid derivatives are preferably used as the building blocks for the construction of the β-hairpin loop mimetics of the invention. For the deprotection, i.e. cleaving off of the Fmoc group, 20% piperidine in DMF or 2% DBU/2% piperidine in DMF can be used as well as 25% hexafluoroisopropanol in $CH_2Cl_2$.

The quantity of the reactant, i. e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; Synthesis, 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,1,3,3-tetramethyluronium teraflurroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyl-uronium tetrafluoro-borate (TCTU), or hexafluorophosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-bis(tetramethylene)chlorouronium hexafluoro-phosphate (PyClU, especially for coupling N-methylated amino acids, J. Coste, E. Frerot, P. Jouin, B. Castro, *Tetrahedron Lett.* 1991, 32, 1967) or pentafluorophenyl diphenyl-phosphinate (S. Chen, J. Xu, *Tetrahedron Lett.* 1991, 32, 6711).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s) by one of the two following methods:

1) The reaction vessels are filled with solvent (preferably 5 mL), agitated for 5 to 300 minutes, preferably 15 minutes, and drained to expel the solvent;

2) The reaction vessels are filled with solvent (preferably 5 mL) and drained into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for an amino protecting group, whereas Allyl is an example for a carboxylic protecting group. Both protecting groups can be selectively removed, e.g. by means of Pd ° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced, whereas a carboxylic group can be derivatised by introduction of an amino substituent. Preferably, Alloc or Allyl will be removed by applying 0.2 eq tetrakis(triphenyl-phosphine) palladium(0) (10 mM) in dry $CH_2Cl_2$ and 10 eq phenylsilane for 15 min at room temperature. After filtration and washing of the resin the deprotection is completed by repeating the procedure with a fresh solution of reagents. In case of a liberated amino group the subsequent coupling of an appropriately protected amino acid or a carboxylic acid can be accomplished, for example, by applying the reagents/reaction conditions for amide bond formation as described above. Similarly, for example, the same reagents/reaction conditions can be applied for the coupling of an appropriately protected amino acid or an amine after liberation of a carboxylic group.

Detachment of the fully protected linear peptide from the solid support is achieved by exposing the loaded resin with a solution of the reagent used for cleavage (preferably 3 to 5 mL). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 mL of an appropriate solvent to extract (wash out) as much of the detached products as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 h, preferably about 16 h. The progress of the reaction is followed, e. g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 h, preferably about 2.5 h.

Alternatively, the detachment and complete deprotection of the fully protected peptide from the solid support can be achieved manually in glass vessels.

After full deprotection, for example, the following methods can be used for further work-up:

1) The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected peptide, cyclo(-$Xaa^1$-$Xaa^2$-$Thr^3$-$Xaa^4$-$Ser^5$-$Xaa^6$-$Xaa^7$-$Xaa^8$-$Xaa^9$-$Xaa^{10}$-$Xaa^{11}$-$Xaa^{12}$-$Xaa^{13}$-), is obtained as final product;

2) The deprotection mixture is concentrated under vacuum. Following precipitation of the fully deprotected peptide in diethylether at preferably 0° C. the solid is washed up to about 10 times, preferably 3 times, dried, and the the fully deprotected peptide, cyclo(-$Xaa^1$-$Xaa^2$-$Thr^3$-$Xaa^4$-$Ser^5$-$Xaa^6$-$Xaa^7$-$Xaa^8$-$Xaa^9$-$Xaa^{10}$-$Xaa^{11}$-$Xaa^{12}$-$Xaa^{13}$-), is obtained as final product.

Depending on its purity, the final product as obtained above can be used directly for biological assays, or has to be further purified, for example by preparative HPLC.

As mentioned earlier, it is thereafter possible, if desired, to convert the fully deprotected cyclic product thus obtained into a pharmaceutically acceptable salt or to convert a pharmaceutically acceptable, or unacceptable, salt thus obtained into the corresponding free compound or into a different, pharmaceutically acceptable, salt. Any of these operations can be carried out by methods well known in the art.

The β-hairpin peptidomimetics of the invention can be used in a wide range of applications where inflammatory diseases or pulmonary diseases or infections or immunological diseases or cardiovascular diseases or neurodegenerative diseases are mediated or resulting from serine protease activity, or where cancer is mediated or resulting from serine protease activity. For the control or prevention of a given illness or disease amenable to treatment with protease inhibitors, the β-hairpin peptidomimetics of the invention may be administered per se or may be applied as an appropriate formulation together with carriers, diluents or excipients well known in the art.

When used to treat, prevent, modulate or remodel diseases such as alpha 1 antitrypsin deficiency (AATD), pulmonary emphysema, rheumatoid arthritis, osteoarthritis, atherosclerosis, psoriaris, cystic fibrosis (CF), chronic obstructive pulmonary disease (COPD), idiopathic pulmonary fibrosis (IPF), bronchiectasis, bronchodilation, chronic bronchitis, multiple sclerosis, acute respiratory distress syndrome (ARDS), acute lung injury (ALI), pulmonary hypertension (PH), arterial pulmonary hypertension (PAH), pancreatitis, asthma, allergic rhinitis, inflammatory dermatoses, postangioplasty restenosis, systemic inflammatory respiratory syndrome (SIRS), ischemia reperfusion injury, cardiac hypertrophy, myocarditis, acute myocardial infarction (AMI), heart failure, cardiac transplant, inflammatory bowel disease (IBD), colitis, Crohn's disease, adaptive colitis or cancer such as, but not limited to, lung cancer, breast cancer, or cancer related to angiogenesis or metastasis, the β-hairpin peptidomimetics of the invention can be administered singly, as mixtures of several β-hairpin peptidomimetics, in combination with other anti-inflammatory agents, or anti-microbial agents or anti-cancer agents and/or in combination with other pharmaceutically active agents. The β-hairpin peptidomimetics of the invention can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics of the invention into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use. For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions, powders etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added. For buccal administration, the composition may take the form of tablets, lozenges, etc., formulated as known in the art.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention contain charged residues, they may be included in any of the above described formulations as such or as pharmaceutically acceptable salts. Pharmaceutically acceptable salts tend to be more soluble in aqueous and other protic solvents than are the corresponding free forms. Particularly suitable pharmaceutically acceptable salts include salts with carboxylic, phosphonic, sulfonic and sulfamic acids, e.g. acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, and other organic protonic acids, such as ascorbic acid. Suitable inorganic acids are for example hydrohalic acids, such as hydrochloric acid, sulfuric acid and phosphoric acid.

The β-hairpin peptidomimetics of the invention, or compositions thereof, will generally be used in an amount effective to achieve the intended purpose. It is to be understood that the amount used will depend on a particular application.

For topical administration to treat or prevent diseases amenable to treatment with beta hairpin mimetics a therapeutically effective dose can be determined using, for example, the in vitro assays provided in the examples. The treatment may be applied while the disease is visible, or even when it is not visible. An ordinary skilled expert will be able to determine therapeutically effective amounts to treat topical diseases without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture. Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as serine protease inhibitory agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics of the invention administered will, of course, be dependent on the subject being treated, on the subject's weight, the severity of the affliction, the manner of administration and the judgement of the prescribing physician.

Normally, a therapeutically effective dose of the β-hairpin peptidomimetics of the invention described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The present invention may also include compounds, which are identical to the compounds of the general formula cyclo(-$Xaa^1$-$Xaa^2$-$Thr^3$-$Xaa^4$-$Ser^5$-$Xaa^6$-$Xaa^7$-$Xaa^8$-$Xaa^9$-$Xaa^{10}$-$Xaa^{11}$-$Xaa^{12}$-$Xaa^{13}$-), except that one or more atoms are replaced by an atom having an atomic mass number or mass different from the atomic mass number or mass usually found in nature, e.g. compounds enriched in $^2H$ (D), $^3H$, $^{11}C$, $^{14}C$, $^{129}I$ etc. These isotopic analogs and their pharmaceutical salts and formulations are considered useful agents in the therapy and/or diagnostic, for example, but not limited to, where a fine-tuning of in vivo half-life time could lead to an optimized dosage regimen.

The following Examples illustrate the present invention but are not to be construed as limiting its scope in any way.

EXAMPLES

1. Peptide Synthesis

Coupling of the First Protected Amino Acid Residue to the Resin 1 g (1.4 mMol) 2-chlorotritylchloride resin (1.4 mMol/g; 100-200 mesh, copoly(styrene-1% DVB) polymer matrix; Barlos et al. *Tetrahedron Lett.* 1989, 30, 3943-3946) was filled into a dried flask. The resin was suspended in $CH_2Cl_2$ (5 mL) and allowed to swell at room temperature under constant shaking for 30 min. A solution of 0.98 mMol (0.7 eq) of the first suitably protected amino acid residue (see below) in $CH_2Cl_2$ (5 mL) mixed with 960 µl (4 eq) of diisopropylethylamine (DIEA) was added. After shaking the reaction mixture for 4 h at 25° C., the resin was filtered off and washed successively with $CH_2Cl_2$ (1×), DMF (1×) and $CH_2Cl_2$ (1×). A solution of $CH_2Cl_2$/MeOH/DIEA (17/2/1, 10 mL) was added to the resin and the suspension was shaken for 30 min. After filtration the resin was washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Loading was typically 0.6-0.7 mMol/g.

The following preloaded resins were prepared:

Fmoc-Ser(tBu)-O-2-chlorotrityl resin, Fmoc-Ala-O-2-chlorotrityl resin, Fmoc-Pro-O-2-chlorotrityl resin and Fmoc-Oic-O-2-chlorotrityl resin.

The synthesis was carried out employing a Syro-peptide synthesizer (MultiSynTech) using 24-96 reaction vessels. In each vessel 0.04 mMol of the above resin was placed and the resin was swollen in $CH_2Cl_2$ and DMF for 15 min, respectively. The following reaction cycles were programmed and carried out:

| Step | Reagent | Time |
|------|---------|------|
| 1 | DMF, wash | 5 × 1 min |
| 2 | 20% piperidine/DMF | 1 × 5 min, 1 × 15 min |
| 3 | DMF, wash | 5 × 1 min |
| 4 | 3.6 eq Fmoc amino acid, 3.6 eq HOAt/DMF + 3.6 eq DIC/DMF | 1 × 40 min |
| 5 | DMF, wash | 1 × 1 min |
| 6 | 3.6 eq Fmoc amino acid, 3.6 eq HOAt/DMF + 3.6 eq HATU + 7.2 eq DIPEA | 1 × 40 min |

Unless indicated otherwise, the final coupling of an amino acid was followed by Fmoc deprotection by applying steps 1-3 of the above described reaction cycle.

The appropriately protected amino acid building blocks are commercially available or can be synthesized as known in the art.

Attachment of Carboxylic Acids or Amino Acids to Amino Group- or Carboxylic Group-Bearing Side Chains Procedure A Attachment of Carboxylic Acids or Amino Acids to Selectively Deprotected Linear Peptides on Resin:

To remove alloc-protecting groups from amino functions or allyl-protecting groups from carboxy functions present in the resin bound peptide the latter (0.04 mMol) was swollen in freshly distilled $CH_2Cl_2$ for at least 15 min followed by adding 0.2 eq tetrakis(triphenyl-phosphine)palladium(0) (10 mM) in dry $CH_2Cl_2$ and 10 eq phenylsilane. After shaking the reaction mixture for 15 min at room temperature, the resin was filtered off and a fresh solution of reagents was added to repeat the procedure. Following subsequent washing of the resin with $CH_2Cl_2$, DMF and $Et_2O$, the resin was swollen again in $CH_2Cl_2$ and the attachment of a carboxylic acid or appropriately protected amino acid was accomplished by subsequently adding a mixture of 3.6 eq of the desired acid and 3.6 eq HOAt dissolved in DMF and 3.6 eq DIC dissolved in DMF allowing the reaction mixture to stand for 1 h disrupted only by occasionally stirring. After filtration and washing of the resin three times with DMF, the coupling was completed by repeating the procedure with a fresh solution of a mixture of 3.6 eq of the same desired acid and 3.6 eq HOAt dissolved in DMF and a mixture of 3.6 eq HATU and 7.2 eq DIPEA in DMF.

In case of amino group-bearing side chains the acids used to be coupled by the above described protocol were octanoic acid or N-Boc protected phenylalanine, in case of carboxy group-bearing side chains the acid coupled by the above described protocol was phenylalanine the carboxy group being protected by tBu.

Cyclization and Work Up of Backbone Cyclized Peptides

Cleavage of the Fully Protected Peptide Fragment

After completion of the synthesis, the resin (0.04 mMol) was suspended in 1 mL (0.13 mMol, 3.4 eq) of 1% TFA in $CH_2Cl_2$ (v/v) for 3 minutes, filtered, and the filtrate was neutralized with 1 mL (0.58 mMol, 14.6 eq) of 10% DIEA in $CH_2Cl_2$ (v/v). This procedure was repeated three times to ensure completion of the cleavage. The filtrate was evaporated to dryness and a sample of the product was fully deprotected by using a cleavage mixture containing 95% trifluoroacetic acid (TFA), 2.5% water and 2.5% triisopropylsilane (TIS) to be analyzed by reverse phase-HPLC ($C_{18}$ column) and ESI-MS to monitor the efficiency of the linear peptide synthesis.

Cyclization of the Linear Peptide

The fully protected linear peptide (0.04 mMol) was dissolved in DMF (4 Mol/mL). Then 30.4 mg (0.08 mMol, 2 eq) of HATU, 10.9 mg (0.08 mMol, 2 eq) of HOAt and 28 µl (0.16 mMol, 4 eq) DIEA were added, and the mixture was vortexed at 25° C. for 16 hours and subsequently concentrated under high vacuum. The residue was partitioned between $CH_2Cl_2$ and $H_2O$/$CH_3CN$ (90/10: v/v). The $CH_2Cl_2$ phase was evaporated to yield the fully protected cyclic peptide.

Full Deprotection of the Cyclic Peptide

The cyclic peptide obtained was dissolved in 3 mL of the cleavage mixture containing 82.5% trifluoroacetic acid (TFA), 5% water, 5% thioanisole, 5% phenol and 2.5% ethanedithiole (EDT). The mixture was allowed to stand at 25° C. for 2.5 hours and thereafter concentrated under vacuum. After precipitation of the cyclic fully deprotected peptide in diethylether ($Et_2O$) at 0° C. the solid was washed twice with $Et_2O$ and dried.

After purification of the crude products via preparative HPLC the peptides were 20 lyophilized (white powders) and analysed by the following analytical methods:

Analytical Method A for Examples 1-17, 19, 39-49

Analytical HPLC retention times (RT, in minutes) were determined using a Ascentis Express C18 column, 50×3.0 mm, (cod. 53811-U-Supelco) with the following solvents A ($H_2O$+0.1% TFA) and B ($CH_3CN$+0.01% TFA) and the gradient: 0-0.05 min: 97% A, 3% B; 4.95 min: 3% A, 97% B; 5.35 min: 3% A, 97% B; 5.40 min: 97% A, 3% B. Flow rate=1.3 mL/min; UV_Vis=220 nm.

Analytical Method B for Example 18

Analytical HPLC retention times (RT, in minutes) were determined using a Ascentis Express C18 column, 50×3.0 mm, (cod. 53811-U-Supelco) with the following solvents A (H$_2$O+0.1% TFA) and B (CH$_3$CN+0.01% TFA) and the gradient: 0-0.05 min: 97% A, 3% B; 3.40 min: 33% A, 67% B; 3.45 min: 3% A, 97% B; 3.65 min: 3% A, 97% B; 3.70 min: 97% A, 3% B. Flow rate=1.3 mL/min; UV_Vis=220 nm.

Analytical Method C for Examples 20-38

Analytical HPLC retention times (RT, in minutes) were determined using a Xselect CSH C18 XP column, 100×3.0 mm, (cod. 186006107, Waters) with the following solvents A (H$_2$O+0.1% TFA) and B (CH$_3$CN+0.01% TFA) and the gradient: 0-0.05 min: 95% A, 5% B; 10.05 min: 3% A, 97% B; 12.05 min: 3% A, 97% B; 12.10 min: 95% A, 5% B. Flow rate=0.6 mL/min; UV_Vis=220 nm.

Examples 1-13, 16, 20, 22, 25-33, 35-37, 43, 47, 48 are shown in Table 1. The peptides were synthesized as follows: Starting resin was Fmoc-Ser(tBu)-O-2-chlorotrityl resin, which was prepared as described above. To that resin Xaa$^4$, finally at position 4, was grafted. The linear peptide was synthesized on solid support according to the procedure described above in the following sequence: Resin-Ser$^5$-Xaa$^4$-Thr$^3$-Xaa$^2$-Xaa$^1$-Xaa$^{13}$-Xaa$^{12}$-Xaa$^{11}$-Xaa$^{10}$-Xaa$^9$-Xaa$^8$-Xaa$^7$-Xaa$^6$.

Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Example 14 is shown in Table 1. The peptide was synthesized as follows: Starting resin was Fmoc-Ser(tBu)-O-2-chlorotrityl resin, which was prepared as described above. To that resin Xaa$^4$, finally at position 4, was grafted. The linear peptide was synthesized on solid support according to the procedure described above in the following sequence: Resin-Ser$^5$-Xaa$^4$-Thr$^3$-Dap$^2$-Xaa$^1$-Xaa$^{13}$-Xaa$^{12}$-Xaa$^{11}$-Xaa$^{10}$-Xaa$^9$-Xaa$^8$-Xaa$^7$-Xaa$^6$. Before the last Fmoc-deprotection procedure A was applied to attach phenylalanine to the side chain of Dap$^2$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Example 15 is shown in Table 1. The peptide was synthesized as follows: Starting resin was Fmoc-Ser(tBu)-O-2-chlorotrityl resin, which was prepared as described above. To that resin Xaa$^4$, finally at position 4, was grafted. The linear peptide was synthesized on solid support according to the procedure described above in the following sequence: Resin-Ser$^5$-Xaa$^4$-Thr$^3$-Xaa$^2$-Dab$^1$-Xaa$^{13}$-Xaa$^{12}$-Xaa$^{11}$-Xaa$^{10}$-Xaa$^9$-Xaa$^8$-Xaa$^7$-Xaa$^6$. Before the last Fmoc-deprotection procedure A was applied to attach octanoic acid to the side chain of Dab$^1$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Examples 17-19 are shown in Table 1. The peptides were synthesized as follows: Starting resin was Fmoc-Ser(tBu)-O-2-chlorotrityl resin, which was prepared as described above. To that resin Xaa$^4$, finally at position 4, was grafted. The linear peptide was synthesized on solid support according to the procedure described above in the following sequence: Resin-Ser$^5$-Xaa$^4$-Thr$^3$-Xaa$^2$-Glu$^1$-Xaa$^{13}$-Xaa$^{12}$-Xaa$^{11}$-Xaa$^{10}$-Xaa$^9$-Xaa$^8$-Xaa$^7$-Xaa$^6$. Before the last Fmoc-deprotection procedure A was applied to attach phenylalanine to the side chain of Glu$^1$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Examples 21, 23, 24 are shown in Table 1. The peptides were synthesized as follows: Starting resin was Fmoc-Ala-O-2-chlorotrityl resin, which was prepared as described above. To that resin Thr$^3$, finally at position 3, was grafted. The linear peptide was synthesized on solid support according to the procedure described above in the following sequence: Resin-Ala$^4$-Thr$^3$-Xaa$^2$-Xaa$^1$-Xaa$^{13}$-Xaa$^{12}$-Xaa$^{11}$-Xaa$^{10}$-Xaa$^9$-Xaa$^8$-Xaa$^7$-Xaa$^6$-Ser$^5$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Examples 34, 38, 45, 46 are shown in Table 1. The peptides were synthesized as follows: Starting resin was Fmoc-Pro-O-2-chlorotrityl resin, which was prepared as described above. To that resin Xaa$^{12}$, finally at position 12, was grafted. The linear peptide was synthesized on solid support according to the procedure described above in the following sequence: Resin-Pro$^{13}$-Xaa$^{12}$-Xaa$^{11}$-Xaa$^{10}$-Xaa$^9$-Xaa$^8$-Xaa$^7$-Xaa$^6$-Ser$^5$-Xaa$^4$-Thr$^3$-Xaa$^2$-Xaa$^1$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Examples 39, 40, 49 are shown in Table 1. The peptides were synthesized as follows: Starting resin was Fmoc-Pro-O-2-chlorotrityl resin, which was prepared as described above. To that resin Xaa$^7$, finally at position 7, was grafted. The linear peptide was synthesized on solid support according to the procedure described above in the following sequence: Resin-Pro$^8$-Xaa$^7$-Xaa$^6$-Ser$^5$-Xaa$^4$-Thr$^3$-Xaa$^2$-Xaa$^1$-Xaa$^{13}$-Xaa$^{12}$-Xaa$^{11}$-Xaa$^{10}$-Xaa$^9$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

Examples 41, 42, 44 are shown in Table 1. The peptides were synthesized as follows: Starting resin was Fmoc-Oic-O-2-chlorotrityl resin, which was prepared as described above. To that resin Xaa$^7$, finally at position 7, was grafted. The linear peptide was synthesized on solid support according to the procedure described above in the following sequence: Resin-Oic$^8$-Xaa$^7$-Xaa$^6$-Ser$^5$-Xaa$^4$-Thr$^3$-Xaa$^2$-Xaa$^1$-Xaa$^{13}$-Xaa$^{12}$-Xaa$^{11}$-Xaa$^{10}$-Xaa$^9$. Following a final Fmoc deprotection as described above, the peptide was cleaved from the resin, cyclized, deprotected and purified as indicated above.

The HPLC-retention times and UV-purities, determined using the analytical methods as described above, are shown in Table 1.

TABLE 1

Examples

| Ex. | Xaa¹ᵃ⁾ | Xaa²ᵃ⁾ | Xaa³ᵃ⁾ | Xaa⁴ᵃ⁾ | Xaa⁵ᵃ⁾ | Xaa⁶ᵃ⁾ | Xaa⁷ᵃ⁾ | Xaa⁸ᵃ⁾ | Xaa⁹ᵃ⁾ |
|---|---|---|---|---|---|---|---|---|---|
| 1 | OctGly | Glu | Thr | Ala | Ser | Ile | Pro | Pro | Gln |
| 2 | OctGly | Glu | Thr | Ala | Ser | Ile | Pro | Pro | Gln |
| 3 | OctGly | Glu | Thr | Ala | Ser | Ile | Pro | Pro | Gln |
| 4 | OctGly | Glu | Thr | Ala | Ser | Ile | Pro | Pro | Gln |
| 5 | OctGly | Glu | Thr | Ala | Ser | Ile | Pro | Pro | Gln |
| 6 | OctGly | Glu | Thr | Ala | Ser | Ile | Pro | Pro | Gln |
| 7 | OctGly | Glu | Thr | Ala | Ser | Ile | Nglu | Pro | Gln |
| 8 | OctGly | Glu | Thr | Ala | Ser | Ile | Pro | Pro | Gln |
| 9 | Dab(Phe) | Glu | Thr | Ala | Ser | Ile | Pro | Pro | Gln |
| 10 | OctGly | Glu | Thr | Ala | Ser | Ile | Pro | Oic | Gln |
| 11 | OctGly | Glu | Thr | Ala | Ser | Ile | Pro | Pro | Gln |
| 12 | OctGly | Glu | Thr | Ala | Ser | Ile | Pro | Pro | Gln |
| 13 | OctGly | Phe | Thr | Ala | Ser | Ile | Pro | Pro | Gln |
| 14 | OctGly | Dap(Phe) | Thr | Ala | Ser | Ile | Pro | Pro | Gln |
| 15 | Dab(Oct)ᶜ⁾ | Glu | Thr | Ala | Ser | Ile | Pro | Pro | Gln |
| 16 | Arg | Glu | Thr | Ala | Ser | Ile | Pro | Oic | Gln |
| 17 | Glu(Phe) | Glu | Thr | AllyGly | Ser | Ile | Pro | Pro | Gln |
| 18 | Glu(Phe) | Glu | Thr | Ala | Ser | Ile | Pro | Pro | Gln |
| 19 | Glu(Phe) | Glu | Thr | AllyGly | Ser | Ile | Pro | Pro | Gln |
| 20 | OctGly | Glu | Thr | Ala | Ser | Ile | Pro | Pro | Gln |
| 21 | OctGly | Glu | Thr | Ala | Ser | Ile | Pro | Pro | Gln |
| 22 | OctGly | Glu | Thr | Ala | Ser | Ile | Pro | Pro | Gln |
| 23 | OctGly | Glu | Thr | Ala | Ser | Ile | Pro | Pro | Gln |
| 24 | OctGly | Glu | Thr | Ala | Ser | Ile | Pro | Pro | Gln |
| 25 | OctGly | Glu | Thr | Ala | Ser | Ile | Pro | Pro | Gln |
| 26 | OctGly | Glu | Thr | Ala | Ser | Ile | Pro | Pro | Gln |
| 27 | OctGly | Glu | Thr | Ala | Ser | Ile | Pro | Pro | Gln |
| 28 | OctGly | Glu | Thr | Ala | Ser | Ile | Pro | Pro | Gln |
| 29 | OctGly | Glu | Thr | Ala | Ser | Ile | Pro | Pro | Gln |
| 30 | OctGly | Glu | Thr | Ala | Ser | Ile | Pro | Pro | Gln |
| 31 | OctGly | Glu | Thr | Ala | Ser | Ile | Pro | Pro | Gln |
| 32 | OctGly | Glu | Thr | Ala | Ser | Ile | Pro | Pro | Gln |
| 33 | OctGly | Glu | Thr | Ala | Ser | Ile | Nlys | Pro | Gln |
| 34 | OctGly | Glu | Thr | Ala | Ser | Ile | Pro | Nglu | Gln |
| 35 | OctGly | Glu | Thr | Ala | Ser | Ile | Pro | Nlys | Gln |
| 36 | OctGly | Glu | Thr | Ala | Ser | Ile | Pro | Pro | β³-Glnᶜ⁾ |
| 37 | OctGly | Glu | Thr | Ala | Ser | Ile | Pro | Pro | Gln |
| 38 | OctGly | Glu | Thr | Ala | Ser | Ile | Pro | Pro | Gln |
| 39 | OctGly | Glu | Thr | Ala | Ser | Ile | Pro | Pro | Gln |
| 40 | OctGly | Glu | Thr | Ala | Ser | Ile | Pro | Pro | Gln |
| 41 | Arg | Val | Thr | Ala | Ser | Ile | Pro | Oic | Gln |
| 42 | Arg | hTyr | Thr | Ala | Ser | Ile | Pro | Oic | Gln |
| 43 | Arg | hTyr | Thr | Ala | Ser | Ile | Pro | Oic | Gln |
| 44 | Arg | Val | Thr | Ala | Ser | Ile | Pro | Oic | Gln |
| 45 | OctGly | Glu | Thr | Ala | Ser | Ile | Pro | Pip | Gln |
| 46 | OctGly | Glu | Thr | Ala | Ser | Ile | Pro | Azt | Gln |
| 47 | OctGly | hTyr | Thr | Ala | Ser | Ile | Pro | Pro | Gln |
| 48 | OctGly | hTyr | Thr | Ala | Ser | Ile | Pro | Pro | Gln |
| 49 | Arg | hTyr | Thr | Ala | Ser | Ile | Pro | Pro | Gln |

| Ex. | Xaa¹⁰ᵃ⁾ | Xaa¹¹ᵃ⁾ | Xaa¹²ᵃ⁾ | Xaa¹³ᵃ⁾ | Purity [%] | MSᵇ⁾ | RT [min] |
|---|---|---|---|---|---|---|---|
| 1 | Lys | hSer(Me) | ᴰPro | Pro | 85 | 1430.8 | 2.53 |
| 2 | Lys | Dap | ᴰPro | Pro | 72 | 701.5 | 2.14 |
| 3 | Lys | alloThr | ᴰPro | Pro | 80 | 1416.8 | 2.35 |
| 4 | Lys | hSer | ᴰPro | Pro | 71 | 1416.8 | 2.37 |
| 5 | Lys | hGln | ᴰPro | Pro | 71 | 1457.8 | 2.29 |
| 6 | Lys | Thr | ᴰPro | Oic | 77 | 1470.8 | 2.73 |
| 7 | Lys | Thr | ᴰPro | Pro | 71 | 1448.8 | 2.41 |
| 8 | Lys | γ⁴-Tyrᶜ⁾ | ᴰPro | Pro | 85 | 1506.8 | 2.57 |
| 9 | Lys | Tyr | ᴰPro | Pro | 74 | 779.0 | 1.72 |
| 10 | Lys | Thr | ᴰPro | Pro | 77 | 1470.8 | 2.56 |
| 11 | Lys | γ⁴-Thrᶜ⁾ | ᴰPro | Pro | 70 | 1444.8 | 2.41 |
| 12 | Lys | Thr | ᴰPro | ᴰPro | 88 | 1416.8 | 2.30 |
| 13 | Lys | Thr | ᴰPro | Pro | 88 | 718.0 | 2.64 |
| 14 | Lys | Tyr | ᴰPro | Pro | 75 | 1584.0 | 2.52 |
| 15 | Lys | Thr | ᴰPro | Pro | 71 | 1473.8 | 2.25 |
| 16 | Lys | Thr | ᴰPro | Pro | 83 | 1457.8 | 1.78 |
| 17 | Lys | Tyr | ᴰPro | Pro | 72 | 1612.8 | 2.21 |
| 18 | Lys | Tyr | ᴰPro | Pro | 85 | 1587.2 | 2.07ᵈ⁾ |
| 19 | Lys | Thr | ᴰPro | Pro | 77 | 1550.8 | 2.12 |

TABLE 1-continued

| | | | Examples | | | |
|---|---|---|---|---|---|---|
| 20 | Lys | Thr | $^D$Ala | Ala | 95 | 1364.8 | 4.69$^{e)}$ |
| 21 | Lys | Thr | $^D$Val | Tyr | 95 | 1484.7 | 5.17$^{e)}$ |
| 22 | Lys | Thr | $^D$Val | Lys | 95 | 1450.0 | 4.26$^{e)}$ |
| 23 | Lys | Thr | $^D$Tyr | Val | 95 | 1484.6 | 5.17$^{e)}$ |
| 24 | Lys | Thr | $^D$Tyr | Tyr | 95 | 1548.8 | 4.96$^{e)}$ |
| 25 | Lys | Thr | $^D$Tyr | Lys | 84 | 1513.8 | 4.20$^{e)}$ |
| 26 | Lys | Thr | $^D$Lys | Val | 94 | 1450.0 | 4.33$^{e)}$ |
| 27 | Lys | Thr | $^D$Lys | Tyr | 95 | 1514.0 | 4.36$^{e)}$ |
| 28 | Lys | Thr | $^D$Lys | Lys | 95 | 1479.0 | 3.74$^{e)}$ |
| 29 | Lys | Thr | $^D$Lys | Glu | 83 | 1480.0 | 4.08$^{e)}$ |
| 30 | Lys | Thr | $^D$Ser | Val | 95 | 1408.7 | 4.83$^{e)}$ |
| 31 | Lys | Thr | $^D$Ser | Tyr | 91 | 1472.8 | 4.72$^{e)}$ |
| 32 | Lys | Thr | $^D$Ser | Lys | 95 | 1437.8 | 4.02$^{e)}$ |
| 33 | Lys | Thr | $^D$Pro | Pro | 67 | 724.4 | 4.79$^{e)}$ |
| 34 | Lys | Thr | $^D$Pro | Pro | 81 | 724.9 | 5.07$^{e)}$ |
| 35 | Lys | Thr | $^D$Pro | Pro | 88 | 724.4 | 4.69$^{e)}$ |
| 36 | Lys | Thr | $^D$Pro | Pro | 95 | 1430.7 | 5.19$^{e)}$ |
| 37 | $\beta^3$-Lys$^{c)}$ | Thr | $^D$Pro | Pro | 55 | 1430.7 | 5.03$^{e)}$ |
| 38 | $\gamma^4$-Lys$^{c)}$ | Thr | $^D$Pro | Pro | 85 | 1444.7 | 5.13$^{e)}$ |
| 39 | Lys | Thr | $^D$Pro | $\beta^3$-Pro$^{c)}$ | 74 | 1432 | 2.22 |
| 40 | Lys | Thr | $^D$Pro | $^D$Glu | 95 | 1449.1 | 2.31 |
| 41 | Lys | Thr | $^D$Pro | Pro | 87 | 1427.8 | 2.09 |
| 42 | Lys | Thr | $^D$Pro | Pro | 92 | 1506.1 | 2.02 |
| 43 | Lys | Thr | $^D$Pro | Glu | 70 | 1539.1 | 1.95 |
| 44 | Lys | Thr | $^D$Pro | Glu | 70 | 1460.1 | 1.97 |
| 45 | Lys | Thr | $^D$Pro | Pro | 74 | 1431.1 | 2.28 |
| 46 | Lys | Thr | $^D$Pro | Pro | 80 | 702.2 | 2.49 |
| 47 | Lys | Ser | $^D$Pro | Pro | 85 | 1451.0 | 2.55 |
| 48 | Lys | Asn | $^D$Pro | Pro | 86 | 1479.0 | 2.46 |
| 49 | Lys | Thr | $^D$Pro | Glu | 70 | 1484.0 | 1.76 |

$^{a)}$Abbreviations of amino acid see listing above.
$^{b)}$MS: either [M + 1H]$^{1+}$ or [M + 2H]$^{2+}$.
$^{c)}\gamma^4$-Tyr = H-$\gamma^4$-DiHTyr-OH; $\gamma^4$-Thr = H-$\gamma^4$-DiHThr-OH; Dab(Oct) = Dab(Octanoyl); $\beta^3$-Gln = H-$\beta^3$-HGln-OH; $\beta^3$-Lys = H-$\beta^3$-HLys-OH; $\gamma^4$-Lys = H-$\gamma^4$-DiHLys-OH; $\beta^3$-Pro = H-$\beta^3$-HPro-OH;
$^{d)}$Analytical method B
$^{e)}$Analytical method C 2. Biological Methods 2.1 Preparation of the Peptide Samples Lyophilized peptides were weighed on a Microbalance (Mettler MT5) and dissolved in DMSO to a final concentration of 10 mM. Stock solutions were kept at +4° C., light protected. The biological assays were carried out under assay conditions having less than 1% DMSO unlike indicated otherwise.

2.2 Inhibition of Human Neutrophil Elastase

The ability of the peptides of the invention to inhibit the hydrolysis activity of human neutrophil elastase (Serva Electrophoresis, Germany) using the synthetic tetrapeptidic substrate MeOSuc-AAPV-pNA (Bachem, Switzerland) was determined as follows:

The above substrate (0.3 mM) and human neutrophil elastase (10 nM) were incubated at 37° C. with serial dilutions of the peptides (1% DMSO final) in assay buffer (50 mM Tris, pH 8, 300 mM NaCl, 0.01% Tween20). The release of pNA was followed by monitoring the change in absorbance at 405 nm for 30 minutes. Control assays with the same assay set-up as above, but without peptide, ran linearly. The dose-response data were fitted to the 4-parameter Hill equation providing the IC$_{50}$ value using Graphpad (Prism 5).

2.3 Inhibition of Porcine Pancreatic Elastase

The ability of the peptides of the invention to inhibit the hydrolysis activity of porcine pancreatic elastase (Sigma, USA) using the synthetic tripeptidic substrate MeOSuc-AAA-pNA (Bachem, Switzerland) was determined as follows:

The above substrate (1 mM) and human porcine pancreatic elastase (15 nM) were incubated at 37° C. with serial dilutions of the peptides (0.5% DMSO final) in assay buffer (50 mM Tris, pH8, 100 mM NaCl, 0.01% Tween20). The release of pNA was followed by monitoring the change in absorbance at 405 nm for 30 minutes. Control assays with the same assay set-up as above, but without peptide, ran linearly. The dose-response data were fitted to the 4-parameter Hill equation providing the IC$_{50}$ value using Graphpad (Prism 5).

2.4 Inhibition of Human Proteinase 3

The inactivation of human proteinase 3 (Elastin Products Company, USA) by the peptides of the invention using synthetic tripeptidic substrate Boc-Ala-Ala-Nva-SBzl (Elastin Products Company, USA) was determined as follows:

The above substrate (1 mM), 4,4'-dithiodipyridine (250 µM) and human proteinase 3 (10 nM) were incubated at 37° C. with serial dilutions of the peptides (0.5% DMSO final) in assay buffer (50 mM Tris, pH7.4, 150 mM NaCl, 0.01% Tween20). The reaction process was followed by monitoring the change in absorbance at 340 nm for 30 minutes. Control assays with the same assay set-up as above, but without peptide, ran linearly. The dose-response data were fitted to the 4-parameter Hill equation providing the IC$_{50}$ value using Graphpad (Prism 5).

3. Results

The results of the experiments described under 2.2-2.4, above, are indicated in Table 2 herein below.

TABLE 2

| Ex. | Human neutrophil elastase (hNE) IC$_{50}$ [nM] | hNE IC$_{50}$ SD [nM] | Porcine pancreatic elastase (PPE) IC$_{50}$ [µM] | PPE IC$_{50}$ SD [µM] | Human proteinase 3 (hPr3) IC$_{50}$ [µM] | hPr3 IC$_{50}$ SD [µM] | hNE/PPE selectivity | hNE/hPr3 selectivity |
|---|---|---|---|---|---|---|---|---|
| 1 | 4.8 | 1.2 | 0.62 | 0.10 | 0.72 | 0.44 | 129 | 150 |
| 2 | 5.5 | 0.7 | 1.20 | 0.44 | 3.54 | 1.07 | 218 | 644 |
| 3 | 6.8 | 1.1 | 1.42 | 0.03 | 1.01 | 0.41 | 209 | 149 |
| 4 | 8.6 | 2.8 | 1.35 | 0.01 | 1.02 | 0.13 | 157 | 119 |
| 5 | 9.9 | 2.1 | 1.59 | 0.33 | 2.35 | 0.80 | 161 | 237 |
| 6 | 12 | 4.9 | 3.85 | 0.63 | 4.46 | 3.07 | 321 | 372 |
| 7 | 13.3 | 3.7 | 3.92 | 0.88 | 4.06 | 1.27 | 295 | 305 |
| 8 | 19.8 | 9.6 | 1.81 | 0.08 | 3.33 | 0.47 | 91 | 168 |
| 9 | 17.3 | 1.0 | 3.72 | 0.34 | 12.3 | 3.5 | 215 | 711 |
| 10 | 7.3 | 0.4 | 36.2 | 1.8 | >100 | n.d. | 4959 | >13699 |
| 11 | 11.5 | 2.9 | 48.5 | 6.3 | 21.1 | 12.5 | 4217 | 1835 |
| 12 | 15.2 | 5.7 | >100 | n.d. | >100 | n.d. | >6579 | >6579 |
| 13 | 10.1 | 1.0 | 21.4 | 0.6 | >100 | n.d. | 2119 | >9901 |
| 14 | 15 | 9.5 | 5.5 | 1.1 | 26 | 0.7 | 367 | 1733 |
| 15 | 19.1 | 3.2 | 92.8 | 15 | 45.2 | 19.9 | 4859 | 2366 |
| 16 | 15 | 8.1 | >100 | n.d. | >100 | n.d. | >6667 | >6667 |
| 17 | 15 | 1.3 | 31.2 | 0.1 | 60.2 | 13.3 | 2080 | 4013 |
| 18 | 15.9 | 5.4 | 74.1 | 12 | 46.2 | 23.2 | 4660 | 2906 |
| 19 | 33 | 5.7 | >100 | n.d. | >100 | n.d. | >3030 | >3030 |
| 20 | 13.3 | 9.3 | 28.3 | 0.1 | 8.9 | 5.4 | 2128 | 669 |
| 21 | 12.9 | 7.9 | 10.6 | 0.2 | 13.0 | 1.9 | 822 | 1008 |
| 22 | 12.4 | 11.6 | 60.1 | 4.5 | 70.4 | 23.5 | 4847 | 5677 |
| 23 | 6.0 | 3.7 | 10.3 | 2.1 | 10.3 | 3.3 | 1717 | 1717 |
| 24 | 11.6 | 3.9 | 12.9 | 0.3 | 7.7 | 4.7 | 1112 | 664 |
| 25 | 6.4 | 1.9 | 45.0 | 0.7 | 41.8 | 21.9 | 7031 | 6531 |
| 26 | 10.6 | 8.3 | 46.8 | 8.1 | 5.0 | 0.2 | 4415 | 472 |
| 27 | 10.1 | n.d. | 44.1 | 4.0 | 39.6 | n.d. | 4366 | 3921 |
| 28 | 12.0 | 4.6 | >100 | n.d. | >100 | n.d. | >8333 | >8333 |
| 29 | 11.8 | 7.9 | 12.8 | 1.6 | 62.6 | 3.7 | 1085 | 5305 |
| 30 | 12.0 | 10.1 | 51.2 | 11.2 | 14.3 | 10.1 | 4267 | 1192 |
| 31 | 22.9 | 1.0 | 52.1 | 7.1 | 32.8 | 19.4 | 2275 | 1432 |
| 32 | 22.3 | 8.5 | 90.0 | 4.1 | >100 | n.d. | 4036 | >4484 |
| 33 | 7.0 | 4.0 | 8.3 | 1.1 | 6.1 | 1.8 | 1186 | 871 |
| 34 | 30.3 | 15.1 | 15.5 | 0.3 | 5.2 | 1.7 | 512 | 172 |
| 35 | 7.7 | 7.3 | 1.6 | 0.8 | 1.5 | 0.4 | 208 | 195 |
| 36 | 16.2 | 6.4 | 11.1 | 0.9 | 5.9 | 0.9 | 685 | 364 |
| 37 | 41.5 | 32.5 | 8.8 | 0.5 | 15.4 | 2.1 | 212 | 371 |
| 38 | 17.2 | 10.1 | 9.2 | 0.6 | 9.2 | 3.1 | 535 | 535 |
| 39 | 2.9 | 0.1 | 87.9 | 13.6 | 71.5 | 26.0 | 30310 | 24655 |
| 40 | 1.3 | 0.2 | >100 | n.d. | >100 | n.d. | >76923 | >76923 |
| 41 | 7.9 | 2.8 | >100 | n.d. | >100 | n.d. | >12658 | >12658 |
| 42 | 4.8 | 3.1 | >100 | n.d. | >100 | n.d. | >20833 | >20833 |
| 43 | 2.7 | 1.9 | >100 | n.d. | >100 | n.d. | >237037 | >237037 |
| 44 | 9.6 | 4.9 | >100 | n.d. | >100 | n.d. | >10417 | >10417 |
| 45 | 7.1 | 1.9 | 2.3 | 0.5 | 0.9 | 0.4 | 324 | 127 |
| 46 | 7.1 | 5.5 | 1.9 | 0.1 | 2.2 | 0.1 | 268 | 310 |
| 47 | 1.4 | 0.2 | 0.5 | 0.3 | 1.0 | 0.2 | 357 | 714 |
| 48 | 2.7 | 1.0 | 0.4 | 0.3 | 1.1 | 0.7 | 148 | 407 |
| 49 | 15.3 | 6.4 | 38.1 | 1.6 | 9.6 | 7.1 | 2490 | 627 | n.d. = not determined

The invention claimed is:

1. A backbone cyclized peptidic compound, built up from 13 amino acid residues, of the general formula

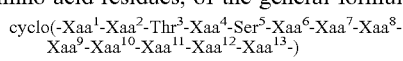

and pharmaceutically acceptable salts thereof, wherein

Xaa$^1$ is OctGly; Dab(Phe); Arg; Dab(Octanoyl); or Glu(Phe);
Xaa$^2$ is Glu; Phe; Dap(Phe); Val; or hTyr;
Xaa$^4$ is Ala; or AllylGly;
Xaa$^6$ is Ile;
Xaa$^7$ is Pro; Nglu; or Nlys;
Xaa$^8$ is Pro; Nglu; Nlys; Pip; Azt; or Oic;
Xaa$^9$ is Gln; or H-β$^3$-HGln-OH;
Xaa$^{10}$ is Lys; H-β$^3$-HLys-OH; or H-γ$^4$-DiHLys-OH;
Xaa$^{11}$ is hSer; hSer(Me); Thr; alloThr; hGln; Dap; Tyr; or H-γ$^4$-DiHTyr-OH; H-γ$^4$-DiHThr-OH; Ser; or Asn;
Xaa$^{12}$ is $^D$Pro; $^D$Ala; $^D$Val; $^D$Tyr; $^D$Lys; or $^D$Ser; and
Xaa$^{13}$ is Pro; $^D$Pro; Oic; Ala; Tyr; Val; Lys; H-β$^3$-HPro-OH; $^D$Glu; or Glu;
with the proviso that
Xaa$^1$ is Dab(Phe); Dab(Octanoyl); or Glu(Phe); and/or
Xaa$^7$ is Nglu; or Nlys; and/or
Xaa$^8$ is Nglu; Nlys; Pip; Azt; or Oic; and/or
Xaa$^9$ is H-β$^3$-HGln-OH; and/or
Xaa$^{10}$ is H-β$^3$-HLys-OH; or H-γ$^4$-DiHLys-OH; and/or
Xaa$^{11}$ is H-γ$^4$-DiHTyr-OH; or H-γ$^4$-DiHThr-OH; and/or
Xaa$^{12}$ is $^D$Ala; $^D$Val; $^D$Tyr; $^D$Lys; or $^D$Ser; and/or
Xaa$^{13}$ is $^D$Pro; Oic; H-β$^3$-HPro-OH; or $^D$Glu;
and with the further proviso that
if Xaa$^{11}$ is Tyr, then
Xaa$^1$ is Dab(Phe); Arg; or Glu(Phe);
and/or
Xaa$^2$ is Dap(Phe).

2. A compound according to claim 1 of the formula I wherein
Xaa¹ is OctGly; or Dab(Phe);
Xaa² is Glu;
Xaa⁴ is Ala;
Xaa⁶ is Ile;
Xaa⁷ is Pro; Nglu; or Nlys;
Xaa⁸ is Pro; Nglu; Nlys; Pip; or Azt;
Xaa⁹ is Gln; or H-β³-HGln-OH;
Xaa¹⁰ is Lys; H-β³-HLys-OH; or H-γ⁴-DiHLys-OH;
Xaa¹¹ is hSer; hSer(Me); Thr; alloThr; hGln; Dap; Tyr; or H-γ⁴-DiHTyr-OH;
Xaa¹² is $^D$Pro; $^D$Ala; $^D$Val; $^D$Tyr; or $^D$Lys; and
Xaa¹³ is Pro; Oic; Ala; Tyr; or Val;
with the proviso that
Xaa¹ is Dab(Phe); and/or
Xaa⁷ is Nglu; or Nlys; and/or
Xaa⁸ is Nglu; Nlys; Pip; or Azt; and/or
Xaa⁹ is H-β³-HGln-OH; and/or
Xaa¹⁰ is H-β³-HLys-OH; or H-γ⁴-DiHLys-OH; and/or
Xaa¹¹ is hSer; hSer(Me); alloThr; hGln; Dap or H-γ⁴-DiHTyr-OH; and/or
Xaa¹² is $^D$Ala; $^D$Val; $^D$Tyr; or $^D$Lys; and/or
Xaa¹³ is Oic;
and with the further proviso that
if Xaa¹¹ is Tyr, then
Xaa¹ is Dab(Phe).

3. A compound according to claim 1 of the formula I wherein
Xaa¹ is OctGly; Arg; Dab(Octanoyl); or Glu(Phe);
Xaa² is Glu; Phe; Dap(Phe); Val; or hTyr;
Xaa⁴ is Ala; or AllylGly;
Xaa⁶ is Ile;
Xaa⁷ is Pro;
Xaa⁸ is Pro; or Oic;
Xaa⁹ is Gln;
Xaa¹⁰ is Lys;
Xaa¹¹ is Thr; H-γ⁴-DiHThr-OH; Tyr;
Xaa¹² is $^D$Pro; $^D$Val; $^D$Tyr; $^D$Lys; or $^D$Ser; and
Xaa¹³ is Pro; $^D$Pro; Lys; Val; Tyr; H-β³-HPro-OH; $^D$Glu; or Glu;
with the proviso that
Xaa¹ is Dab(Octanoyl); or Glu(Phe); and/or
Xaa² is Dap(Phe); and/or
Xaa⁸ is Oic; and/or
Xaa¹¹ is H-γ⁴-DiHThr-OH; and/or
Xaa¹² is $^D$Val; $^D$Tyr; $^D$Lys; or $^D$Ser; and/or
Xaa¹³ is $^D$Pro; H-β³-HPro-OH; or $^D$Glu;
and with the further proviso that
if Xaa¹¹ is Tyr, then
Xaa¹ is Arg; or Glu(Phe); and/or
Xaa² is Dap(Phe).

4. A compound which is selected from
Cyclo(-OctGly-Glu-Thr-Ala-Ser-Ile-Pro-Pro-Gln-Lys-hSer(Me)-$^D$Pro-Pro-);
Cyclo(-OctGly-Glu-Thr-Ala-Ser-Ile-Pro-Pro-Gln-Lys-Dap-$^D$Pro-Pro-);
Cyclo(-OctGly-Glu-Thr-Ala-Ser-Ile-Pro-Pro-Gln-Lys-alloThr-$^D$Pro-Pro-);
Cyclo(-OctGly-Glu-Thr-Ala-Ser-Ile-Pro-Pro-Gln-Lys-hSer-$^D$Pro-Pro-);
Cyclo(-OctGly-Glu-Thr-Ala-Ser-Ile-Pro-Pro-Gln-Lys-hGln-$^D$Pro-Pro-);
Cyclo(-OctGly-Glu-Thr-Ala-Ser-Ile-Pro-Pro-Gln-Lys-Thr-$^D$Pro-Oic-);
Cyclo(-OctGly-Glu-Thr-Ala-Ser-Ile-Nglu-Pro-Gln-Lys-Thr-$^D$Pro-Pro-);
Cyclo(-OctGly-Glu-Thr-Ala-Ser-Ille-Pro-Pro-Gln-Lys-[H-γ⁴-DiHTyr-OH]-$^D$Pro-Pro-);
Cyclo(-Dab(Phe)-Glu-Thr-Ala-Ser-Ile-Pro-Pro-Gln-Lys-Tyr-$^D$Pro-Pro-);
Cyclo(-OctGly-Glu-Thr-Ala-Ser-Ile-Pro-Oic-Gln-Lys-Thr-$^D$Pro-Pro-);
Cyclo(-OctGly-Glu-Thr-Ala-Ser-Ile-Pro-Pro-Gln-Lys-[H-γ⁴-DiHThr-OH]-$^D$Pro-Pro-);
Cyclo(-OctGly-Glu-Thr-Ala-Ser-Ile-Pro-Pro-Gln-Lys-Thr-$^D$Pro-$^D$Pro-);
Cyclo(-OctGly-Phe-Thr-Ala-Ser-Ile-Pro-Pro-Gln-Lys-Thr-$^D$Pro-Pro-);
Cyclo(-OctGly-Dap(Phe)-Thr-Ala-Ser-Ile-Pro-Pro-Gln-Lys-Tyr-$^D$Pro-Pro-);
Cyclo(-Dab(Octanoyl)-Glu-Thr-Ala-Ser-Ile-Pro-Pro-Gln-Lys-Thr-$^D$Pro-Pro-);
Cyclo(-Arg-Glu-Thr-Ala-Ser-Ile-Pro-Oic-Gln-Lys-Thr-$^D$Pro-Pro-);
Cyclo(-Glu(Phe)-Glu-Thr-AllylGly-Ser-Ile-Pro-Pro-Gln-Lys-Tyr-$^D$Pro-Pro-);
Cyclo(-Glu(Phe)-Glu-Thr-Ala-Ser-Ile-Pro-Pro-Gln-Lys-Tyr-$^D$Pro-Pro-);
Cyclo(-Glu(Phe)-Glu-Thr-AllylGly-Ser-Ile-Pro-Pro-Gln-Lys-Thr-$^D$Pro-Pro-);
Cyclo(-OctGly-Glu-Thr-Ala-Ser-Ile-Pro-Pro-Gln-Lys-Thr-$^D$Ala-Ala-);
Cyclo(-OctGly-Glu-Thr-Ala-Ser-Ile-Pro-Pro-Gln-Lys-Thr-$^D$Val-Tyr-);
Cyclo(-OctGly-Glu-Thr-Ala-Ser-Ile-Pro-Pro-Gln-Lys-Thr-$^D$Val-Lys-);
Cyclo(-OctGly-Glu-Thr-Ala-Ser-Ile-Pro-Pro-Gln-Lys-Thr-$^D$Tyr-Val-);
Cyclo(-OctGly-Glu-Thr-Ala-Ser-Ile-Pro-Pro-Gln-Lys-Thr-$^D$Tyr-Tyr-);
Cyclo(-OctGly-Glu-Thr-Ala-Ser-Ile-Pro-Pro-Gln-Lys-Thr-$^D$Tyr-Lys-);
Cyclo(-OctGly-Glu-Thr-Ala-Ser-Ile-Pro-Pro-Gln-Lys-Thr-$^D$Lys-Val-);
Cyclo(-OctGly-Glu-Thr-Ala-Ser-Ile-Pro-Pro-Gln-Lys-Thr-$^D$Lys-Tyr-);
Cyclo(-OctGly-Glu-Thr-Ala-Ser-Ile-Pro-Pro-Gln-Lys-Thr-$^D$Lys-Lys-);
Cyclo(-OctGly-Glu-Thr-Ala-Ser-Ile-Pro-Pro-Gln-Lys-Thr-$^D$Lys-Glu-);
Cyclo(-OctGly-Glu-Thr-Ala-Ser-Ile-Pro-Pro-Gln-Lys-Thr-$^D$Ser-Val-);
Cyclo(-OctGly-Glu-Thr-Ala-Ser-Ile-Pro-Pro-Gln-Lys-Thr-$^D$Ser-Tyr-);
Cyclo(-OctGly-Glu-Thr-Ala-Ser-Ile-Pro-Pro-Gln-Lys-Thr-$^D$Ser-Lys-);
Cyclo(-OctGly-Glu-Thr-Ala-Ser-Ile-Nlys-Pro-Gln-Lys-Thr-$^D$Pro-Pro-);
Cyclo(-OctGly-Glu-Thr-Ala-Ser-Ile-Pro-Nglu-Gln-Lys-Thr-$^D$Pro-Pro-);
Cyclo(-OctGly-Glu-Thr-Ala-Ser-Ile-Pro-Nlys-Gln-Lys-Thr-$^D$Pro-Pro-);
Cyclo(-OctGly-Glu-Thr-Ala-Ser-Ile-Pro-Pro-[H-β³-HGln-OH]-Lys-Thr-$^D$Pro-Pro-);
Cyclo(-OctGly-Glu-Thr-Ala-Ser-Ile-Pro-Pro-Gln-[H-β³-HLys-OH]-Thr-$^D$Pro-Pro-);
Cyclo(-OctGly-Glu-Thr-Ala-Ser-Ile-Pro-Pro-Gln-[H-γ⁴-DiHLys-OH]-Thr-$^D$Pro-Pro-);
Cyclo(-OctGly-Glu-Thr-Ala-Ser-Ile-Pro-Pro-Gln-Lys-Thr-$^D$Pro-[H-β³-HPro-OH]—);
Cyclo(-OctGly-Glu-Thr-Ala-Ser-Ile-Pro-Pro-Gln-Lys-Thr-$^D$Pro-$^D$Glu-);

Cyclo(-Arg-Val-Thr-Ala-Ser-Ile-Pro-Oic-Gln-Lys-Thr-$^D$Pro-$^D$Pro-);
Cyclo(-Arg-hTyr-Thr-Ala-Ser-Ile-Pro-Oic-Gln-Lys-Thr-$^D$Pro-$^D$Pro-);
Cyclo(-Arg-hTyr-Thr-Ala-Ser-Ile-Pro-Oic-Gln-Lys-Thr-$^D$Pro-Glu-);
Cyclo(-Arg-Val-Thr-Ala-Ser-Ile-Pro-Oic-Gln-Lys-Thr-$^D$Pro-Glu-);
Cyclo(-OctGly-Glu-Thr-Ala-Ser-Ile-Pro-Pip-Gln-Lys-Thr-$^D$Pro-Pro-);
Cyclo(-OctGly-Glu-Thr-Ala-Ser-Ile-Pro-Azt-Gln-Lys-Thr-$^D$Pro-Pro-);
Cyclo(-OctGly-hTyr-Thr-Ala-Ser-Ile-Pro-Pro-Gln-Lys-Ser-$^D$Pro-Pro-);
Cyclo(-OctGly-hTyr-Thr-Ala-Ser-Ile-Pro-Pro-Gln-Lys-Asn-$^D$Pro-Pro-);
Cyclo(-Arg-hTyr-Thr-Ala-Ser-Ile-Pro-Pro-Gln-Lys-Thr-$^D$Pro-Glu-).

5. A method for the treatment of lung cancer; breast cancer; psoriasis; alpha 1 antitrypsin deficiency; pulmonary emphysema; cystic fibrosis; chronic obstructive pulmonary disease; idiopathic pulmonary fibrosis; bronchiectasis; pulmonary hypertension; arterial pulmonary hypertension; cardiac hypertrophy; myocarditis; acute myocardial infarction; rheumatoid arthritis; osteoarthritis; atherosclerosis; multiple sclerosis; pancreatitis; allergic rhinitis; systemic inflammatory respiratory syndrome; inflammatory dermatoses; or inflammatory bowel disease, said method comprising administering the compound according to claim 1, in free form or in pharmaceutically acceptable salt form, or a composition comprising the compound in free form or in pharmaceutically acceptable salt form, and a pharmaceutically inert carrier.

6. A pharmaceutical composition comprising a compound or a mixture of compounds according to claim 1 of the formula I, in free form or in pharmaceutically acceptable salt form, and a pharmaceutically inert carrier.

7. A method for inhibiting activity of elastase for the treatment of infections or diseases related to said infections or cancer or immunological diseases or pulmonary diseases or cardiovascular diseases or neurodegenerative diseases or inflammation or diseases related to inflammation or immunological reactions, said method comprising administering the compound according to claim 1, in free form or in pharmaceutically acceptable salt form, or a composition comprising the compound in free form or in pharmaceutically acceptable salt form, and a pharmaceutically inert carrier.

8. A method of treating an infection or a disease or disorder associated with such an infection resulting from; or cancer mediated or resulting from; or immunological diseases mediated or resulting from; or pulmonary diseases mediated or resulting from; or cardiovascular diseases mediated or resulting from; or neurodegenerative diseases mediated or resulting from; or inflammation mediated or resulting from elastase activity; or where immunological reaction is mediated or resulting from elastase activity, comprising administering to a subject in need thereof a pharmaceutically acceptable amount of the compound according to claim 1, in free form or in pharmaceutically acceptable salt form, or a composition comprising the compound in free form or in pharmaceutically acceptable salt form, and a pharmaceutically inert carrier.

9. A process for the manufacture of a compound as defined in claim 1 of the formula I comprising the steps of
(a) coupling an appropriately functionalized solid support with an appropriately N-protected derivative of that amino acid which in the desired end-product corresponds to Xaa$^n$, wherein n is 13, 8, 7, 6, 5 or 4, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product corresponds to Xaa$^{n-1}$, any functional group which may be present in said N-protected amino acid derivative being likewise appropriately protected;
(d) removing the N-protecting group from the product obtained in step (c);
(e) effecting steps substantially corresponding to steps (c) and (d) using appropriately N-protected derivatives of amino acids which in the desired end-product are in positions n−2 to 1, any functional group(s) which may be present in said N-protected amino acid derivatives being likewise appropriately protected;
(f) if n is not 13, further effecting steps substantially corresponding to steps (c) and (d) using appropriately N-protected derivatives of amino acids which in the desired end-product are in positions 13 to n+1, any functional group(s) which may be present in said N-protected amino acid derivatives being likewise appropriately protected;
(g) detaching the product thus obtained from the solid support;
(h) cyclizing the product cleaved from the solid support;
(i) removing any protecting groups present on functional groups of any members of the chain of amino acid residues; and
(j) if desired, converting the product thus obtained into a pharmaceutically acceptable salt or converting a pharmaceutically acceptable, or unacceptable, salt thus obtained into the corresponding free compound or into a different, pharmaceutically acceptable, salt.

10. The method according to claim 5, wherein the inflammatory bowel disease is Crohn's disease.

11. The pharmaceutical composition according to claim 6, said pharmaceutical composition being in a form suitable for inhalation, for oral, topical, transdermal, injection, buccal, transmucosal, rectal, pulmonary or inhalation administration.

12. The pharmaceutical composition according to claim 11, said pharmaceutical composition being in the form of a tablet, dragee, capsule, solution, liquid, gel, plaster, cream, ointment, syrup, slurry, suspension, powder or suppository.

* * * * *